US005486919A

United States Patent [19]
Tsuji et al.

[11] Patent Number: 5,486,919
[45] Date of Patent: Jan. 23, 1996

[54] INSPECTION METHOD AND APPARATUS FOR INSPECTING A PARTICLE, IF ANY, ON A SUBSTRATE HAVING A PATTERN

[75] Inventors: Toshihiko Tsuji, Ayase; Seiji Takeuchi, Kawasaki; Kyoichi Miyazaki, Mitaka; Minoru Yoshii, Tokyo; Noriyuki Nose; Tetsuzo Mori, both of Atsugi, all of Japan

[73] Assignee: Canon Kabushiki Kaisha, Tokyo, Japan

[21] Appl. No.: 76,951

[22] Filed: Jun. 15, 1993

Related U.S. Application Data

[63] Continuation-in-part of Ser. No. 900,736, Jun. 16, 1992, abandoned, and a continuation-in-part of Ser. No. 26,288, Mar. 4, 1993, abandoned.

[30] Foreign Application Priority Data

| Apr. 27, 1992 | [JP] | Japan | 4-107678 |
| May 28, 1992 | [JP] | Japan | 4-136982 |
| Jun. 16, 1992 | [JP] | Japan | 4-156842 |
| Nov. 16, 1992 | [JP] | Japan | 4-305422 |
| Nov. 16, 1992 | [JP] | Japan | 4-305433 |
| Feb. 10, 1993 | [JP] | Japan | 4-022675 |
| Mar. 9, 1993 | [JP] | Japan | 4-048064 |
| Apr. 26, 1993 | [JP] | Japan | 4-099541 |

[51] Int. Cl.[6] ................................................. G01B 9/02
[52] U.S. Cl. ................... 356/349; 356/345; 356/237; 356/351
[58] Field of Search ................... 356/237, 345, 356/349, 354, 351

[56] References Cited

U.S. PATENT DOCUMENTS

| 4,669,875 | 6/1987 | Shiba et al. | 356/237 |
| 4,710,026 | 12/1987 | Magome et al. | 356/349 |
| 4,764,013 | 8/1988 | Johnston | 356/349 |
| 4,842,408 | 6/1989 | Yoshii et al. | 356/349 |
| 4,893,932 | 1/1990 | Knollenberg | 356/369 |
| 4,898,471 | 2/1990 | Stonestrom et al. | 356/394 |
| 5,170,063 | 12/1992 | Miyazaki et al. | 250/572 |
| 5,343,290 | 8/1994 | Batchelder et al. | 356/349 |

FOREIGN PATENT DOCUMENTS

| 0567701 | 11/1993 | European Pat. Off. . |
| 3714305 | 11/1987 | Germany . |

OTHER PUBLICATIONS

Patent Abstracts of Japan, Kokai No. 2-307046, vol. 15, No. 91, Mar. 1991.
Patent Abstracts of Japan, Kokai No. 61-260211, vol. 11, No. 112, Apr. 1987.
Patent Abstracts of Japan, Kokai No. 3-249550, vol. 16, No. 46, Feb. 1992.
Nishino, et al., "Reticle Particle Detection System," Hitachi Review, vol. 40, No. 6, Dec. 1991, pp. 395 through 400.

*Primary Examiner*—Samuel A. Turner
*Assistant Examiner*—Robert Kim
*Attorney, Agent, or Firm*—Fitzpatrick, Cella, Harper & Scinto

[57] ABSTRACT

Disclosed is an inspection method and apparatus: wherein (i) first light having a first state of polarization and a first wavelength, and (ii) second light having a second state of polarization, different from the first state of polarization, and a second wavelength, different from the first wavelength are produced; at least the first light is projected to a position of inspection; and heterodyne interference light produced on the basis of the second light and light scattered at the inspection position and having its state of polarization changed, by the scattering, from the first state of polarization, is detected.

28 Claims, 59 Drawing Sheets

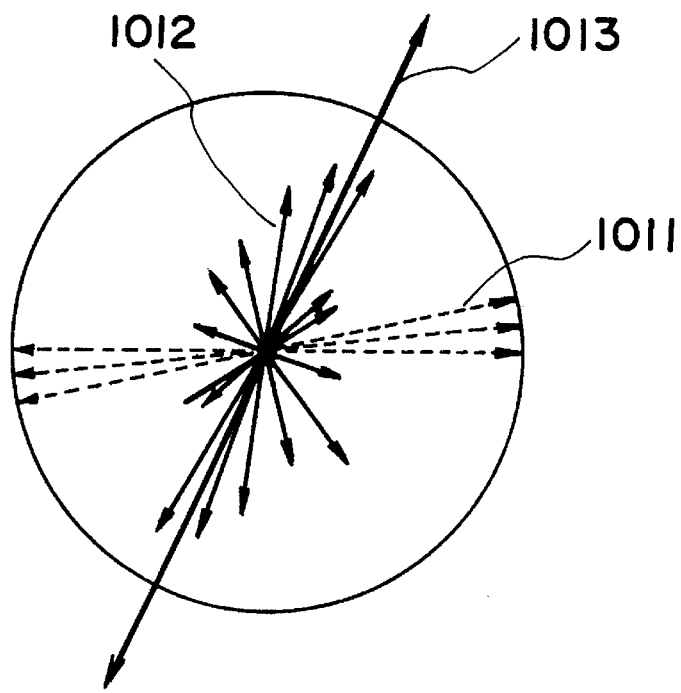
F I G. 10
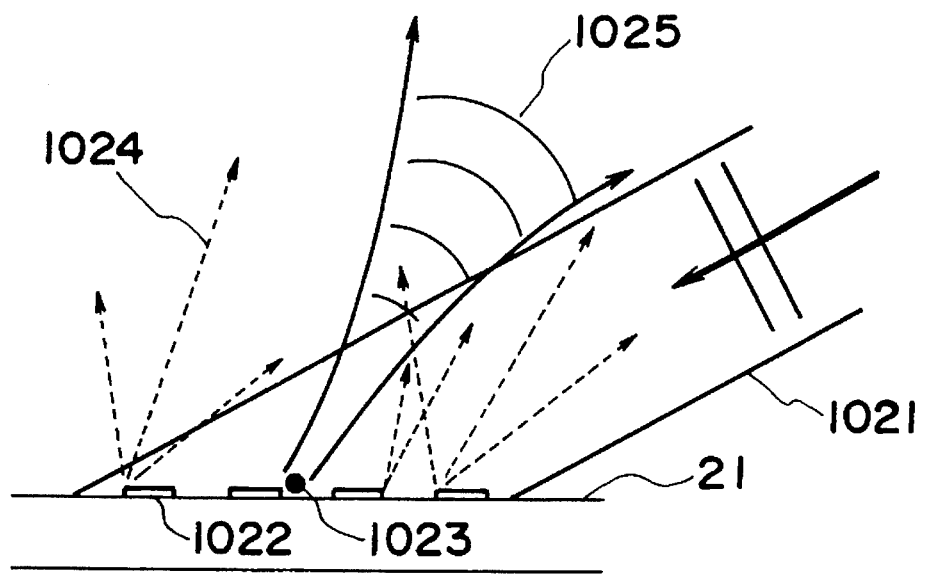
F I G. 11

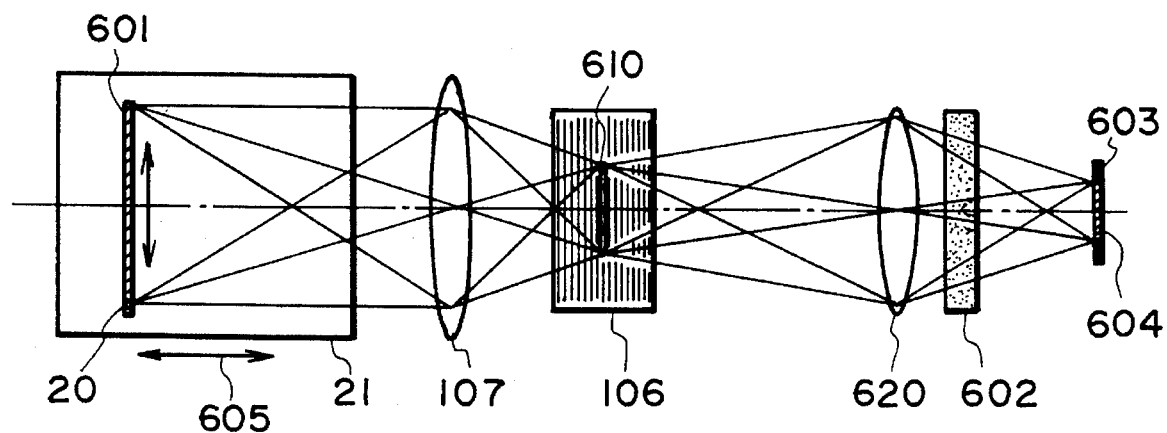
F I G. 14
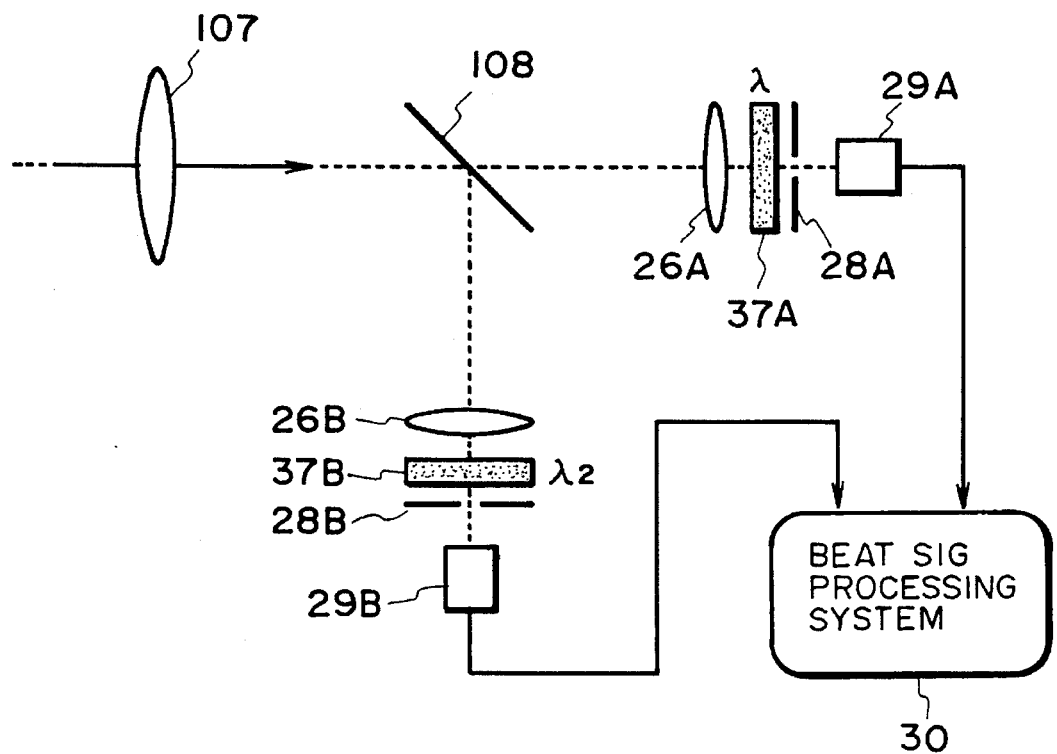
F I G. 15

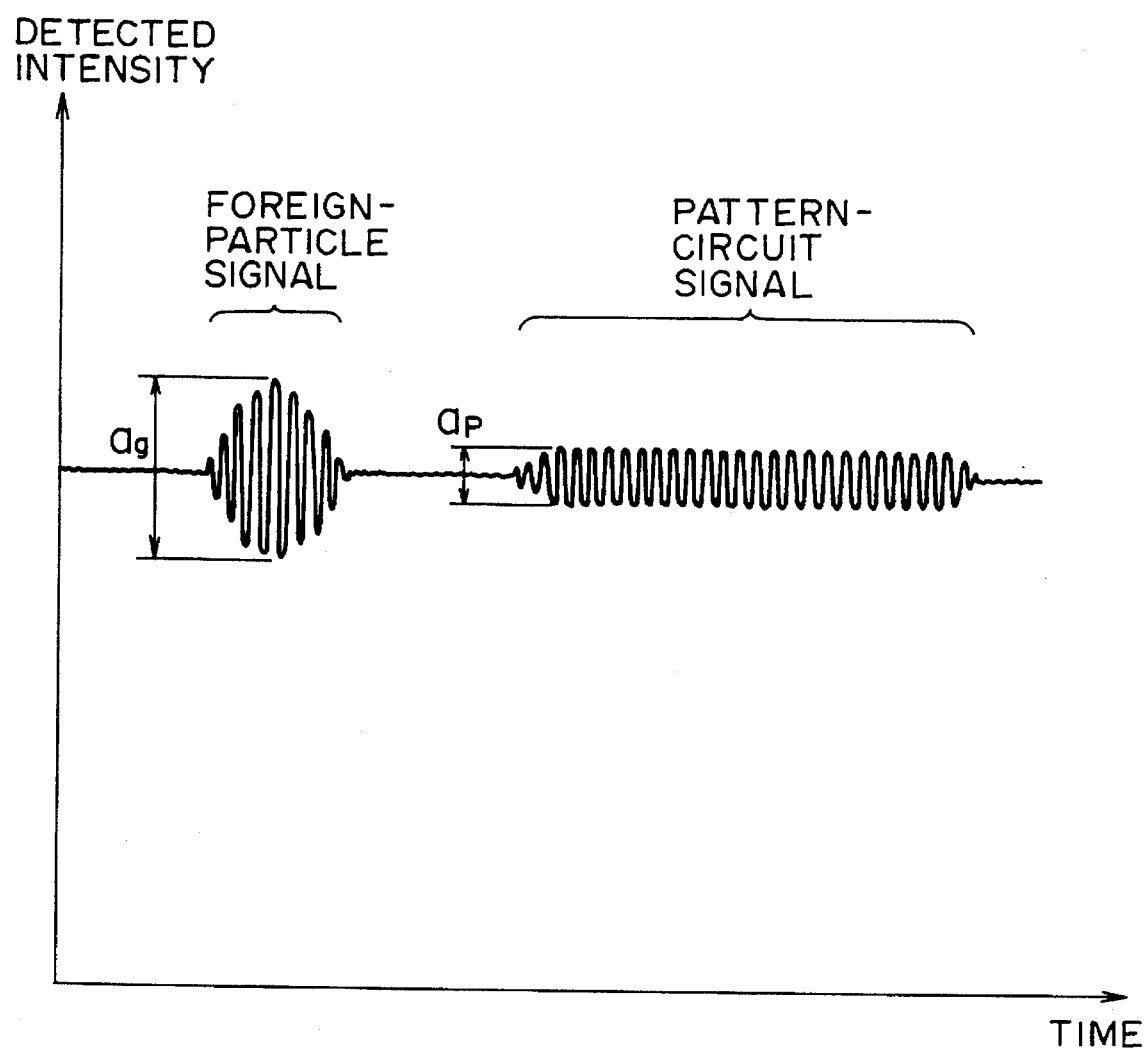
F I G. 30

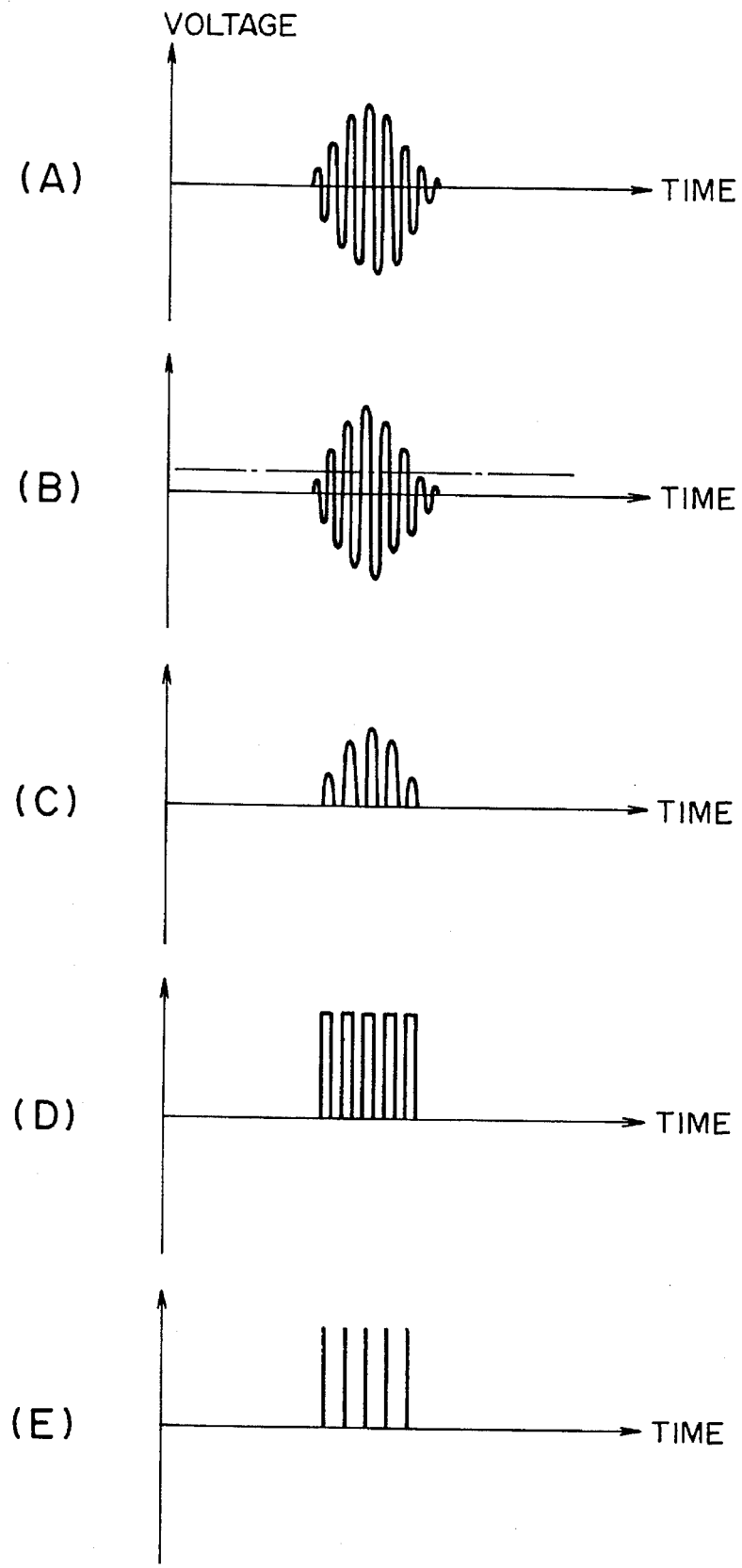
F I G. 36

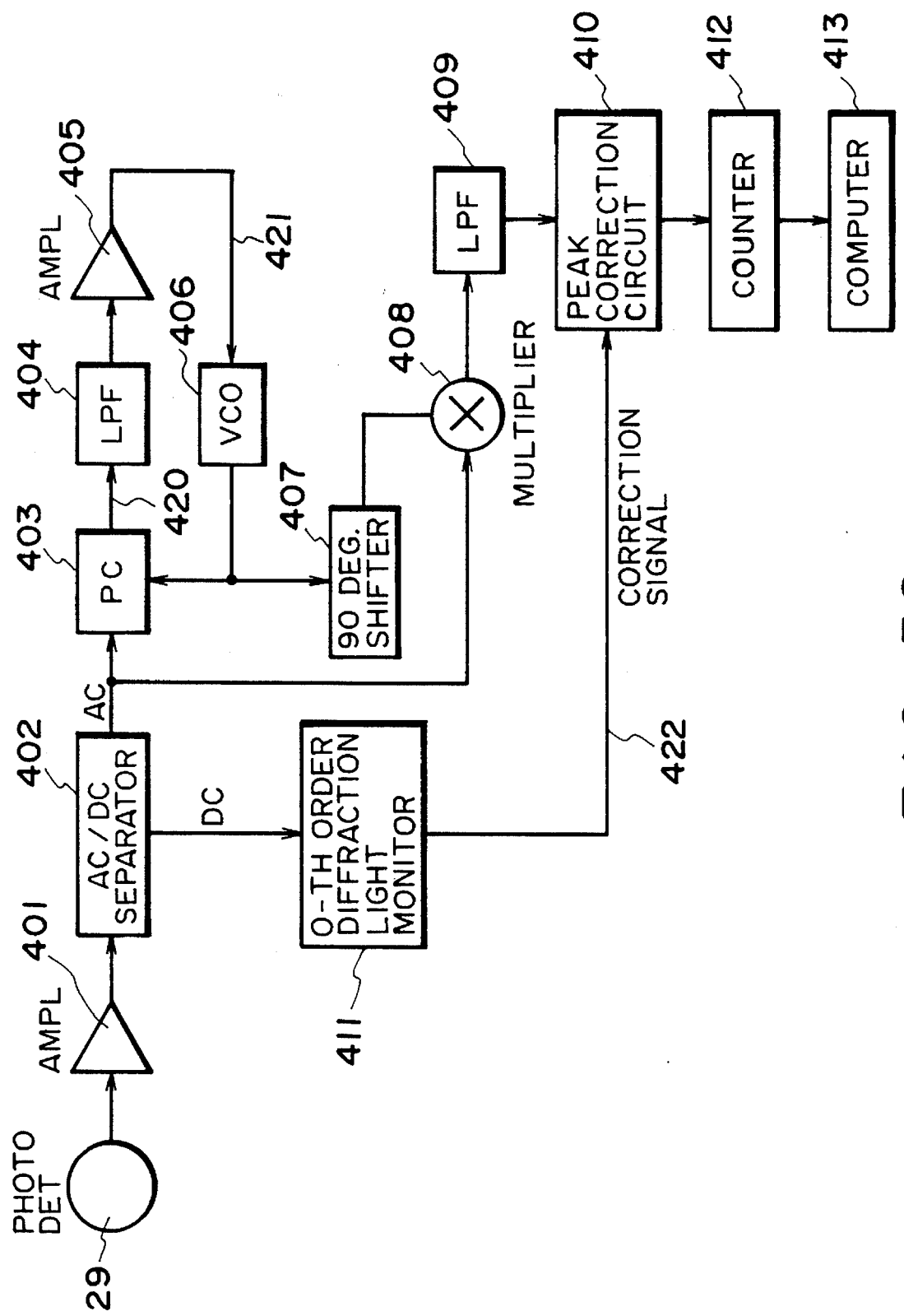
F I G. 59

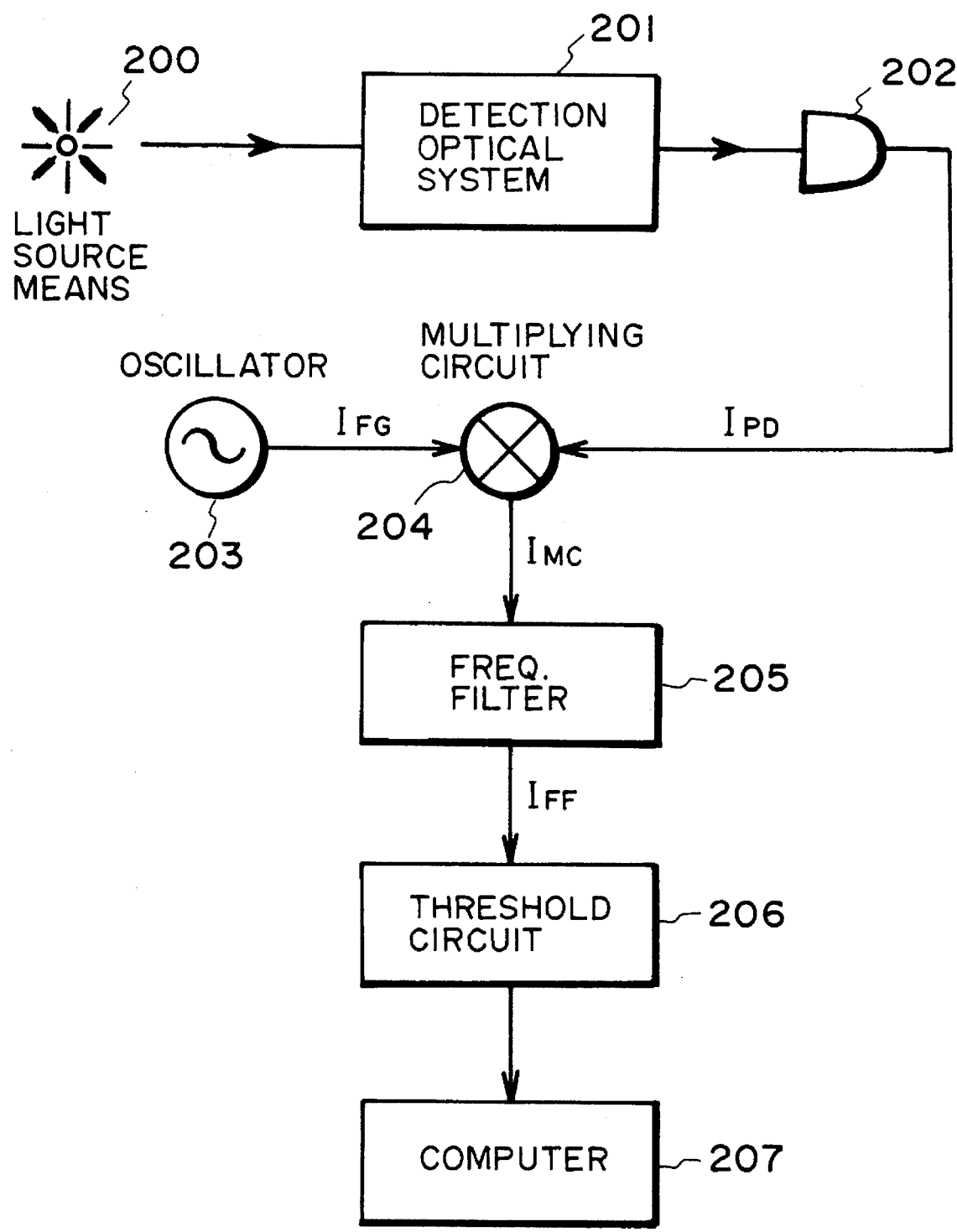
F I G. 61

1

INSPECTION METHOD AND APPARATUS FOR INSPECTING A PARTICLE, IF ANY, ON A SUBSTRATE HAVING A PATTERN

This application is a continuation-in-part of application Ser. No. 07/900,736, filed Jun. 16, 1992, now abandoned and a continuation-in-part of application Ser. No. 08/026,288, filed Mar. 4, 1993 now abandoned.

FIELD OF THE INVENTION AND RELATED ART

This invention relates to a method and an apparatus usable, as an example, in the manufacture of microdevices such as semiconductor devices, for inspecting the surface of an article. More particularly, the invention is concerned with a method and an apparatus for optically inspecting the presence/absence of minute particles or defects of the surface of an article. In another aspect, the invention is concerned with a method and an apparatus for manufacturing microdevices such as semiconductor devices by using such an inspection method.

For manufacture of semiconductor devices such as ICs or liquid crystal displays, for example, a circuit pattern formed on an original (called a "reticle" or "photomask") is transferred to the surface of a workpiece or wafer having a resist coating by using a semiconductor printing apparatus (called an "exposure apparatus"). If in this transfer process there are minute particles (foreign particles) on the surface of the original, such particles are also transferred (printed) on the wafer. This causes decreased yield of IC manufacture. Particularly, in a case where the same circuit pattern is printed on different zones of a wafer sequentially in accordance with the step-and-repeat method, only one particle on the original is printed on every zone of the wafer. This results in a possibility that all the chips produced from this wafer are defective, leading to a substantial decrease in the yield of IC manufacture.

In the IC manufacturing process, it is therefore desired to inspect the presence/absence of minute particles on an original, and many proposals have been made in this respect. FIG. 66 shows an example of an inspection apparatus. In this example, the presence/absence of any foreign particle is examined by detecting scattered light from the particle.

More particularly, in FIG. 66, a laser beam from a laser light source 151 is transformed into a laser beam best suited to inspection, by means of a polarizer 152, a filter 153, a collimating system 154 and so on. Mirror 155 directs the laser beam to a scanning optical system comprising a scanning mirror 157 and an f-θ lens 158. The scanning laser beam from the f-θ lens 158 is converged on the surface 160, to be inspected, of a reticle or the like having a circuit pattern formed thereon, and thus a scanning light spot 159 is formed thereon. Scanning stage system 166 serves to relatively move the scanning spot 159 and the surface 160 in a direction perpendicular to the direction of the scan by the scanning spot 159, whereby a two-dimensional scan of the entire surface 160 is assured.

A detection system comprising a lens system 161, a polarizer 162, an aperture 163 and a photoelectric detector 164 is disposed to receive backward or sideward scattered light. As regards the disposition of this detection system, since there is scattered light from the circuit pattern or the like on the surface 160 which light has a particular direction of diffraction, the detection system has to be disposed off such a direction so as not to receive the unwanted diffraction light.

If in this structure there is no particle within the range of the scanning spot 159, no scattered light is detected by the photoelectric detector 164. If there is any particle, it produces scattered light isotropically and, therefore, the photoelectric detector 164 detects any scattered light. Thus, by processing an output signal of the detector in a signal processing system 165, the presence/absence of any foreign particle on the surface can be inspected.

However, this type of inspection apparatus involves such inconveniences as follows:

(1) Where a very small particle of a size of about 0.3 micron or less is to be detected, the produced scattered light has a very low intensity. It is therefore not easy to detect the particle-scattered light with good sensitivity.

(2) There is a case wherein, depending on the circuit pattern used, scattered light goes from the pattern toward the detector. In the detection system like this example which is based only on the intensity information of the scattered light, it is not easy to discriminate the particle-scattered light from the pattern-scattered light. This leads to a decreased signal-to-noise (S/N) ratio.

SUMMARY OF THE INVENTION

It is accordingly an object of the present invention to provide an inspection method or apparatus by which even very small particles or defects on a surface can be detected with a good S/N ratio.

It is another object of the present invention to provide a method or apparatus for manufacture of microdevices such as semiconductor devices, using such an inspection method.

In accordance with an aspect of the present invention, there is provided an inspection apparatus comprising: light producing means for producing (i) a first light beam having a first state of polarization and a first wavelength, and (ii) a second light beam having a second state of polarization, different from the first state of polarization, and a second wavelength, different from the first wavelength; light projecting means for projecting at least the first light beam to a position of inspection; and detecting means for detecting heterodyne interference light produced on the basis of the second light beam and the light scattered at said position and having its state of polarization changed by the scattering from the first state of polarization.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 10 is a schematic view for explaining reference light and scattered light.

FIG. 11 is a schematic view for explaining the difference in wave front of scattered lights from a circuit pattern and from a particle.

FIG. 14 is a schematic view of a detection optical system of this embodiment.

FIG. 15 is a schematic view of a modified form of the detection system of the fourth embodiment.

FIG. 30 is a schematic view, showing an example of the waveform of a detection signal which is obtainable with the apparatus of the eleventh embodiment.

FIG. 36 is a schematic view, showing the waveforms of signals at respective portions of the signal processing circuit of FIG. 35.

FIG. 59 is a diagrammatic view of a twenty-sixth embodiment of the present invention.

FIG. 61 is a schematic and diagrammatic view of a twenty-seventh embodiment of the present invention.

DESCRIPTION OF THE PREFERRED EMBODIMENTS

Now, description will be made of some preferred embodiments of the present invention which is applied to an apparatus for inspecting a surface of an article such as an original (reticle or photomask) or a workpiece (wafer) used the in manufacture of semiconductor devices, more particularly, to an apparatus for inspecting foreign particles such as dust adhered to the surface to be examined or any defects such as scratches on that surface. As a matter of course, the invention is applicable not only to the field of semiconductor device manufacture but also to any other fields wherein the surface inspection is required.

Embodiment 1

Figure 1:
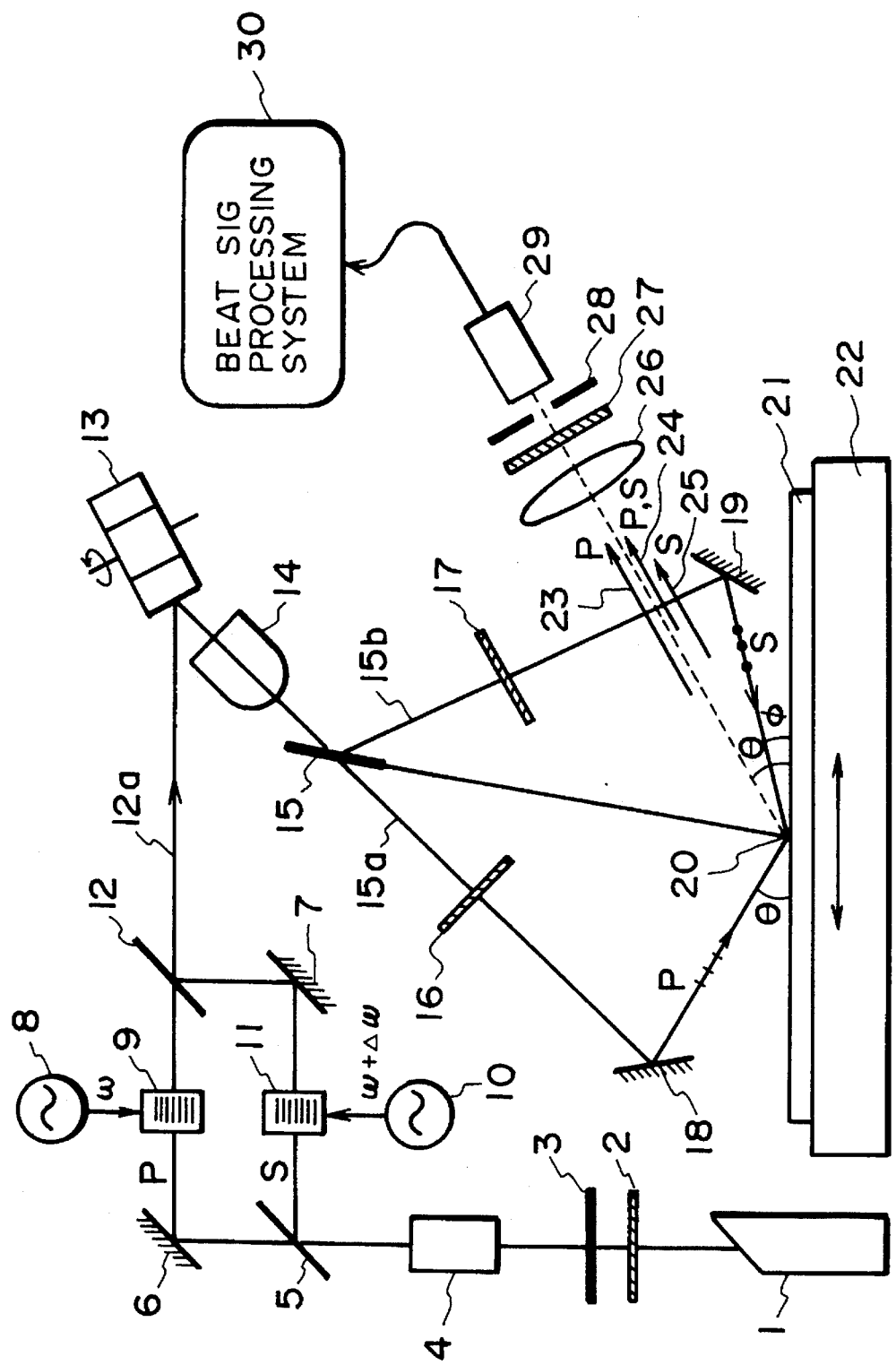
FIG. 1 is a schematic view of a first embodiment of the present invention.

FIG. 1 shows a first embodiment of the present invention. Denoted in the drawing at 1 is a laser light source; at 2 is a polarizing plate: at 3 is a filter system; at 4 is a collimator optical system; at 5 and 12 are polarization beam splitters each for separating a laser beam into two mutually orthogonal polarization light components or for combining them; at 6 and 7 are mirrors; at 8 and 9 (10 and 11) are a set of an acousto-optic device and a driver therefor, for modulating the laser beam at a suitable shift frequency; at 13 is a scanning mirror such as a polygonal mirror or a galvano mirror; at 14 is an f-θ lens system; at 15 is a polarization beam splitter having an elongated shape corresponding to the region to be scanned; at 16 and 17 are intensity attenuating filter systems; at 18 and 19 are mirrors; at 20 is a scanning spot; at 21 is the surface of a reticle or the like which is to be inspected; at 22 is a scanning stage system; at 26 is a lens system for directing scattered light from the scanning spot 20 to a photoelectric detector 29; at 27 is a polarization filter; at 28 is a slit-like aperture; at 29 is the aforesaid photoelectric detector; and at 30 is a beat signal processing system.

The laser beam produced by the laser light source 1 is transformed by the polarizing plate 2 and the filter system 3 into a laser beam of suitable intensity having mutually orthogonal linearly polarized light components, which is then collimated by the collimator optical system. This laser beam is then separated by the polarization beam splitter 5 into a P-polarized laser beam and an S-polarized laser beam. Of these laser beams, the P-polarized laser beam is reflected by the mirror 6 and is modulated at a shift frequency ω by the acousto-optic device 9 which is driven by the driver 8. On the other hand, the S-polarized laser beam is modulated at a shift frequency ω+Δω by the acousto-optic device 11 which is driven by the driver 10, and it is reflected by the mirror 7. These two linearly polarized and frequency modulated laser beams are combined by the polarization beam splitter 12, whereby a single laser beam 12a having two mutually orthogonal, linearly polarized light components with a difference attributable to the relative shift frequency difference Δω, is produced.

As regards the arrangement for producing such a laser beam 12a as having the above-described property, it is not limited to the above-described example. An alternative is that only one acousto-optic device is used to modulate only one of the two laser beams at a shift frequency Δω. As a further alternative, a Zeeman laser light source may be used or an injection current to a semiconductor laser light source may be modulated.

The laser beam 12a is directed to an optical scanning system which comprises the scanning mirror 13 and the f-θ lens system 14, and the laser beam emanating therefrom is separated by the polarization beam splitter 15 into a P-polarized laser beam 15a (shift frequency ω) and an S-polarized laser beam 15b (shift frequency ω+Δω).

The separated laser beam 15a is received by the filter system 16 whereby an intensity suitable to the particle inspection is set. Then, it is converged through cooperation of the mirror 18 upon the surface 21, to be inspected, at an angle of incidence (θ), whereby a spot 20 is formed. On the other hand, the S-polarized laser beam 15b is received by the filter system 17 whereby an intensity suitable to the particle inspection is set. Then, it is converged through cooperation of the mirror 19 at an angle of incidence (φ), into a spot 20 on the surface 21. Namely, the laser beams 15a and 15b are converged into the same spot 20 at different incidence angles. The intensity ratio of the laser beams 15a and 15b impinging on the spot 20 may be 1:100, for example. Also, the spot 20 may have a size of about 10 microns. Here, as regards the optical length from the polarization beam splitter 15 to the scanning spot 20, the same length is set to the P-polarized laser beam 15a and the S-polarized laser beam 15b. This assures "interference" even when the spatial coherent length of the laser beam is not very long. Also, while the photoelectric detector 29 is disposed in the direction of zero-th order diffraction light (angle of emission of θ) of the P-polarized laser beam 15a (angle of incidence of θ), this angle may be so selected as to minimize impingement upon the detector 29 of that scattered light which is produced from anything other than a foreign particle or a fault on the surface 21 (for example, light diffractively scattered by a circuit pattern of a reticle).

With the rotation of the scanning mirror 13, the scanning spot 20 moves along a direction perpendicular to the sheet of the drawing, to optically scan the surface 21. Also, the scanning stage 22 relatively moves the surface 21 in a direction (depicted by an arrow in the drawing) perpendicular to the optical scan direction with the spot 20, whereby the surface 21 as a whole can be scanned two-dimensionally.

In the present embodiment, particular notice is taken of three kinds of light, among those produced from the scanning spot 20 toward the photoelectric detector 29, that is: (1) zero-th order diffraction light 23 (P-polarized light) of the P-polarized laser beam 15a; (2) back scattered light 24 (P-polarized light plus S-polarized light) of the S-polarized laser beam 15b, depolarized by a foreign particle or fault; and (3) back scattered light 25 (S-polarized light) of the S-polarized laser beam 15b, produced by the circuit pattern formed on the surface 21. Here, the cause of depolarization attributable to a foreign particle or fault on the surface is that: since generally the surface irregularity on such a foreign particle or fault is large, when the light is irregularly reflected and scattered, the state of polarization is disturbed to generate a polarized component different from the plane of polarization of the input light. If, on the other hand, the surface is relatively uniform and smooth, such as the surface on a circuit pattern, the depolarization of scattered light is small.

The zero-th order diffraction light 23 of P-polarized light (shift frequency ω) produced in the direction toward the photoelectric detector 29 and the P-polarized light component of the back scattered light 24 (shift frequency ω+Δω) attributable to any particle or fault, have the same or coinciding plane of polarization. Therefore, they cause optical heterodyne interference. By photoelectrically converting this interference light, a beat signal is obtained. Namely, in the optical heterodyne method, since the zero-th order diffraction light 23 is a reference light and it comprises P-polarized light, the light that can interfere with this light to provide a beat signal, is only the scattered light 24 (among those back scattered) which has a P-polarized light component as a result of depolarization. This means that: if there is scattered light from a circuit pattern, it does not cause a beat signal; or alternatively, if a beat signal is produced, it is of very low level. Thus, the present embodiment assures inspection of any foreign particle or fault, with a very high sensitivity and a very high S/N ratio.

The above-described scattered light as received by the lens system 26 is then received by the polarization filter 27 having an optical property effective to pass only a P-polarized light component, whereby unwanted light components such as an S-polarized light component can be blocked. This effectively reduces beat signal noises attributable to unwanted mixture of noise polarized light. After this, the light passes through the slit-like aperture 28 and reaches the photoelectric detector 29. The detection signal obtained by the detector 29 is processed by the beat signal processing system 30, and the presence/absence of any foreign particle or fault is discriminated on the basis of the state of the beat signal.

In the present embodiment, the zero-th order diffraction light 23 comprising P-polarized light is used as a reference light and it is caused to interfere (heterodyne interference) with the P-polarized light resulting from depolarization, to thereby obtain a beat signal. However, even if the relationship of the P-polarization and the S-polarization is interchanged totally, the detection can be done in a similar way. An example of doing this may be that: the characteristics of the polarization beam splitter 15 are changed so as to provide a laser beam 15a of S-polarized component and a laser beam 15b of P-polarized component while, on the other hand, a polarization filter 27 having a property for passing only S-polarized light components is used.

Figure 2:
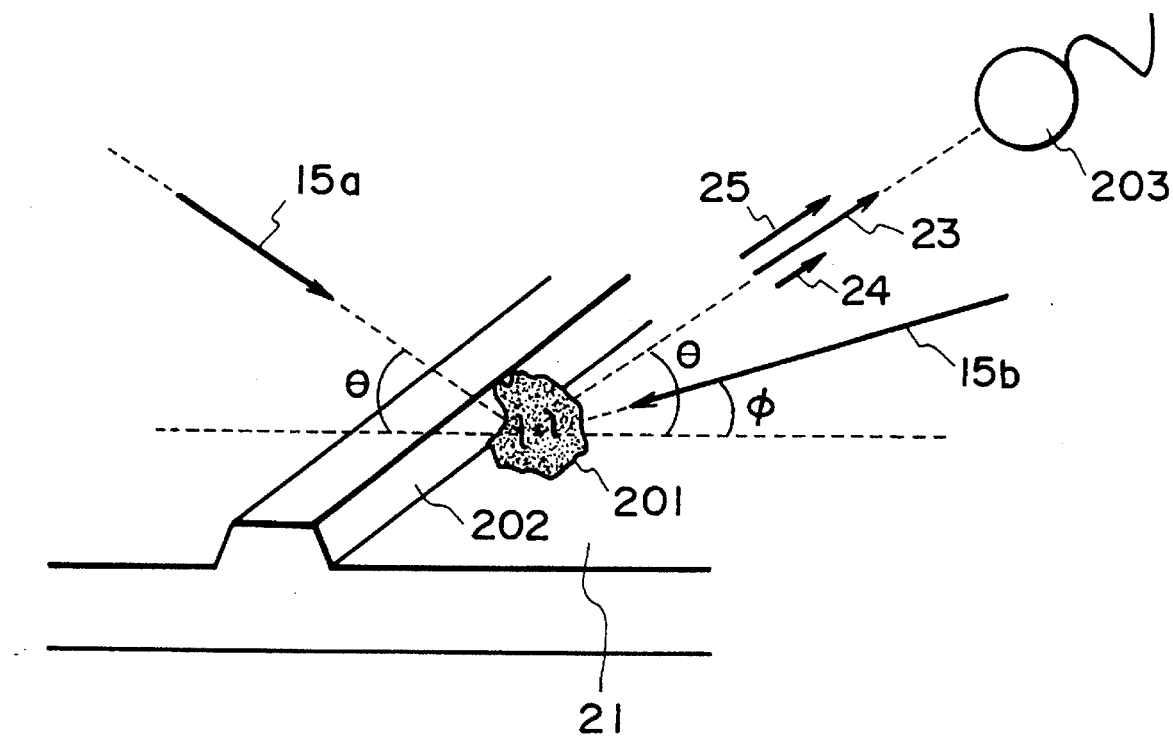
FIG. 2 is a schematic view for explaining the generation of scattered light and detection of a beat signal.

Next, generation of scattered light as well as detection of a beat signal in the present embodiment will be explained in greater detail. FIG. 2 illustrates generation of scattered light on an occasion when a foreign particle and a circuit pattern are present in the neighborhood of the position of a scanning spot. Denoted in the drawing at 201 is a foreign particle of a size of about 0.3 micron, adhered to the surface 21 to be inspected; at 202 is a circuit pattern; and at 203 is a beat signal detecting system including a polarization filter, as an example.

As described with reference to FIG. 1, the P-polarized laser beam 15a having been modulated at a shift frequency $\omega$ and the S-polarized laser beam 15b having been modulated at a shift frequency $\omega+\Delta\omega$, are incident on the same spot position with respective angles of incidence of $\theta$ and $\phi$. The beat signal detecting system 203 is disposed in the direction in which the zero-th order diffraction light is produced from the laser beam 15a by the surface 21 to be inspected and, with regard to the S-polarized laser beam 15b, the beat signal detecting system 203 is disposed in the direction of back scattering.

Here, since as compared with the size (about 0.3 micron) of particles to be inspected the scanning spot has a sufficiently large diameter of about 10 microns, irrespective of the presence or absence of such a particle the zero-th order diffraction light 23 can reach the beat signal detecting system 203 while the state of polarization of the input light is retained substantially unchanged. This can be explained from the fact that, in the phenomenon of diffraction of light, the higher the order of diffraction of light is, the more it depends on the high frequency component (spatial frequency) of the reflection surface while the zero-th order diffraction light depends on the low frequency component of the reflection surface. Namely, the zero-th order diffraction light is less affected by a minute structure within the spot.

Assuming now that the P-polarized laser beam 15a and the S-polarized laser beam 15b impinging on the surface 21 have respective electric fields $E_1$ and $E_2$, then they can be expressed as follows:

$$E_1 = Ep \cdot exp\{j(\omega t + \theta_1)\} \quad (1)$$

$$E_2 = Es \cdot exp[j\{(\omega+\Delta\omega)t+\theta_2\}] \quad (2)$$

Now, if the zero-th order diffraction light 23 from the scanning spot 20, the back scattered light 24 by the foreign particle and the back scattered light 25 by the circuit pattern are denoted by $F_1$, $R_1$ and $R_2$, respectively, then they can be expressed as follows:

$$F_1 = \alpha Ep \cdot exp\{j(\omega t + \theta'_1)\} \quad (3)$$

(where $\alpha$ is the efficiency of zero-th order diffraction)

$$R_1 = \Delta E_1 s \cdot exp[j\{(\omega+\Delta\omega)t+\theta'_2\}] + \Delta E_1 p \cdot exp[j\{(\omega+\Delta\omega)t+\theta'_2\}] \quad (4)$$

$$R_2 = \Delta E_2 s \cdot exp[j\{(\omega+\Delta\omega)t+\theta'_3\}] \quad (5)$$

Here, since only those having the same or coinciding plane of polarization cause interference and since any S-polarized component is blocked by a polarization filter included in the beat detecting system 203, the intensity I of a combined beat signal to be detected by the beat signal detecting system 203 can be expressed as follows:

$$\begin{aligned} I &= |F_1 + R_1 + R_2|^2 \\ &= (\alpha Ep)^2 + \Delta E_1 p^2 + \\ &\quad 2\alpha Ep \Delta E_1 p \cdot cos(\Delta\omega t + \theta'_2 - \theta'_1) \end{aligned} \quad (6)$$

The amplitude $\Delta E_1 p$ of the P-polarized component, produced as a result of depolarization by the particle defined by equation (4), is very small. Since, however, from the third term of equation (6), Ep is significantly larger than $\Delta E_1 p$, the output voltage of the beat signal detected by the beat signal detecting system 203 has a good sensitivity as compared with a case where the back scattered light 24 by the particle is detected directly.

Also, where the DC component and the AC component (frequency $\Delta\omega$) of the beat signal obtained in equation (6) are extracted selectively in accordance with an appropriate method, it is possible to avoid noise components such as stray light to thereby further enhance the S/N ratio.

Figure 3:
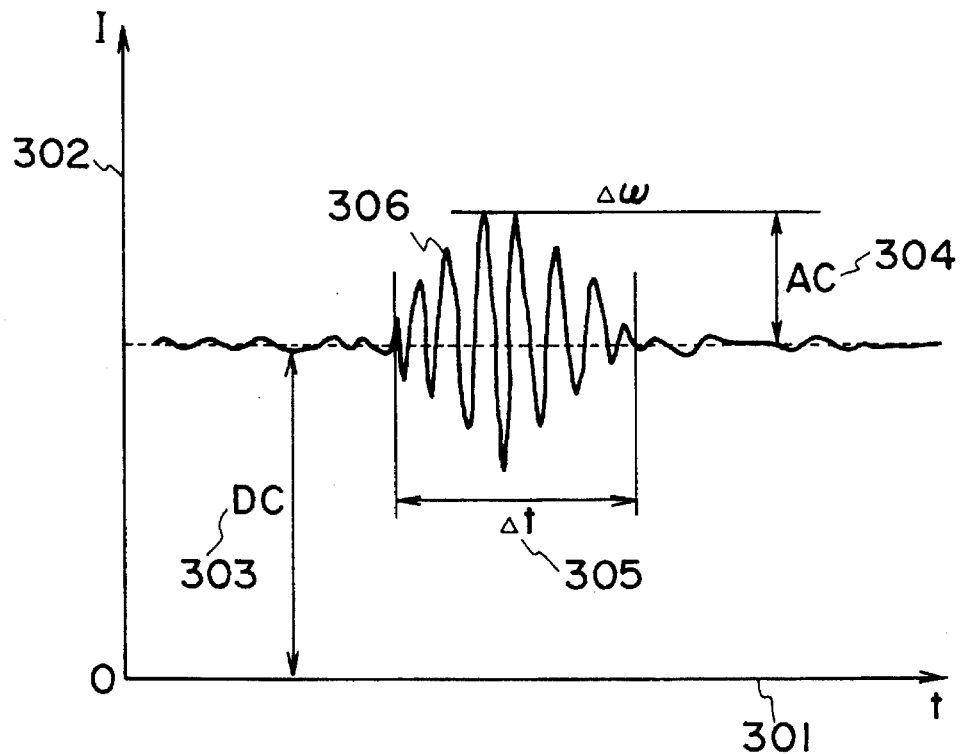
FIG. 3 is a schematic view for explaining a beat signal detected.

Now, the beat signal to be detected will be explained. FIG. 3 shows an example of the waveform of such a beat signal. Denoted in the drawing at 301 is the axis which represents time t; at 302 is the axis which represents the intensity I of the signal outputted; at 306 is the beat signal to be detected; at 303 is the DC component of the beat signal; at 304 is the AC component of the beat signal; at 305 is the time width or period ($\Delta t$) in which the beat signal is detected.

Figure 4:
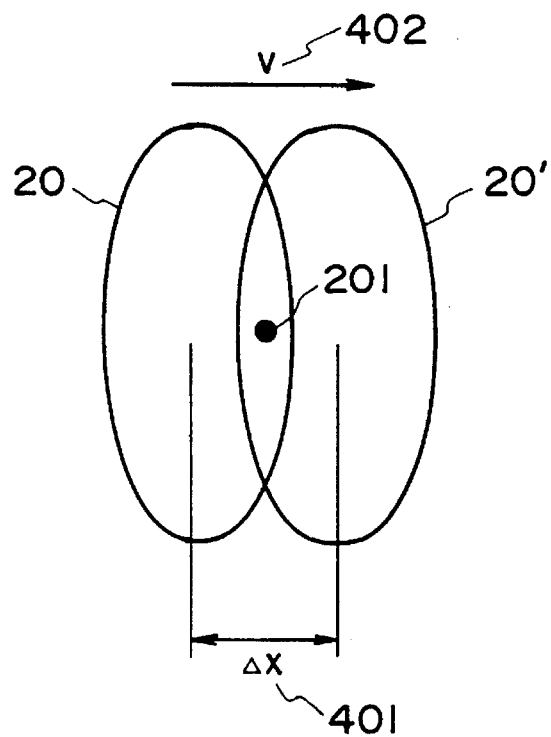
FIG. 4 is a schematic view for explaining the time width of a beat signal detected.

As described hereinbefore, if there is no particle or fault within the scanning light spot, then no beat signal is detected. However, if there is any particle or fault, a beat signal of a frequency $\Delta\omega$ as depicted at 306 is produced in the time width $\Delta t$. This time width $\Delta t$ (305) in which the beat signal is produced is determined by the size of the scanning spot 20 and the scan speed of the spot 20 over the surface to be inspected. Namely, in FIG. 4, the time period from a moment at which an end of the scanning spot 20 moving at a speed V (402) just reaches the particle 201 to a moment at which the scanning spot 20 comes just to the position 20', corresponds to the beat signal time width Δt (305) in FIG. 3.

Figure 5:
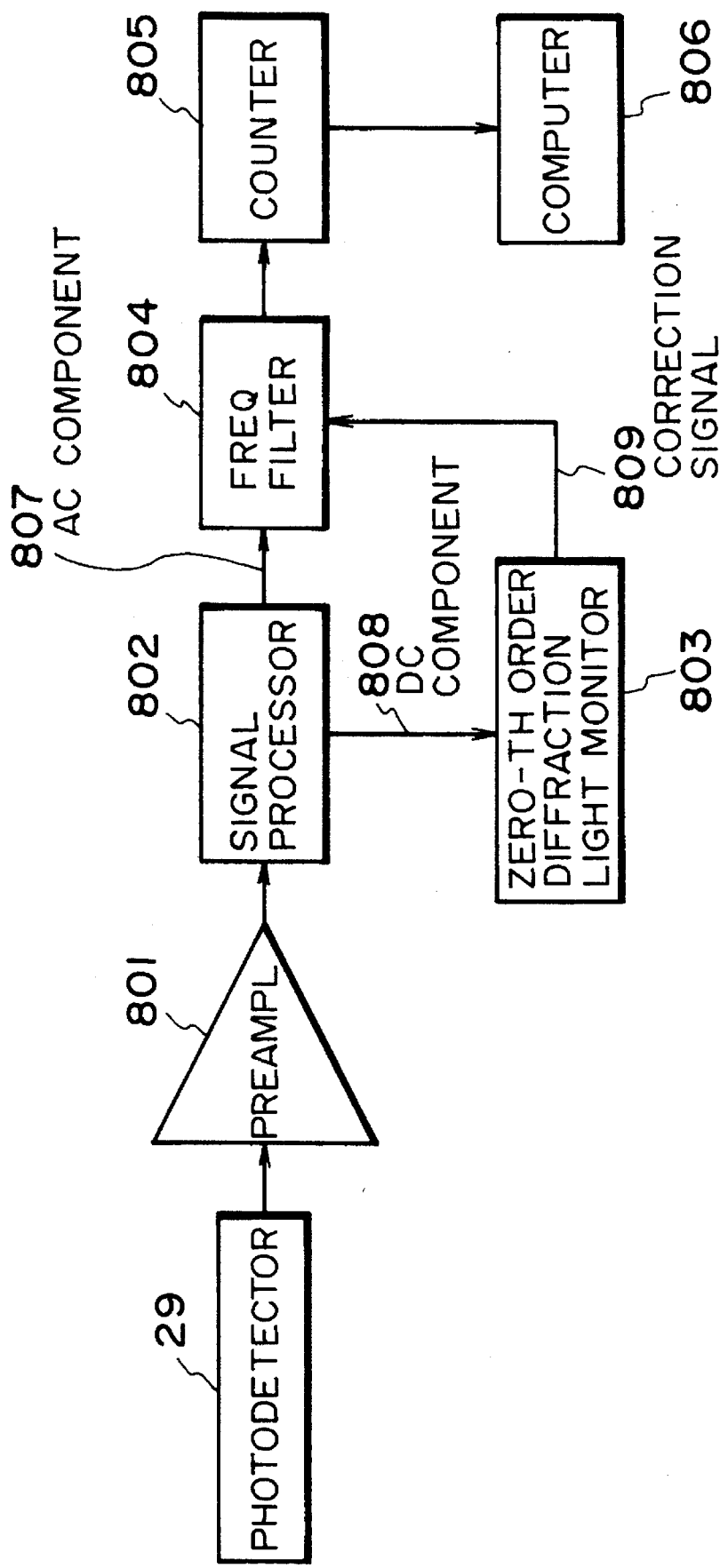
FIG. 5 is a diagrammatic view of a beat signal detecting system.

Referring now to FIG. 5, details of an example of the structure of the beat signal processing system 30, for processing a beat signal detected, will be explained. Denoted in the drawing at 801 is a preamplifier for amplifying a beat signal detected by the photoelectric detector 29; at 802 is a signal processing system for detecting individually the DC component 808 and the AC component 807 of the amplified beat signal; at 803 is a zero-th order diffraction light monitor system for monitoring any change in intensity of the zero-th order diffraction light 23, through detection of the DC component 808; at 809 is a correction signal for correcting a change in intensity of the zero-th order diffraction light 23 as detected by the monitoring; at 804 is a frequency filter for extracting a signal of frequency Δω of the detected AC component, for correction with the correction signal 809; at 805 is a counter for counting the number of particles or faults on the basis of comparison of the output of the frequency filter with a certain threshold for discrimination of a foreign particle or fault; and at 806 is a computer for memorizing and/or displaying the number of particles or faults or the positions of them on the surface 21.

From equation (6), the AC component 807 and the DC component 808 of the beat signal detected by the detector 29 can be expressed as follows:

$$AC\ comp.=2\alpha Ep\Delta E_1 p\cdot \cos(\Delta\omega t+\theta'_2-\theta'_1) \quad (7)$$

$$DC\ comp.=(\alpha Ep)^2+\Delta E_1 p^2 \simeq (\Delta Ep)^2 \quad (8)$$

From equation (7), it is seen that the amplitude of the AC component of the beat signal is proportional to the intensity of the zero-th order diffraction light and the back scattered light from a particle or fault.

When the surface 21 is scanned with the scanning spot 20, there is a possibility that the intensity of the zero-th order diffraction light changes due to the effect of the circuit pattern or the like. From equation (8), such a change can be given by detecting the DC component. Therefore, in order to assure measurement of good S/N ratio without being affected by this effect, correction is made on the basis of monitoring the DC component of the beat signal represented in equation (8) through the zero-th order diffraction light monitor 803. A change in intensity of the zero-th order diffraction light 23 can be corrected, for example, by changing the amplification rate to the frequency-filtered signal in accordance with the correction signal 809. This assures that the intensity of the output pulse of the frequency filter 804 is correctly in a proportional relationship only with the intensity of scattered light from a foreign particle. Then, with respect to the noise level, a threshold is set in the counter 805 and discrimination is made as to whether the output pulse results from a foreign particle or fault, or it is a noise resulting from a circuit pattern or the like. The result of discrimination is inputted to the computer 806, wherein it is processed for data storing or displaying.

Figure 6:
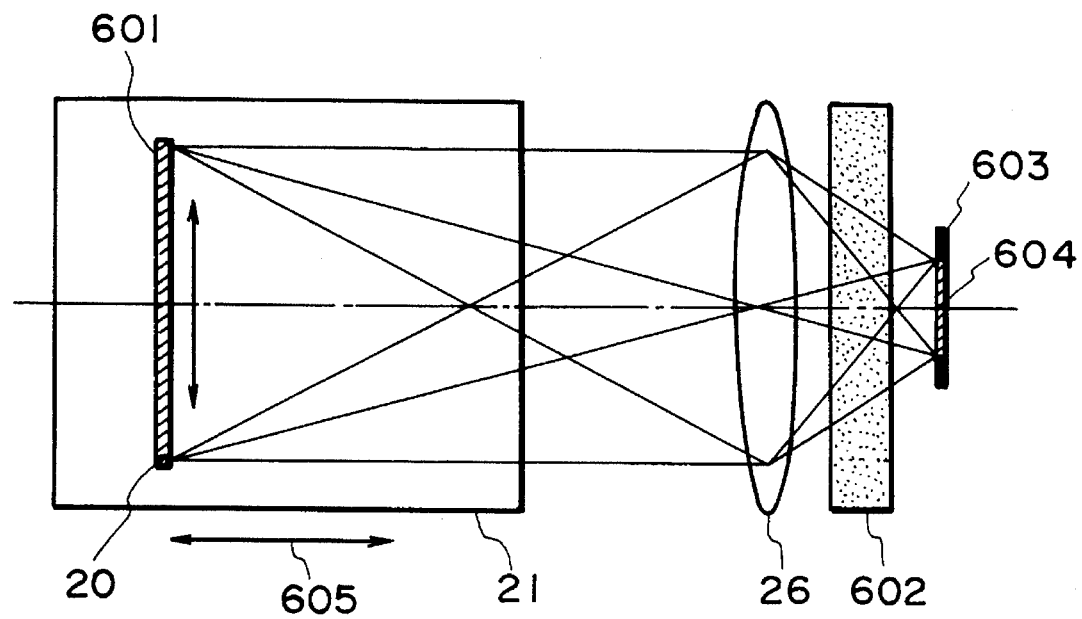
FIG. 6 is a schematic view of a detection optical system of this embodiment.

Now, the optical arrangement of the detection system of the present embodiment will be explained in greater detail. FIG. 6 shows the detection system of FIG. 1, as viewed from above. Denoted in the drawing at 601 is the optical scanning region which is the region to be scanned with the scanning spot 20 through the scanning mirror; at 602 is a filter system which includes the polarization filter 27 and the aperture 28 of FIG. 1, for example; at 603 is the detection surface of the photoelectric detector; at 604 is the imagewise region of the optical scanning region 601 as imaged by the lens system 26; and at 605 is the direction of scan as determined by the scanning stage system.

With this structure, even when the scanning spot 20 is at any location within the optical scanning region 601, the zero-th order diffraction light (23) in FIG. 1 as well as the scattered light (24, 25) can be received by the lens system 26 and, after interception of any stray light or unwanted S-polarized light components by the filter system 602, they can be projected on the detection surface 603 of the photoelectric detector. Thus, the structure that enables, in a scanning optical system using a scanning mirror or the like, the beat signal detection based on the optical heterodyne method is assured.

Figure 7:
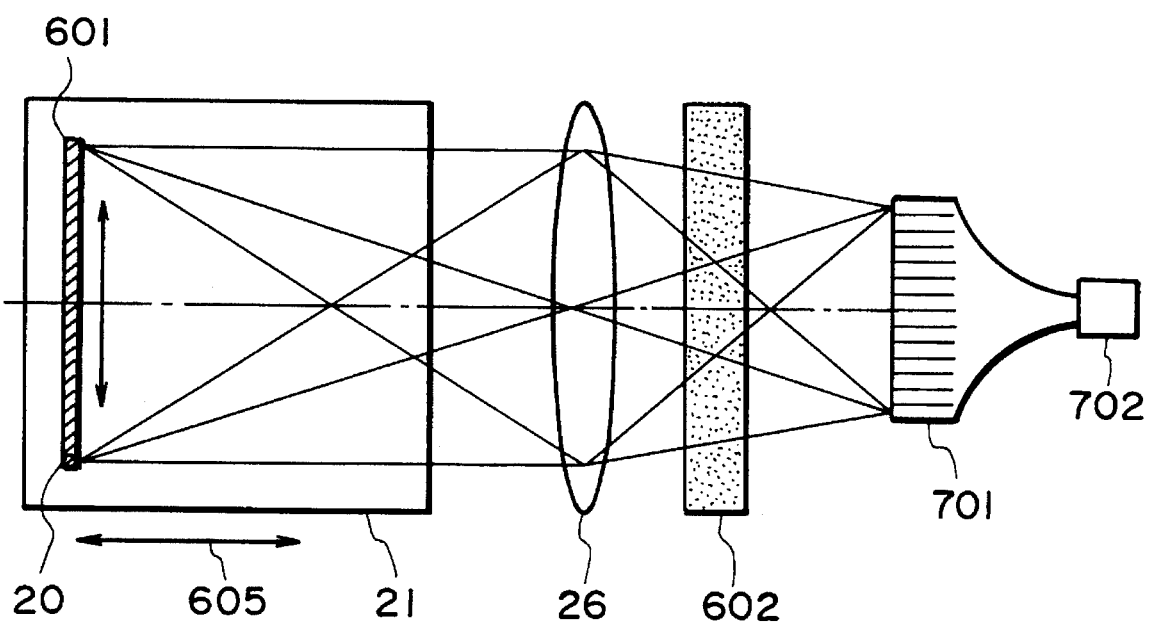
FIG. 7 is a schematic view of a modified form of the detection optical system.

A modified form is illustrated in FIG. 7 wherein a bundle of optical fibers 701 is disposed at the position of the detection surface, for guiding the light to a detection surface of a photoelectric detector 702. Also, this arrangement assures detection of a beat signal in the optical scanning region 601.

With the embodiment described hereinbefore, the following advantageous effects are provided:

(1) Only the light depolarized by a particle or fault to be detected, produces a beat signal. Any scattered light from a circuit pattern does not substantially participate in producing a beat signal. Therefore, the particle or fault can be detected with good S/N ratio.

(2) Because the heterodyne method is used, a higher S/N ratio is attainable as compared with a case wherein the intensity of weak scattered light from a particle is to be measured directly.

(3) Optical scanning through a scanning mirror ensures heterodyne detection, and a large increase of throughput is attainable.

(4) It is possible to detect a very small particle of a size of 0.3 micron or less with good sensitivity (which particle cannot be easily detected with the conventional technique), while discriminating it from a circuit pattern.

Embodiment 2

Figure 8:
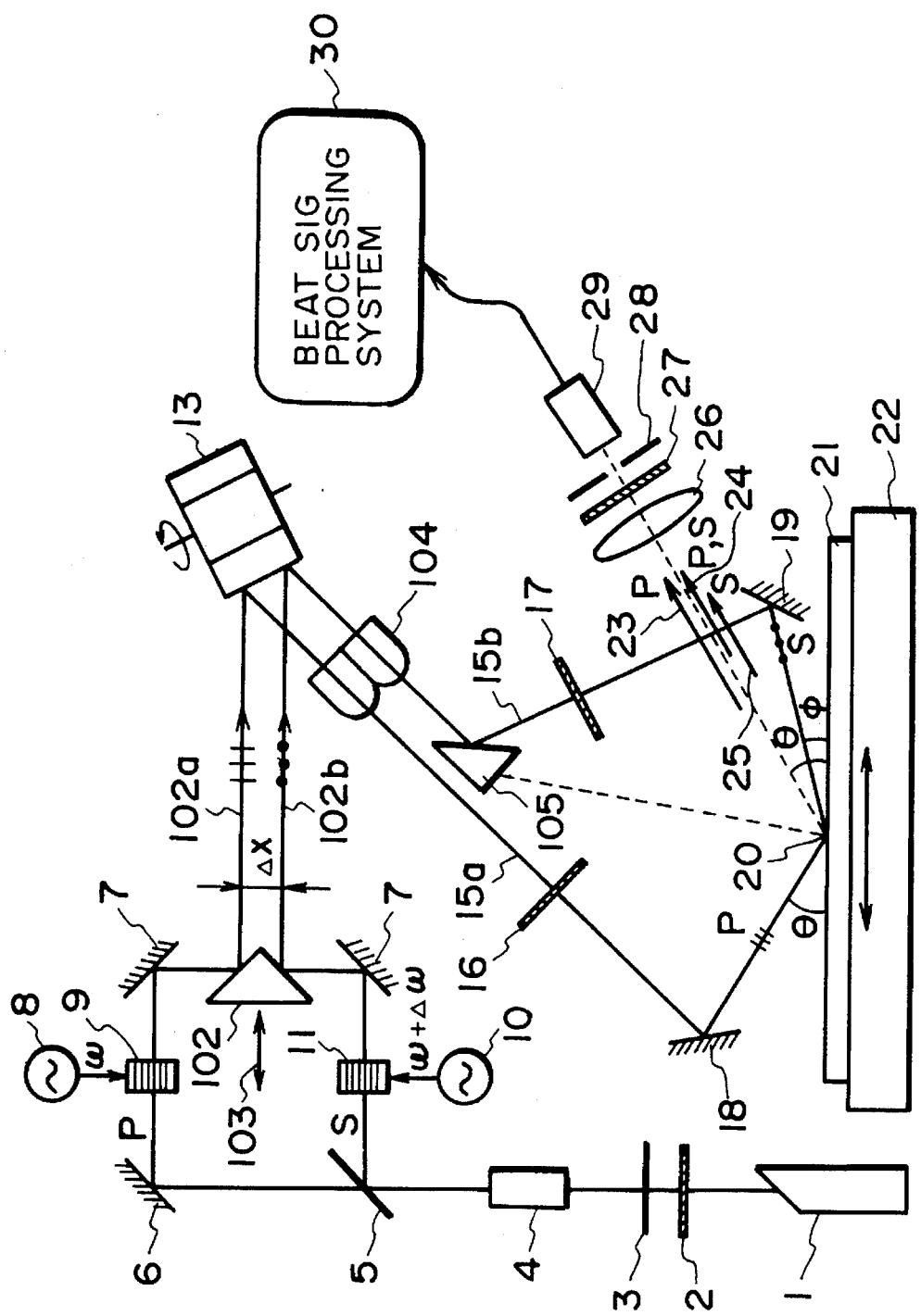
FIG. 8 is a schematic view of a second embodiment of the present invention.

Now, a second embodiment of the present invention will be explained. FIG. 8 shows this embodiment, and like numerals as those used in FIG. 1 are assigned to corresponding or similar elements. Description will be made mainly of the differences of this embodiment from the preceding embodiment.

Denoted in the drawing at 102 is a rectangular prism for applying two laser beams to a scanning mirror 13 in the form of spatially separated parallel light beams; denoted at 104 is an f-θ lens system; and at 105 is a mirror edge for directing the parallel light beams in different directions.

The structure for providing two laser beams having different frequencies and different directions of polarization, that is, a P-polarized laser beam modulated by an acousto-optic device 9 at a shift frequency ω and an S-polarized laser beam modulated by an acousto-optic device 11 at a shift frequency ω+Δω, is substantially the same as that of the preceding embodiment. As described hereinbefore, as a modification, only one acousto-optic device may be used to modulate only one of the two laser beams at a shift frequency Δω, or a Zeeman laser may be used. As a further alternative, an injection current to a semiconductor laser may be modulated.

In this embodiment, the two modulated, linearly polarized laser beams are not superposed one upon another but, by using the mirror 7 and the rectangular prism 102, parallel laser beams 102a and 102b spaced by a distance Δx are produced. These laser beams 102a and 102b comprise two linearly polarized lights having mutually orthogonal planes of polarization and having a relative shift frequency difference Δω. The spacing Δx of these parallel light beams can be easily adjusted to a desired one by moving the rectangular prism 102 in the direction of an arrow 103.

The two laser beams 102a and 102b are directed to a scanning optical system provided by the scanning mirror 13 and the f-θ lens system 104. Here, the f-θ lens system 104 comprises two combined f-θ lenses having the same optical function. Of the parallel light beams emanating from the f-θ lens system 104, one goes straight while the other is deflected by the edge mirror 105, whereby they are separated into a P-polarized laser beam 15a (shift frequency ω) and an S-polarized laser beam 15b (shift frequency ω+Δω) advancing in different directions. The structure and function of the remaining portions are essentially the same as those of the first embodiment, and description of them will be omitted here.

In the present embodiment, the zero-th order diffraction light 23 comprising P-polarized light is used as a reference light and it is caused to interfere (heterodyne interference) with the P-polarized light resulting from depolarization, to thereby obtain a beat signal. However, even if the relationship of the P-polarization and the S-polarization is interchanged totally, the detection can be done in a similar way. An example of doing this may be that: the characteristics of the polarization beam splitter 5 are changed so as to provide a laser beam 102a (15a) of an S-polarized component and a laser beam 102b (15b) of a P-polarized component while, on the other hand, a polarization filter 27 having a property for passing only S-polarized light components is used.

With the structure of the present embodiment wherein the edge mirror 105 is used to spatially separate the P-polarized laser beam 15a and the S-polarized laser beam 15b, it is possible to provide spatially separated, linearly polarized laser beams having different shift frequencies, without using an elongated polarization beam splitter. Generally, it is not easy and requires a high cost to prepare an elongated polarization beam splitter having a uniform light extinction ratio. Thus, with the present embodiment, in addition to the advantageous effects of the first embodiment, it is possible to facilitate the reduction of cost. Also, the mixture of unwanted polarized light during the scan can be avoided (i.e. a higher extinction ratio is attainable), and thus further enhancement of S/N ratio is assured.

Embodiment 3

Figure 9:
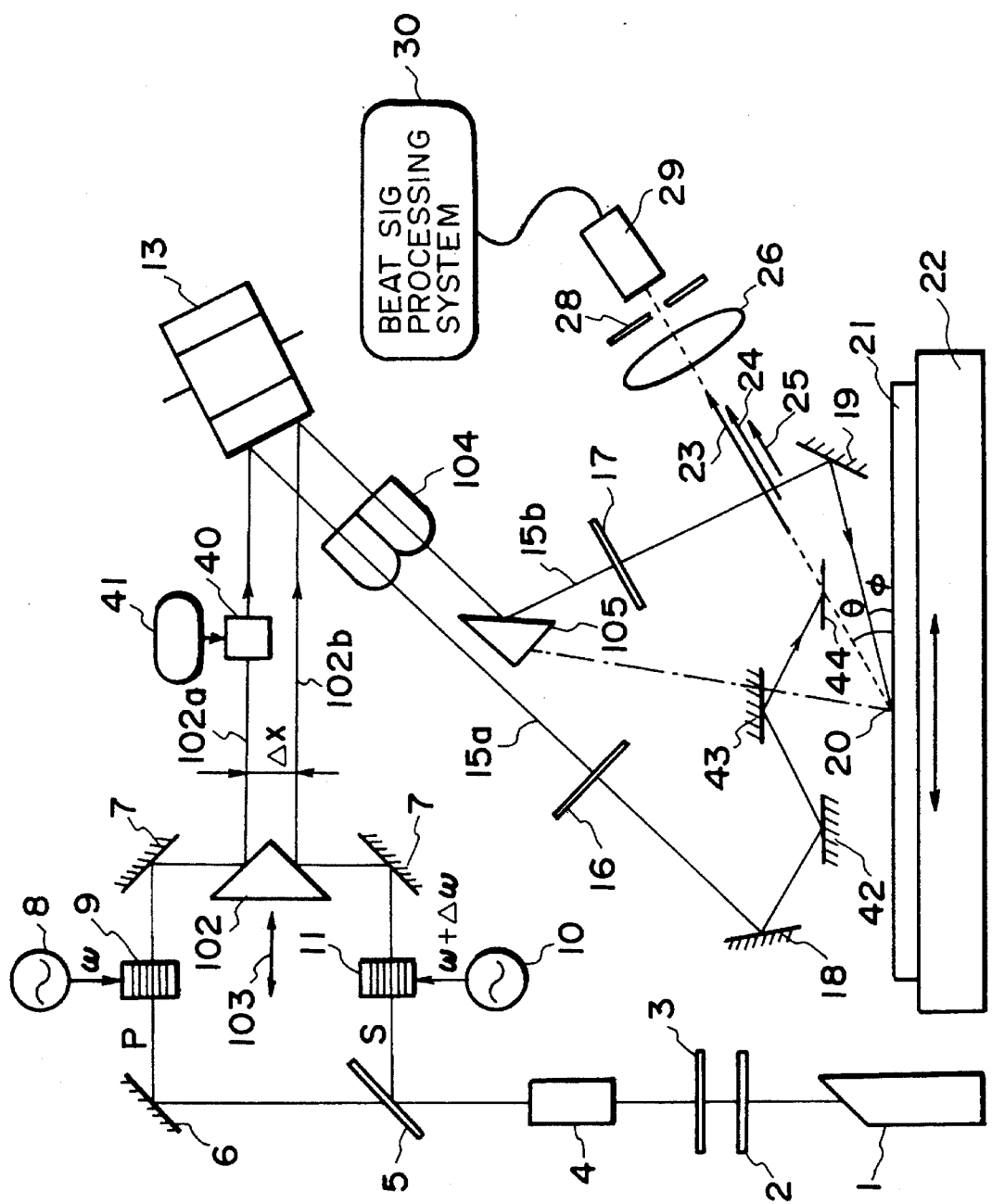
FIG. 9 is a schematic view of a third embodiment of the present invention.

FIG. 9 shows a third embodiment of the present invention. Like numerals as those of FIG. 8 are assigned to corresponding elements. Denoted at 40 is a polarization direction adjusting means which serves to set a desired polarization direction to the laser beam 102a. Denoted at 41 is a driver for driving the adjusting means 40. Denoted at 42 and 43 are mirrors, and denoted at 44 is a wave combining means such as a half mirror, for example.

Of the two laser beams 102a and 102b having different frequencies and different directions of polarization, the beam 102a has a direction of polarization which is in the P-polarized state and this polarization direction can be adjusted as desired by the adjusting means 40. That is, the direction of polarization of the beam 102a which serves as a reference light may be so set that the beam 102a best heterodyne-interferes with scattered light from a particle, to be described later. As a practical example of such adjusting means 40, there is a method wherein, by passing the light through a quarter wave plate, the light is transformed into a circularly polarized light and, after this, a polarizer such as a polarization filter is rotated into a desired direction. Alternatively, a light polarizing means such as a Faraday cell may be used.

The laser beam 15a having its direction of polarization being set is directed by the mirrors 18, 42 and 43 and it enters the wave combining means 44 as a reference light. On the other hand, the laser beam 15b is projected by the mirror 19 upon the surface 21 to be inspected, at an angle φ, to form a spot 20 thereon.

Scattered light from a particle or scattered light from a circuit pattern, within this spot 20, is combined by the wave combining means 40 with the reference light. By means of a lens system 26 disposed in the direction of an angle θ, the reference light 23 and scattered light 24 from a particle or fault as well as scattered light 25 from a circuit pattern are collected.

Here, of these scattered lights, the one that heterodyne-interferes with the reference light 23 to produce a beat signal is the scattered light 24 from a particle, having a direction of polarization registered with the reference light 23. The scattered light 25 from the circuit pattern does not heterodyne-interfere with the reference light. In this embodiment, the provision of a polarizing element such as a polarization filter before the photoelectric detector 29 is not always necessary and, therefore, it is omitted.

Now, the reason why scattered light from a circuit pattern does not heterodyne-interfere with the reference light will be explained in detail, in conjunction with FIG. 10. FIG. 10 is a schematic view, schematically showing the directions of polarization of scattered light from a particle and scattered light from a circuit pattern, caused by a spot 20, as well as the direction of polarization of the reference light. In the drawing, broken-line arrows 1011 depict the directions of polarization of scattered rays from a circuit pattern. Thin-line arrows 1012 depict the directions of polarization of scattered rays from a particle. Thick-line arrow 1013 depicts the direction of polarization of the reference light, set by the adjusting means 40.

When the spot 20 impinges on the circuit pattern area, scattered light from a circuit pattern as collected by a lens system has polarization components approximately in a particular direction, such as depicted by arrows 1011. On the other hand, scattered light from a particle has polarization components non-uniformly distributed in omni-directions such as depicted by arrows 1012, but it has a small directivity. In this embodiment, through the adjustment by the adjusting means 40, the direction of polarization of the reference light as depicted by arrow 1013 is adjusted to be registered with this "directivity", namely, the direction of polarization in which the scattered light from a particle has a highest intensity component, by which a highest interference signal is assured.

On this occasion, however, there is a possibility that the direction of polarization (1013) of the reference light coincides with the direction of polarization (1011) of the scattered light from a circuit pattern. Also, even in a case where the directions 1011 and 1013 are not coincident, if a small depolarization is caused by a circuit pattern, there is still a slight coincidence between them.

However, even if there is scattered light from a circuit pattern coincident with the direction of polarization of the reference light, they do not substantially interfere with each other. This will be explained with reference to FIG. 11. FIG. 11 is a schematic view, explaining the difference in wave fronts between scattered light from a particle and scattered light from a circuit pattern. In the drawing, denoted at 1021 is an input polarized laser beam; denoted at 1022 is a circuit pattern formed on the surface 21 to be inspected; denoted at 1023 is a particle on the surface 21; denoted at 1024 are scattered rays from the circuit pattern; and denoted at 1025 are scattered rays from the particle.

As the laser beam 1021 is projected in a plane wave upon the surface 21 to form a spot 20 thereon, since the scattered light 1024 from the circuit pattern 1022 is irregularly reflected by edges of pattern elements, the detected wave has a disturbed phase. On the other hand, since the particle 1023 is very small (e.g. of a size of 0.3 micron), the scattered light 1025 from the particle 1023 has a wave which is quite analogous to a spherical wave from a point light source.

As a consequence, as these scattered lights are combined with the reference light, the scattered light 1024 from the circuit pattern 1022 does not interfere with the reference light, upon the detection surface of the photoelectric detector in the one-color condition, and thus it provides a DC component. On the other hand, the scattered light from the particle 1023 interferes with the reference light in the one-color condition, and it produces a beat signal. Thus, an AC component is detected. For this reason, even if the direction of polarization of scattered light from a circuit pattern coincides with the reference light, they do not substantially interfere with each other and, thus, only scattered light from a particle can be detected with good precision. This feature is not peculiar to the present embodiment, but it commonly applies to the embodiments described hereinbefore or to some embodiments to be described later.

In the embodiment described above, polarized light adjusting means is used to adjust and set the direction of polarization of a reference light so that the reference light best interferes with scattered light from a particle and, by doing so, high detection precision is assured. Also, since high detection precision is attainable without the necessity of providing a polarizing element such as a polarization filter before a photoelectric detector, the structure can be made simpler.

Embodiment 4

Figure 12:
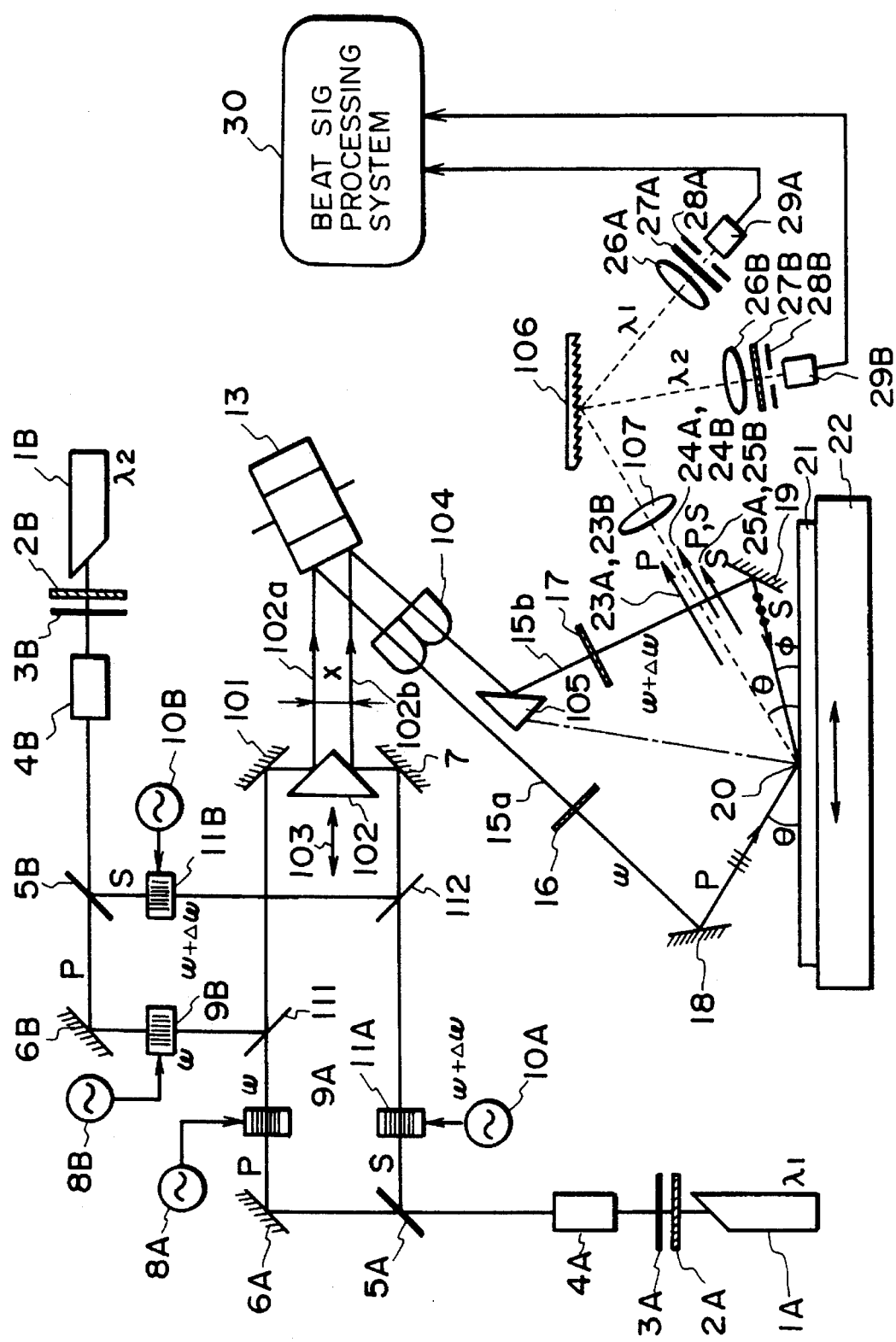
FIG. 12 is a schematic view of a fourth embodiment of the present invention.

Referring now to FIG. 12, a fourth embodiment which may correspond to an improved form of the second embodiment, will be explained. Like numerals as of those of the preceding embodiments are assigned to corresponding or similar elements. Denoted in the drawing at 1A and 1B are laser light sources for producing laser beams of different wavelengths $\lambda_1$ and $\lambda_2$, respectively. Specifically, the source 1A comprise an $Ar^+$ laser light source adapted to produce a laser beam of a wavelength $\lambda_1$=0.488 micron, while the source 1B comprises a He—Ne laser light source adapted to produce a laser beam of a wavelength $\lambda_2$=0.6328 micron. Denoted at 2A and 2B are polarizing plates; at 3A and 3B are filter systems; at 4A and 4B are collimator optical systems; at 5A and 5B are polarization beam splitters each for separating a laser beam into two mutually orthogonal, polarized components; at 9A, 9B, 11A and 11B are acousto-optic devices each for modulating a laser beam at an appropriate shift frequency; and at 111 and 112 are half mirrors each for combining light beams of wavelengths $\lambda_1$ and $\lambda_2$. Denoted at 106 is a spectroscope which uses a diffraction grating, for example; at 26A and 26B are lens systems each for guiding scattered light from a scanning spot 20 to a photoelectric detector; at 27A and 27B are polarization filters; at 28A and 28B are slit-like apertures; at 29A and 29B are photoelectric detectors; and at 30 is a beat signal processing system.

The laser beam 102a obtainable through the optical arrangement of this embodiment, corresponds to a combination of P-polarized light of a wavelength $\lambda_1$ and P-polarized light of a wavelength $\lambda_2$ as modulated respectively at a shift frequency $\omega$ and combined by means of the half mirror 111. On the other hand, the laser beam 102b corresponds to a combination of S-polarized light of a wavelength $\lambda_1$ and S-polarized light of a wavelength $\lambda_2$ as modulated respectively at a shift frequency $\omega+\Delta\omega$ and combined by means of the half mirror 112. After being scanned by the scanning optical system, these laser beams are separated by the edge mirror 105 into a P-polarized laser beam 15a (wavelengths $\lambda_1$ and $\lambda_2$) and an S-polarized laser beam 15b (wavelengths $\lambda_1$ and $\lambda_2$), and they are converged into the same spot 20 with different angles of incidence.

In the present embodiment, particular notice is taken of the following six kinds of lights, among those emitting from the scanning spot 20 toward the detection optical system:

(1) Zero-th order diffraction light 23A (P-polarized light; wavelength $\lambda_1$) of the P-polarized laser beam 15a;

(2) Zero-th order diffraction light 23B (P-polarized light; wavelength $\lambda_2$) of the P-polarized laser beam 15a;

(3) Backward scattered light 24A (P-polarized light plus S-polarized light; wavelength $\lambda_1$) resulting from a foreign particle or fault;

(4) Backward scattered light 24B (P-polarized light plus S-polarized light; wavelength $\lambda_2$) resulting from a foreign particle or fault;

(5) Backward scattered light 25A (S-polarized light; wavelength $\lambda_1$) resulting from a circuit pattern; and (6) Backward scattered light 25B (S-polarized light; wavelength $\lambda_2$) resulting from a circuit pattern.

In the present embodiment, the light received by a relay optical system 107 is separated by the spectroscope 106 comprising a diffraction grating, into two components of wavelengths $\lambda_1$ and $\lambda_2$, and these components are then detected separately. This assures that, for each of the two wavelengths $\lambda_1$ and $\lambda_2$, a beat signal attributable to a foreign particle or fault can be detected. The beat signal processing system 30 operates to process two signals in a similar way and, if a foreign particle or fault is detected with respect to at least one of them, then it is discriminated that there is a foreign particle or fault.

Figure 13A:
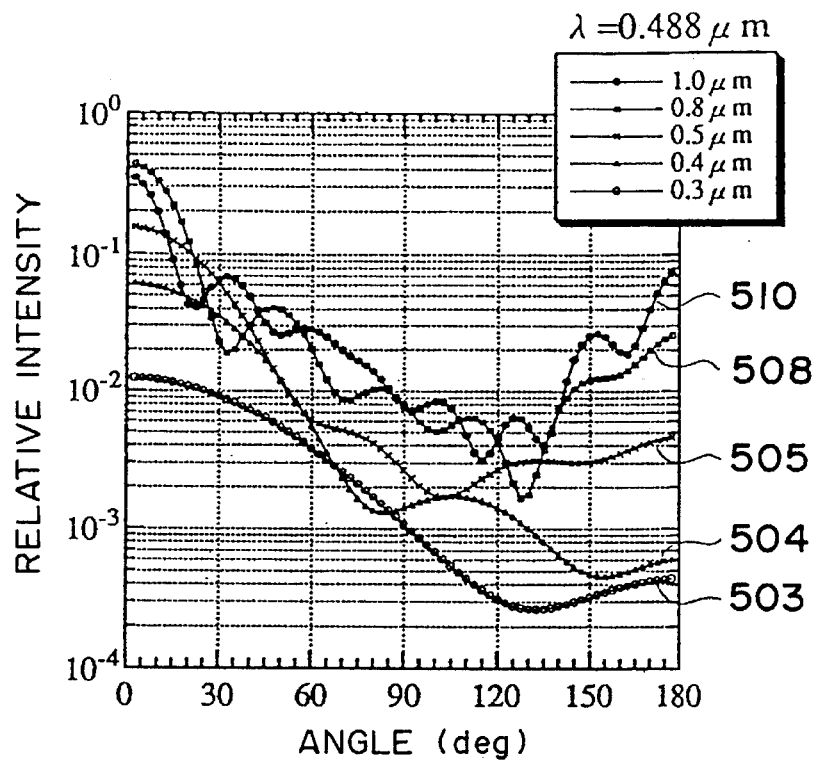
FIGS. 13A and 13B are graphs each showing the relationship between the relative intensity of scattering and the angle of scattering in particulate size.
Figure 13B:
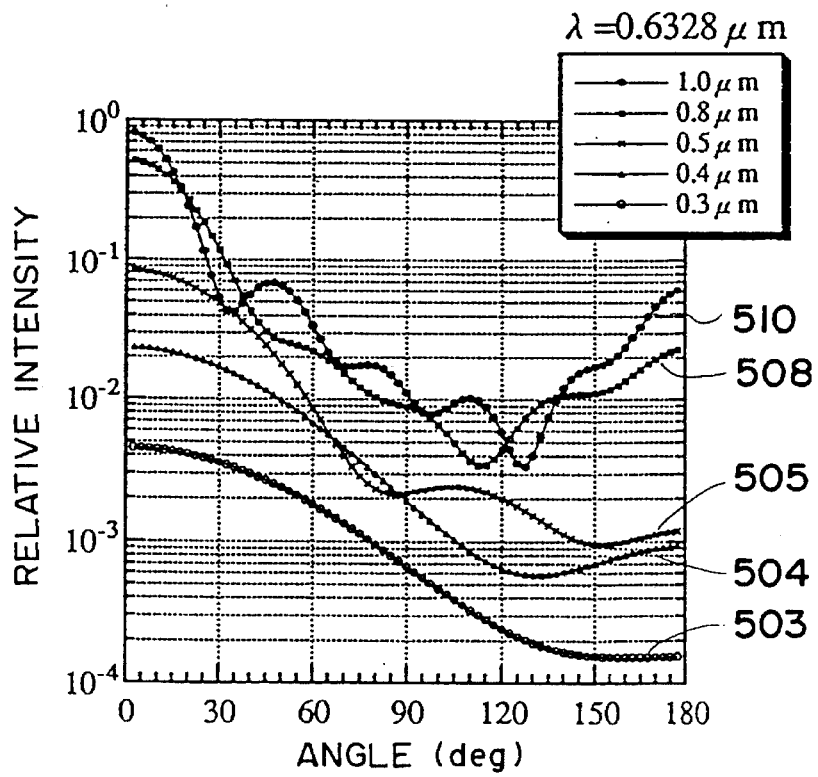

Here, advantageous effects of the present embodiment wherein laser beams of different wavelengths $\lambda_1$ and $\lambda_2$ are used and beat signal detection is made for each wavelength, will be explained. FIGS. 13A and 13B each shows an intensity distribution of light scattered by a particle as determined in accordance with the Mie scattering theory. The graph of FIG. 13A corresponds to a case where the wavelength of input light is 0.488 micron ($Ar^+$ laser), and the graph of FIG. 13B corresponds to a case where the wavelength of input light is 0.6328 micron (He—Ne laser). The axis of the abscissa in each graph corresponds to the direction of propagation of the scattered light, and the direction of advancement of the light impinging on the particulate is represented by 0 (zero) deg. while the direction opposite to it is represented by 180 deg. Namely, 0 (zero) deg. represents the direction of forward scattering while 180 deg. represents the direction of back scattering. On the other hand, the axis of the ordinate of each graph corresponds to the relative intensity of light at a certain angle of scattering. Curves 503, 504, 505, 508 and 510 in each graph provide the scattering distribution curves as defined in cases where the diameter of the particulate is 0.3 micron, 0.4 micron, 0.5 micron, 0.8 micron and 1.0 micron, respectively.

It is to be noted here that each scattering intensity distribution curve in FIGS. 13A and 13B is determined when a plane wave is projected to a particulate floating in space and, therefore, in an exact sense it cannot be applied to a foreign particle adhered to the surface being examined. However, where the input light is obliquely incident and back scattered light is detected as in the present embodiment, because of small back scattering of light from the surface being examined it may be relied upon as a qualitative explanation.

From the graphs of FIGS. 13A and 13B, it is seen that, if the wavelength of light impinging on one and the same particulate changes, the light intensity at a certain scattering angle changes. For example, regarding the back scattered light and the angle of scattering of 150 deg., the light of wavelength 0.488 micron has a larger scattered light intensity for the cases of the particulate diameters of 0.3 micron and 0.5 micron. However, to the contrary, for the particulate diameter of 0.4 micron, the light of wavelength 0.6328 micron has a larger scattered light intensity.

In the present embodiment, any foreign particle or fault is detected with the two parameters obtained respectively from these wavelengths and, thus, "manifold" measurement is executed. Therefore, it is possible to complement, with one of the two wavelengths, such a particle diameter region to which the other wavelength has a lower sensitivity. As a result, the measurement can meet particles of a variety of sizes. In other words, the present embodiment provides advantages of reduced sensitivity variation to the particle size and widened dynamic range to the particle size for inspection.

While in the present embodiment two different wavelengths $\lambda_1$ and $\lambda_2$ are used to obtain two parameters for attainment of "manifold" measurement, three or more wavelengths may of course be used. This ensures further enhancement of measurement precision.

Now, the optical arrangement of the detection system of the present embodiment will be explained in greater detail. FIG. 14 shows the detection system of FIG. 12, as viewed from above. Denoted in the drawing at 601 is the optical scanning region which is the region to be scanned with the scanning spot 20 through the scanning mirror; at 605 is the direction of scan as determined by the scanning stage system; at 610 is the imagewise region on the spectroscope 106 as imaged by the relay optical system 107; and at 620 is a reduction optical system including the lenses 26A and 26B in FIG. 12. Denoted at 602 is a filter system which includes the polarization filters 27A and 27B as well as the apertures 28A and 28B of FIG. 1, for example; at 603 is the detection surface of the photoelectric detector; at 604 is the imagewise region of the optical scanning region 601 as imaged by the lens system 26.

With this structure, even when the scanning spot 20 is at any location within the optical scanning region 601, the zero-th order diffraction light (23A, 23B) in FIG. 12 as well as the scattered light (24A, 24B, 25A, 25B) can be received by the relay lens 107 and imaged on the spectroscope 106. Then, the light from the spectroscope divided with respect to the spectrum is received by the reduction optical system 620 and, after interception of any stray light or unwanted S-polarized light components by the filter system 602, it is projected on the detection surface 603 of the photoelectric detector. Thus, the structure that enables, in a scanning optical system using a scanning mirror or the like, the beat signal detection based on the optical heterodyne method is assured.

FIG. 15 shows a modified form wherein the spectroscope comprising a diffraction grating is replaced by a half mirror. More specifically, denoted in the drawing at 108 is the half mirror; at 26A and 26B are reduction optical systems; at 37A and 37B are filter systems each comprising a wavelength selecting filter for selectively passing only a wavelength $\lambda_1$ or $\lambda_2$ and a polarization filter for blocking unwanted S-polarized components; at 28A and 28B are apertures; and at 29A and 29B are photoelectric detectors. The scattered light received by the relay optical system 107 is divided by the half mirror 108 into two, and light of a wavelength $\lambda_1$ is extracted by means of the filter system 37A while light of a wavelength $\lambda_2$ is extracted by means of the filter system 37B, whereby signals related to respective wavelengths can be produced.

With this embodiment of the present invention, owing to "manifold" measurement of a particle or fault using different wavelengths, the following advantageous effects are provided in addition to those of the second embodiment:

(1) The detection sensitivity variation to the particle size is small; and (2) The dynamic range to the particle size for inspection is wide.

Embodiment 5

Next, a fifth embodiment of the present invention will be explained. While in the fourth embodiment different wavelengths are used for "manifold" measurement, in this embodiment such "manifold" measurement is assured by using different scattering angle components.

Figure 16:
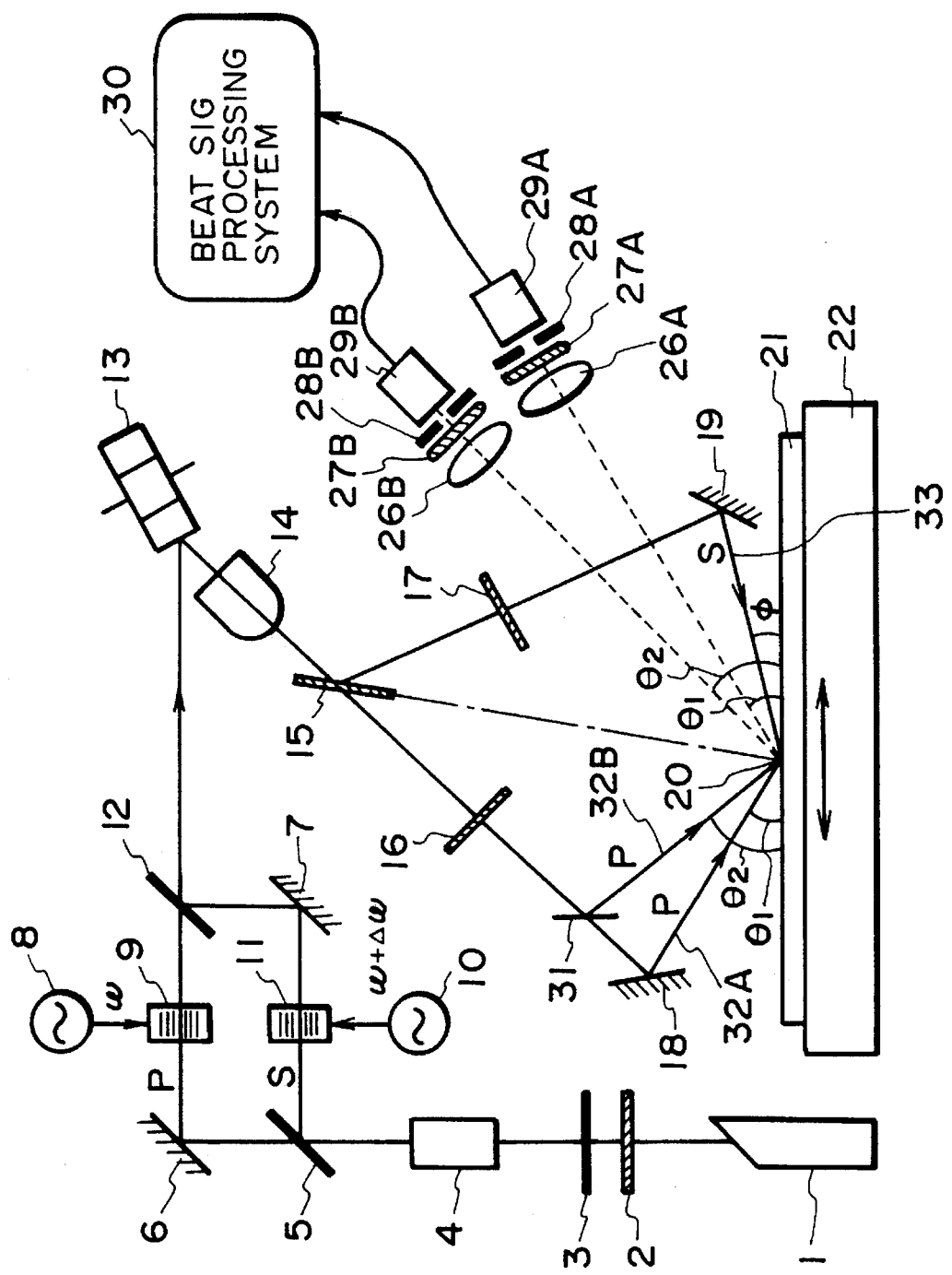
FIG. 16 is a schematic view of a fifth embodiment of the present invention.

FIG. 16 shows the arrangement of this embodiment. Like numerals as of those of FIG. 1 are assigned to corresponding or similar elements. In this embodiment, as compared with the structure of FIG. 1, a half mirror 31 is added to ensure that two beams 32A and 32B are projected on the same position of the light spot 20 at different angles $\theta_1$ and $\theta_2$. Disposed in the direction of zero-th order diffraction of the beam 32A is a first detection optical system (26A, 27A, 28A, 29A) while, on the other hand, disposed in the direction of zero-th order diffraction of the beam 32B is a second detection optical system (26B, 27B, 28B, 29B). Stating in a different way, the first and second detection systems are disposed in the directions of different back scattering angles, with respect to the S-polarized laser beam 33. Beat signal processing system 30 operates to process two signals, obtained through the first and second detection optical systems, in a similar manner as that in the preceding embodiments. If any foreign particle or fault is detected with respect to at least one of them, it is discriminated that there is a foreign particle or fault on the surface being examined.

As seen from the graphs of FIG. 13A and 13B, depending on the angle of scattering, different information is obtainable from the scattered light produced from the position being inspected. Thus, by detecting scattered components of different angles to ensure "manifold" measurement as in the present embodiment, it is possible to enhance the precision of detection. While in this embodiment scattered components in two directions are detected, those in three or more directions may of course be detected. This effectively assures further enhancement of the inspection precision.

Embodiment 6

Figure 17:
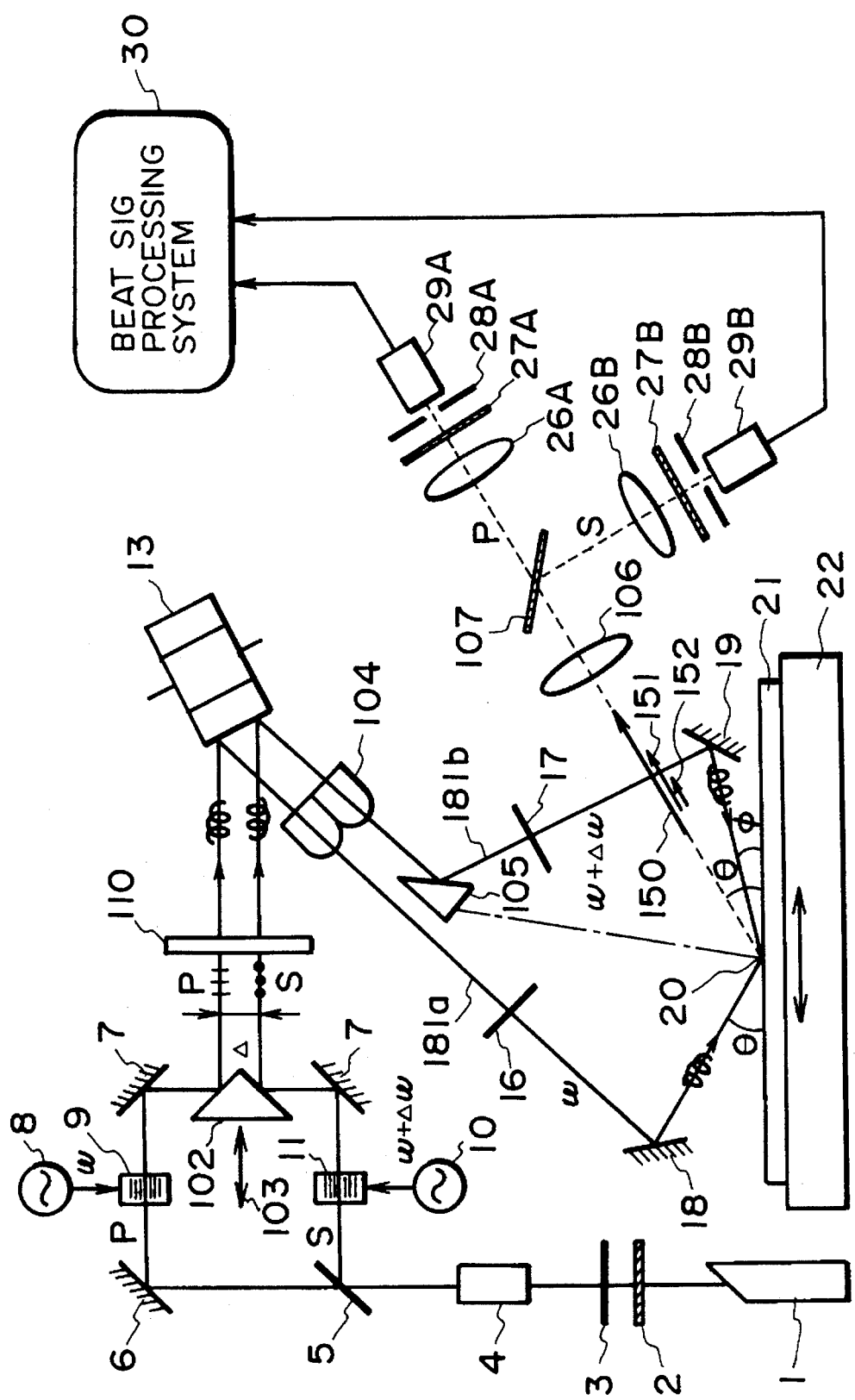
FIG. 17 is a schematic view of a sixth embodiment of the present invention.

FIG. 17 shows a sixth embodiment of the present invention, and like numerals as those used in FIG. 8 are assigned to corresponding or similar elements. While in the preceding embodiments lights in different states of linear polarization are used to cause heterodyne interference, in the present embodiment circularly polarized lights are used in place of them. An important structural feature of the present embodiment resides in the provision of a quarter ($\lambda/4$) phase difference plate 110 disposed between a rectangular mirror 102 and a scanning mirror 13, and a detection optical system including and following a polarization beam splitter 107.

In FIG. 17, the optical arrangement for providing two laser beams, one is P-polarized light with a shift frequency ω and the other is S-polarized light with a shift frequency ω+Δω, is of the same structure as that of the FIG. 8 embodiment. These two linearly polarized lights pass through the quarter phase plate 110, by which they are transformed into a circularly polarized beam with a shift frequency ω and a circularly polarized beam with a shift frequency ω+Δω. Here, these two circularly polarized lights are in an oppositely rotating relationship. Through the scanning optical system like that of the preceding embodiment, these light beams are directed to the surface to be inspected to scan the same.

In the present embodiment, particular notice is taken of the following three kinds of light, among the lights to be emitted from the scanning spot 20 toward the detection optical system:

(1) Zero-th order diffraction light 150 which is circularly polarized light (P component=S component);

(2) Back scattered light 151 from a particle or fault, which is elliptically polarized light (P component>S component); and (3) Back scattered light 152 from a circuit pattern, which is circularly polarized light (P component=S component).

These scattered lights 150, 151 and 152 are separated into a P-polarized component and an S-polarized component, by means of the polarization beam splitter 107. The P-polarized component is received by a detection optical system 26A, and anything therein other than the P-polarized component is completely removed by a polarization filter 27A, for reduction of any beat signal noise due to mixture of an unwanted polarization component. After this, it passes through a slit-like aperture 28A and is received by a photoelectric detector 29A, whereby it is photoelectrically converted. Similarly, the S-polarized component is received by a detection optical system 26B, and anything therein other than the S-polarized component is completely removed by a polarization filter 27B, for reduction of any beat signal noise. After this, it passes through a slit-like aperture 28B and it is photoelectrically converted by a photoelectric detector 29B. In this manner, a beat signal corresponding to the P-polarized component is obtainable from the detector 29A, while a beat signal corresponding to the S-polarized component is obtainable from the detector 29B.

The detection of any particle or fault in the present embodiment is based on the phenomenon that the back scattered light from the particle or fault has a larger P-polarized component as compared with an S-polarized component. More specifically, if there is a particle or fault, the beat signal corresponding to the P-polarized component becomes larger than that corresponding to the S-polarized component, and the beat signal processing system 30 carries out the discrimination on the basis of the detection signals from the detectors 29A and 29B. As an example, if the comparison of the amplitudes of the two beat signals turns out to be P>S, it is discriminated that there is a particle or fault. If P≈S is turned out, it is discriminated that there is no particle or fault.

Figure 18A:
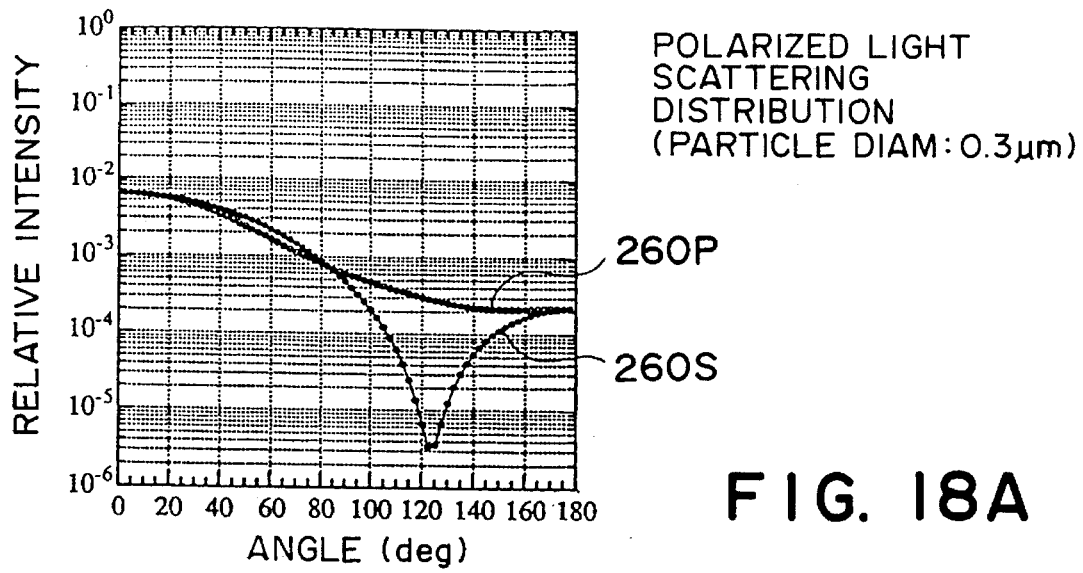
FIGS. 18A, 18B and 18C are graphs each showing the relationship between the relative intensity of scattering and the angle of scattering in a P-polarized component and an S-polarized component.
Figure 18B:
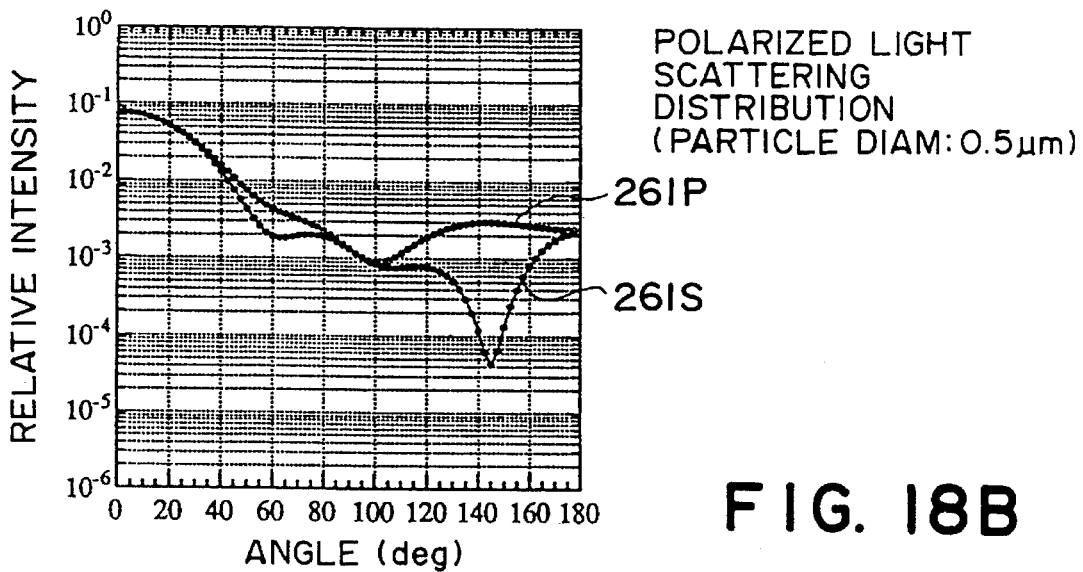
Figure 18C:
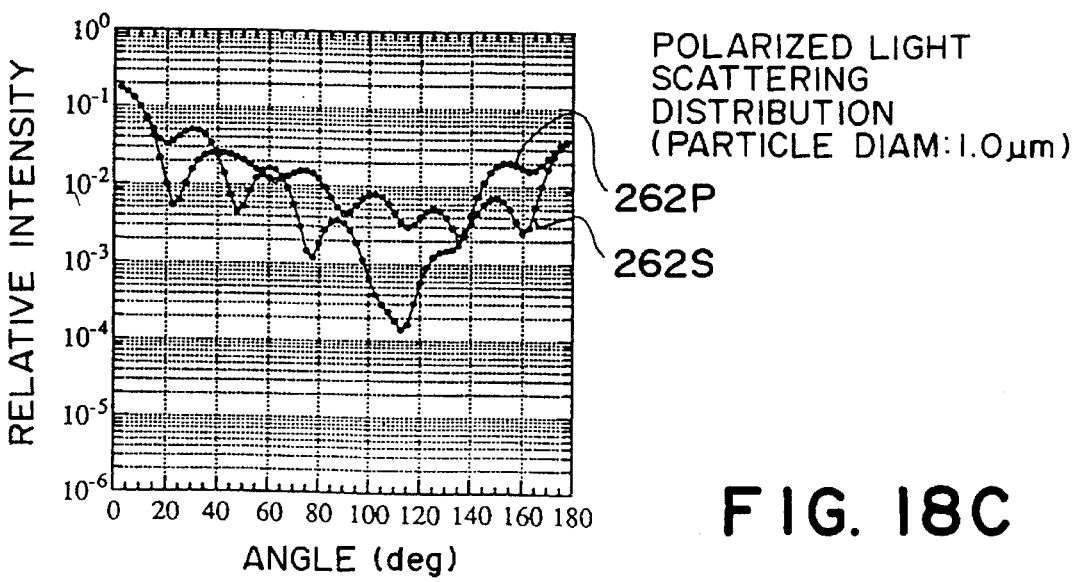

Referring now to the graphs of FIGS. 18A–18C, the reason why a larger P-polarized component is included in the back scattered light from a particle or fault will be explained. FIGS. 18A–18C are the graphs wherein, with respect to each of the P and S components, the intensity distribution of scattered light from a particulate as determined in accordance with the Mie scattering theory, is illustrated. More specifically, in FIGS. 18A–18C, there are illustrated curves of distributions of the P-polarized light scattering and the S-polarized light scattering in the cases of particulate diameters of 0.3 micron, 0.5 micron and 1.0 micron, respectively. The axis of abscissa in each graph denotes the direction of propagation of the scattered light, and the direction of advancement of the light inputted to the particulate is represented by 0 (zero) deg. while the direction opposite thereto is represented by 180 deg. Namely, the "zero deg." represents the direction of forward scattering while the "180 deg." represents the direction of back scattering. Reference characters 260p, 261p, and 261p denote curves of scattering distribution of the P-polarized light in the cases of particulate diameters of 0.3 micron, 0.5 micron and 1.0 micron, respectively. Similarly, reference characters 260s, 261s and 262s denote curves of scattering distribution of the S-polarized light in the cases of particulate diameters of 0.3 micron, 0.5 micron and 1.0 micron, respectively.

Now, the back scattered light (140–160 deg.) from a particulate will be considered. From the graph of FIG. 15A, it is seen that at the side of the back scattering the P-polarized component is larger than the S-polarized component. Also, in the graphs of FIG. 15B and 15C, at the side of the back scattering, the P-polarized component is larger than the S-polarized component. Generally, there occurs disturbance of polarization due to depolarization attributable to a particle or fault. However, the change from the P-polarization to the S-polarization and the change from the S-polarization to the P-polarization are approximately of the same magnitude. As a consequence, even by the depolarization attributable to the particle or fault, the superiority of the P-polarized component in the back scattered light is not affected. Thus, it can be appropriately said that, if there is a particle or fault, the P-polarized component of the back scattered light is relatively large.

In the present embodiment as described, while utilizing the phenomenon that in the scattering of light from a particle or fault the P-polarized component of the scattered light is relatively larger, beat signals corresponding to the P and S components are detected and mutually compared. This ensures detection of a particle or fault at a high S/N ratio even when scattered light from a circuit pattern is mixed.

Embodiment 7

Figure 19:
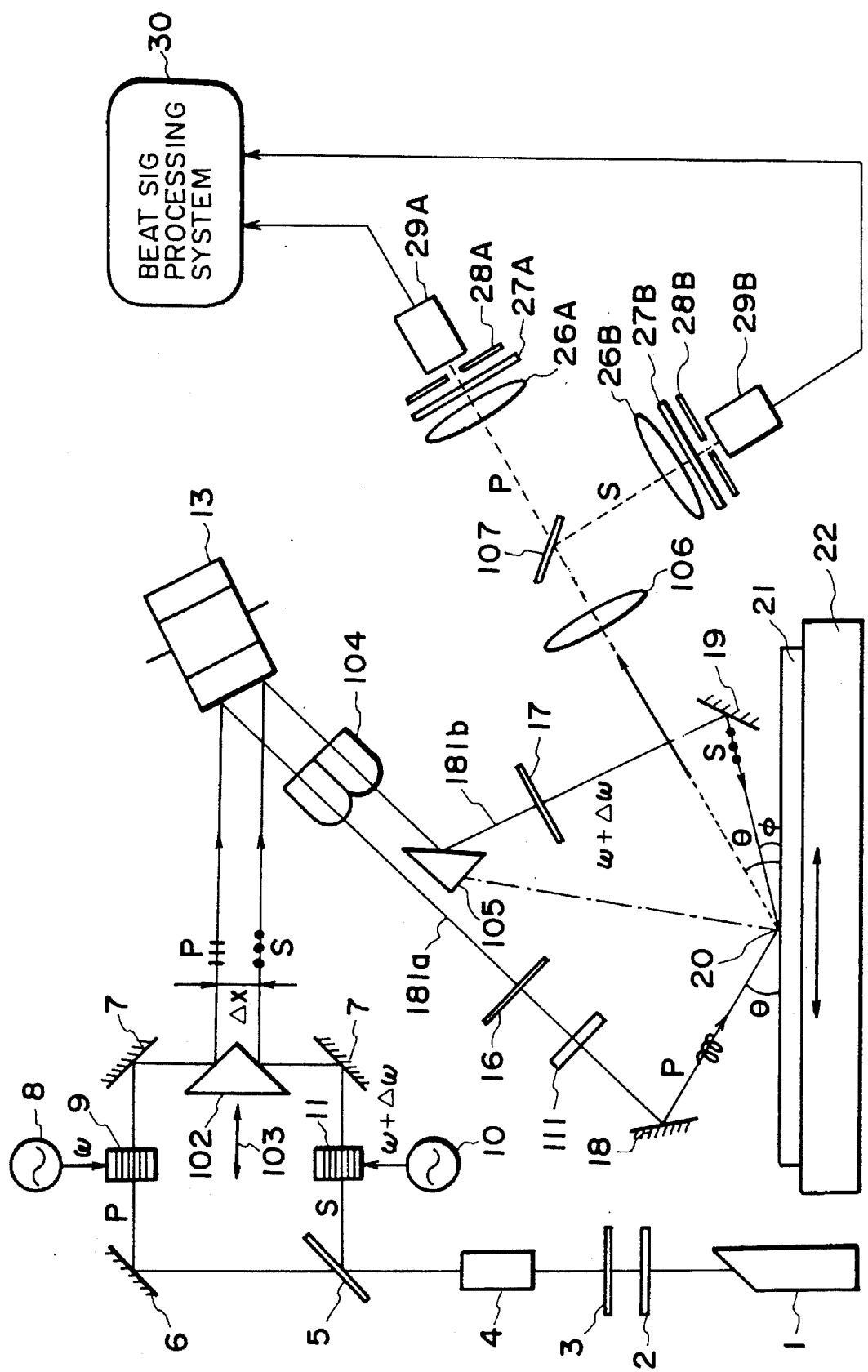
FIG. 19 is a schematic view of a seventh embodiment of the present invention.

Now, a seventh embodiment of the present invention will be explained with reference to FIG. 19. This embodiment has a feature that one of the lights impinging on the detection position comprises a circularly polarized light and the other comprises a linearly polarized light. The structure is analogous to that of the FIG. 17 example, and the same reference numerals are assigned to corresponding elements. As a feature of this embodiment, a quarter wave plate phase difference 111 is provided only in the path of reference light. With this arrangement, the light reflected by a mirror 18 and impinging on the detection position comprises a circularly polarized light, while the light reflected by a mirror 19 and impinging on the detection position comprises a linearly polarized beam (S-polarized light). It is to be noted here that the direction of polarization of the linearly polarized light is not limited to the S-polarization. It may be P-polarization or 45-deg. polarization. Alternatively, the relationship of the circularly polarized light and the linearly polarized light may be reverted.

Figure 20A:
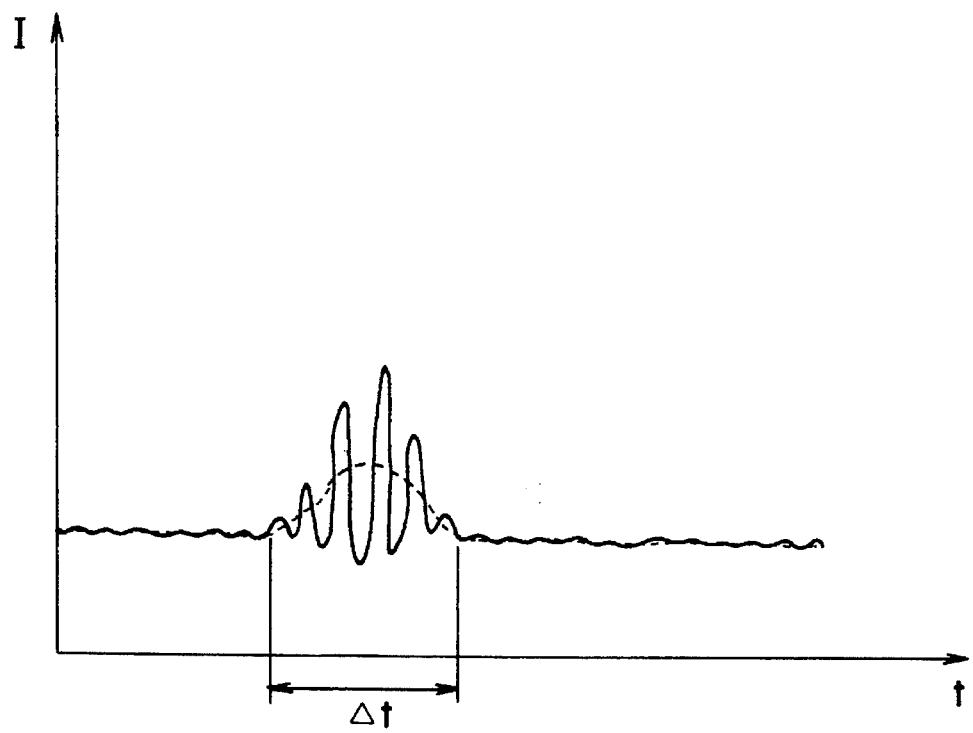
FIGS. 20A and 20B are graphs each showing an example of a waveform of a signal detectable in the seventh embodiment.
Figure 20B:
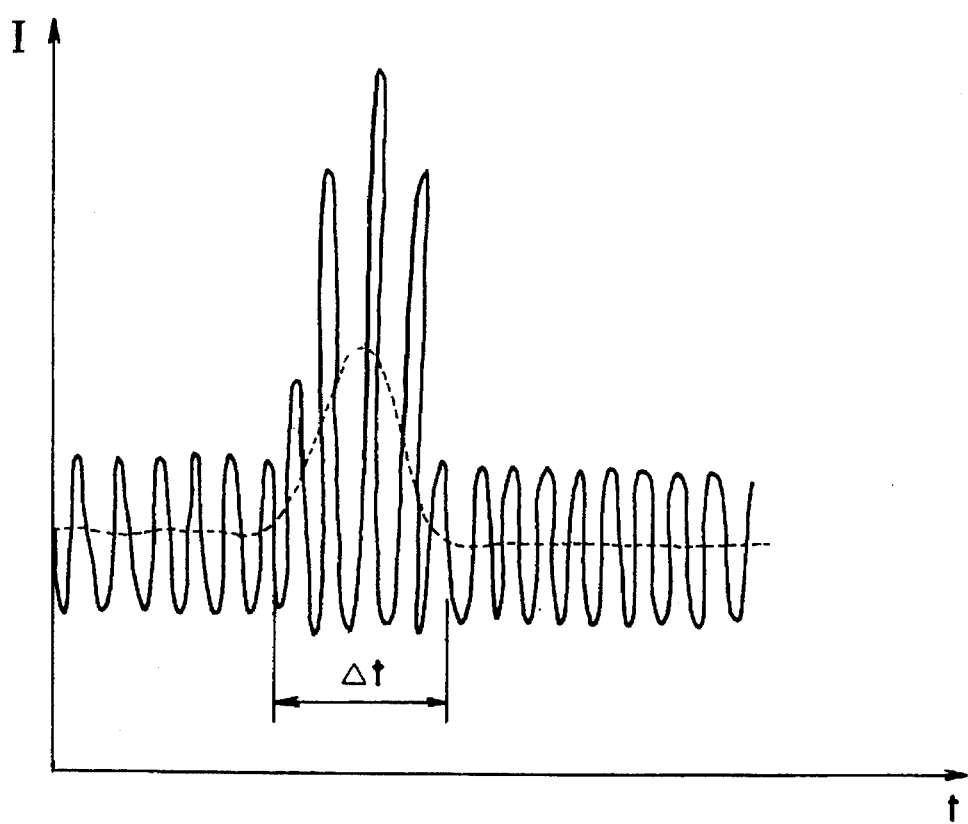

FIGS. 20A and 20B show examples of signal waveforms which may be produced by photoelectric detectors 29A and 29B. FIG. 20A shows an output waveform from the detector 29A, and FIG. 20B shows an output waveform from the detector 29B. If there is a particle, the levels of these signals increase. Then, by detecting the signal ratio of them, for example, through beat signal processing system 30, such a particle can be detected with good precision.

Embodiment 8

Figure 21:
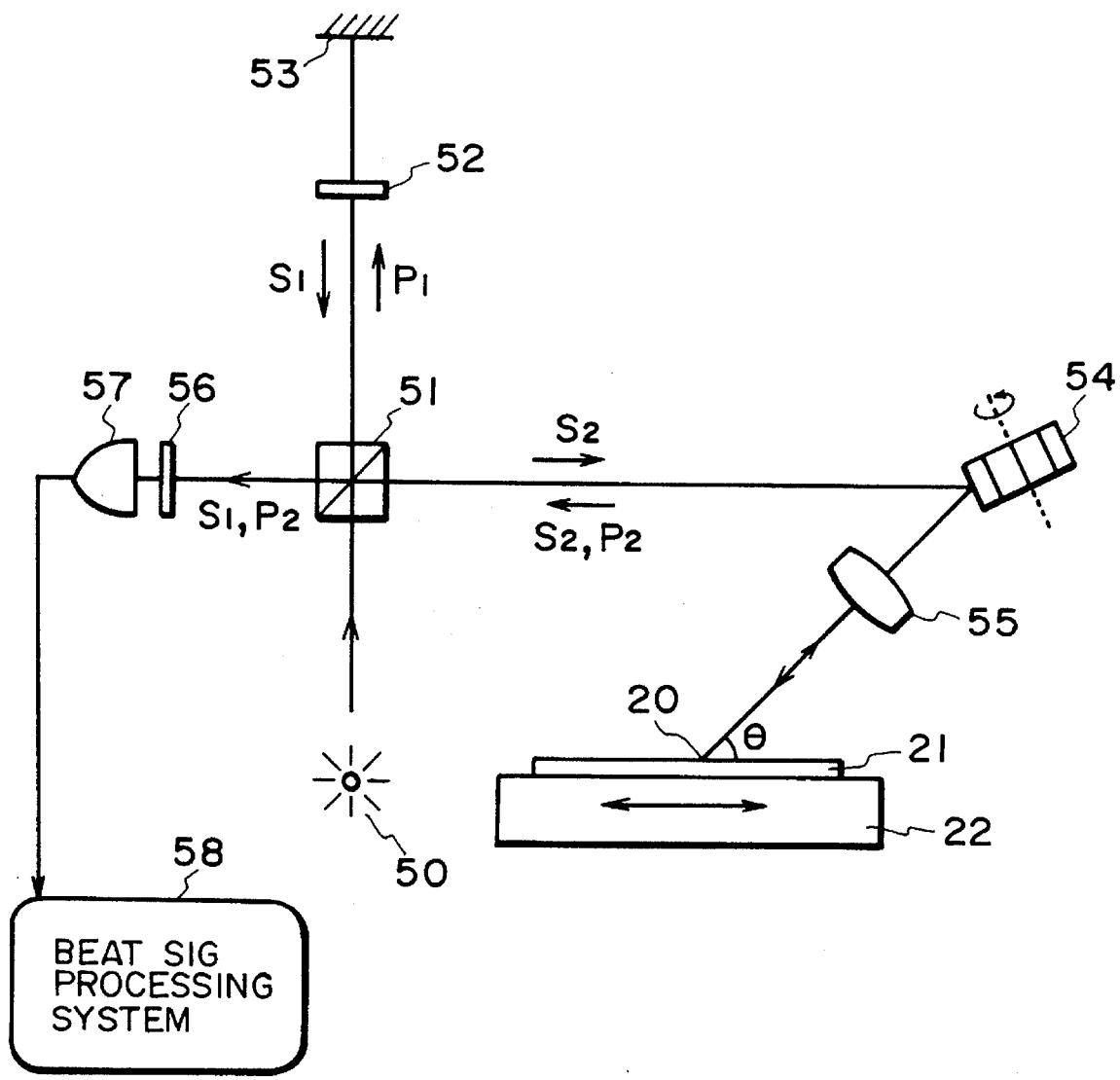
FIG. 21 is a schematic view of an eighth embodiment of the present invention.

Referring now to FIG. 21, an eighth embodiment of the present invention will be explained. Denoted in the drawing at 50 is a light source system; at 51 is a polarization beam splitter; at 52 is a quarter wave plate; at 53 is a reflection mirror; at 54 is a scanning mirror such as a polygonal mirror or galvano mirror; at 55 is an f-θ lens system; at 56 is a polarization filter; at 57 is a detection system including a photoelectric detector; and at 58 is a beat signal processing system.

The light source system 50 is adapted to provide a laser beam of two wavelengths having a small difference in frequency, in mutually orthogonal planes of polarization, and it comprises a Zeeman laser, for example. Of course, the light source system may have the structure as that of the preceding embodiment. The light from the light source system 50 is inputted to the polarization beam splitter 51. The P-polarized laser beam with a frequency $f_1$ passes through the beam splitter 51 while the S-polarized laser beam with a frequency $f_2$ is reflected by the beam splitter 51, whereby two frequency components are separated and two light beams are separated.

The P-polarized laser beam $P_1$ passed through the polarization beam splitter 51 then goes through the quarter wave plate 52 and it is reflected by the mirror 53 in an exactly reverse direction. The mirror 53 may desirably comprise a corner cube prism or a cat's eye reflector capable of returning a received light along a path on or parallel to to the oncoming path. The reflected light passes again the quarter wave plate 52 and enters the polarization beam splitter 51. Here, during the period from the exit from the polarization beam splitter 51 to the second incidence on the same beam splitter, the light passes through the quarter wave plate 52 twice. Thus, the P-polarized laser beam $P_1$ is transformed into an S-polarized laser beam $S_1$ whose plane of polarization is rotated by 90 deg. When this S-polarized laser beam with a frequency $f_1$ is incident on the beam splitter 51, since it is now S-polarized light, it is reflected thereby and is directed toward the detection system 57 as a reference light $S_1$.

On the other hand, the S-polarized light $S_2$ with a frequency $f_2$ inputted from the light source system 50 to the polarization beam splitter 51 and reflected thereby, is reflected by the scanning mirror 54 such as a polygonal mirror or a galvano mirror. Then, it goes through the f-θ lens 55 and it is projected onto the surface 21, to be inspected, at an angle of incidence of θ as a scanning spot 20, by which the surface can be scanned along a direction perpendicular to the sheet of the drawing. As regards the incidence angle θ, it is so selected as to provide a high sensitivity to scattered light. Since it is not necessary to project two light beams on the same point as in the preceding embodiment, there is a wide design latitude. The scanning stage 22 serves to move the surface 21 in a direction (depicted by an arrow) perpendicular to the aforementioned scanning direction, such that the surface 21 as a whole can be scanned two-dimensionally.

As described hereinbefore, if there is a particle or fault or a circuit pattern on the surface 21, the S-polarized laser beam is scattered in various directions. If it is scattered by a particle or fault, due to depolarization the P-polarized component is scattered while being mixed into the S-polarized component. If the light is scattered from a circuit pattern, there occurs substantially no depolarization and the light is scattered with the plane of polarization of the S-polarized light being retained.

Of the light scattered from the scanning spot in response to the impingement of the laser beam, the light scattered in the direction just on the direction of incidence goes through the f-θ lens 55 and is reflected by the scanning mirror 54 toward the polarization beam splitter 51. While originally this light is the S-polarized laser beam with a frequency $f_2$, only the P-polarized component of the light depolarized due to the scattering by a particle or fault can pass through the polarization beam splitter 51 and can be directed toward the detection system 57 as a measurement light $P_2$. Since the S-polarized component therein is reflected by the beam splitter 51, it is not directed to the detection system 57.

It is to be noted that the optical arrangement is so structured that the optical path difference applied to the two light beams, from the separation of them by the polarization beam splitter 51 to the re-combination of them in response to the second impingement of them upon the beam splitter 51, is maintained within the range of coherent length of a laser beam used so as to assure the optical interference.

The two light beams directed to the detection system 57 and having different frequency components, i.e. the reference light $S_1$ and the measurement light $P_2$, have mutually orthogonally intersecting planes of polarization. The polarization filter 56 is so disposed to have its axis of transmission inclined by 45 deg. to both of these planes of polarization. Thus, when the two light beams pass the polarization filter 56, only the components of them corresponding to the axis of transmission can be transmitted therethrough, such that these two frequency components can have coinciding planes of polarization. Since the two light beams having coinciding planes of polarization have a small difference in frequency, they cause heterodyne interference. The resultant interference light is photoelectrically converted by the photoelectric detector of the detection system 57, whereby a beat signal is obtained. The signal from the detection system 57 is applied to the beat signal processing system 58 and, like the preceding embodiment, evaluation of a foreign particle or a fault is executed.

Similar detection is attainable even when the relationship between the P-polarization and the S-polarization is inverted totally. An example of this may be that: the arrangement of the light source system 50, the polarization filter 56, the detection system 57 and the beat signal processing system 58 is modified so as to change the direction of projection of light from the light source system 50 to the polarization beam splitter 51 as well as the direction of light exiting from the beam splitter 51 to the detection system 57, such that the laser beam reflected by the polarization beam splitter toward the mirror 53 comprises S-polarized light while the laser beam passed through the polarization beam splitter toward the scanning mirror 54 comprises P-polarized light.

In the present embodiment, only one light beam scans the surface to be inspected. Thus, it is not necessary to use an arrangement for registering scanning spots of two light beams as in the preceding embodiment. Additionally, the limitation to the incidence angle θ is small. Further, since the scattered light from a particle or fault goes reversely through the scanning optical system, the optical axis alignment for the scattered light and the reference light is easy and, additionally, no specific optical arrangement is necessary therefor. Owing to these advantages, simplification of structure and reduction of cost are assured. Moreover, since the reference light does not scan the surface to be inspected, the intensity of the reference light does not change, and the signal detection is stable.

Embodiment 9

A ninth embodiment of the present invention will be described with reference to FIG. 22. This embodiment corresponds to a modified form of the FIG. 21 embodiment, and the modified portion will be explained below. In the drawing, denoted at 50 is a light source system; at 59 is a detection system; at 60 and 65 are polarization beam splitters; at 61 is a half wave plate; at 62 is a reflection optical system such as a cat's eye reflector or a corner cube prism; and at 63 and 64 are filtering systems such as polarization filters.

The light source system 50 serves, like that of the FIG. 21 example, to produce a laser beam of two wavelengths of slightly different frequencies, along orthogonal planes of polarization on the same optical axis. The laser beam is projected on the polarization beam splitter 60 by which P-polarized laser beam P1 of a frequency f1 is allowed to pass therethrough while S-polarized laser beam S2 of a frequency f2 is reflected.

The P-polarized laser beam P1 passed through the beam splitter 60 then passes through the half wave plate 61 by which its plane of polarization is rotated by 90 deg., whereby it is transformed into S-polarized light. Then, it is reflected by the reflection optical system 62 backwardly along its oncoming path. While the half wave plate 61 is used in this example, the system may be so arranged that, before and after incidence of the light upon the reflection optical system 62, the light is caused to pass through a quarter wave plate twice. The same result of changing the plane of polarization from P to S, is attainable with this arrangement. The filter system 63 is provided to remove any unwanted light components produced due to the light separation performance or any setting error of the beam splitter 60. As the S-polarized laser beam S1 of frequency f1 reflected by the reflection optical system 62 enters the polarization beam splitter 65, since it is S-polarized light it is reflected by the beam splitter 65 toward the detection system 59, as a reference light.

On the other hand, the S-polarized light S2 of frequency f2 projected on and reflected by the polarization beam splitter 60, scans the surface 21 to be inspected, two-dimensionally. And, among the scattered rays from the surface 21, only the P-polarized components of the light depolarized by scattering by a particle, can pass through the polarization beam splitter 60. The thus passed P-polarized components go through the filter system 64 as a measurement light P2 which in turn goes through the polarization beam splitter 65. The filter system 64 is provided to remove unwanted (S-polarized) light components produced due to the light separation performance or any setting error of the polarization beam splitter 60.

It is to be noted that the optical path difference between the two lights, from separation by the polarization beam splitter to re-combination by the polarization beam splitter 65, is determined within a range of coherent length of a laser beam used, to assure optical interference.

Advantages of the present embodiment will now be explained. Where a polarization beam splitter is used as a light dividing means, practically a thoroughly theoretical light dividing operation is not attainable due to the optical performance or a setting error of the polarization beam splitter used. Thus, there occurs a small leak-in of light. Similarly, where a polarization beam splitter is used as a light combining means, a thoroughly theoretical wave combining operation is not attainable and there occurs a small mixing of light. In any case, this results in a possibility of a decrease of signal-to-noise (S/N) ratio.

In consideration of this, in this embodiment, the light dividing means (polarization beam splitter 60) for dividing the laser beam from the light source system and the combining means (polarization beam splitter 65) for combining the reference light and the measurement light, are provided independently of each other; and the filtering systems 63 and 64 are disposed between them and just before the combination of the reference light and the measurement light. The filtering system 63 is provided to reduce unwanted light mixed into the reference light, while the filtering system 64 is provided to reduce unwanted light to be mixed into the measurement light. By these filtering systems, considerable enhancement of S/N ratio is assured.

Embodiment 10

Figure 22:
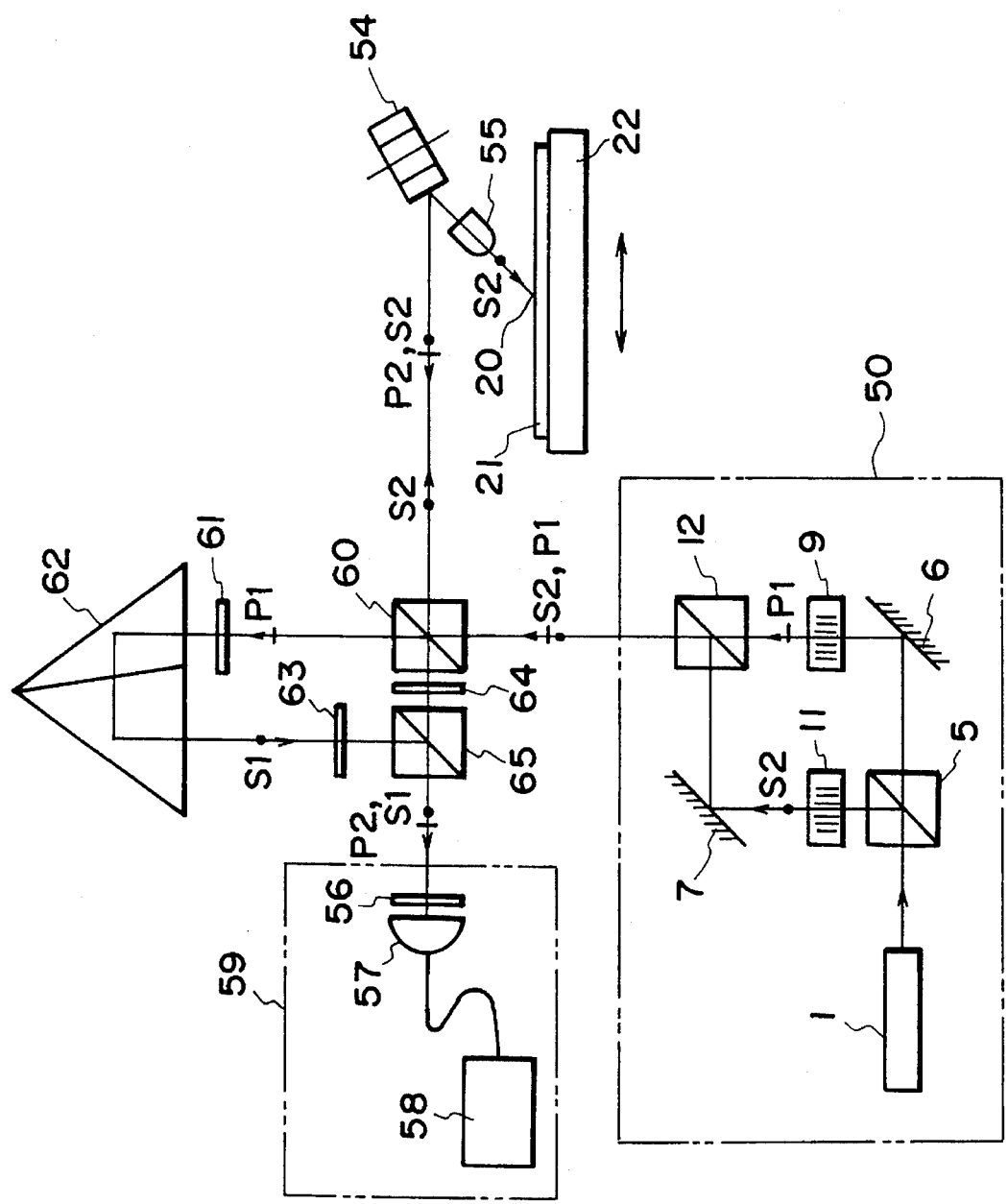
FIG. 22 is a schematic view of a ninth embodiment of the present invention.
Figure 23:
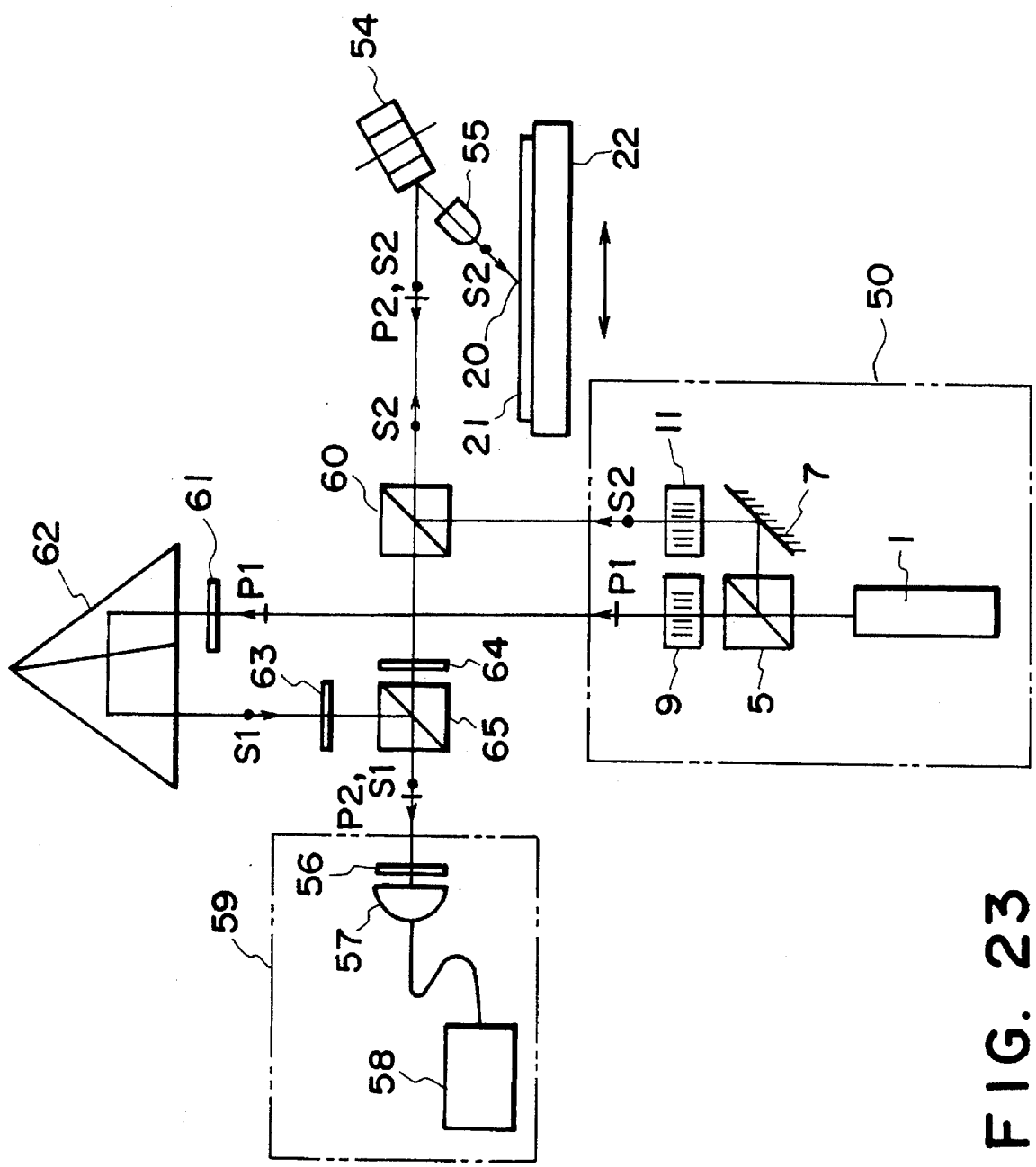
FIG. 23 is a schematic view of a tenth embodiment of the present invention.

Referring to FIG. 23, a tenth embodiment of the present invention which corresponds to a modified form of the FIG. 22 embodiment will be explained. Light source system 50 projects two laser beams without overlapping. P-polarized laser beam P1 from the light source system 50 passes through a half wave plate 61 by which the plane of polarization is rotated by 90 deg., whereby it is transformed into S-polarized light. It is then reflected by a reflection optical system 622 backwardly along its oncoming path, and it is projected on a polarization beam splitter 65. As this S-polarized laser beam S1 of a frequency f1 impinges on the beam splitter 65, since it is S-polarized light it is reflected by the beam splitter 65 toward a detection system, as a reference light.

On the other hand, S-polarized laser beam S2 from the light source system 50 is reflected by a polarization beam splitter 60. The following operation is the same as that of the preceding embodiment.

In this embodiment, after bisection of the light by the polarization beam splitter 65 of the light source system, the divided light beams are not re-combined until they are re-combined by the polarization beam splitter 65. Therefore, there is no possibility of leak-in of unwanted components of frequency f2 into the path of reference light or of leak-in of unwanted components of frequency f1 into the path of projected light. Thus, a particle or fault can be detected with a high S/N ratio.

Figure 24:
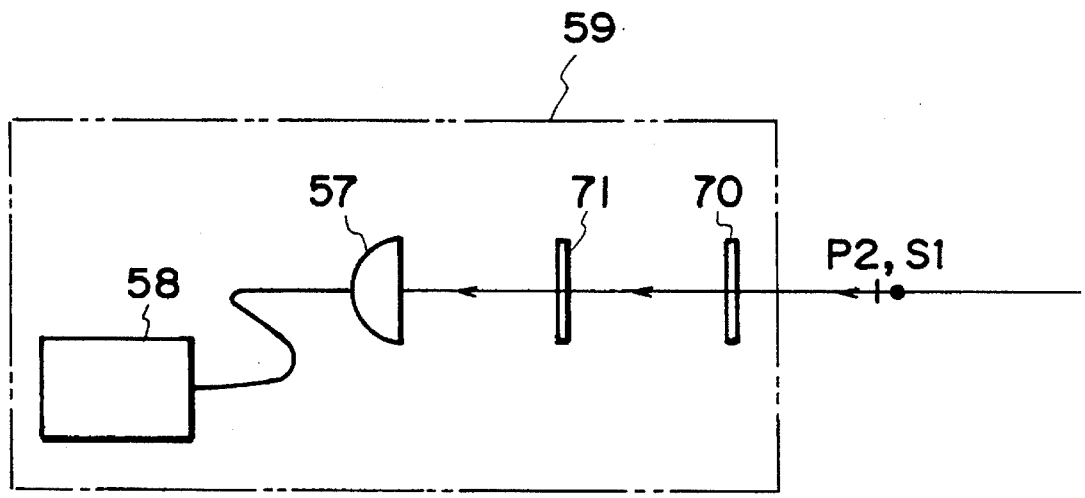
FIG. 24 is a schematic view of a modified form of a detection system.

FIG. 24 shows a modified optical arrangement for causing interference of P-polarized light with S-polarized light, which may be used in place of the detection system 59 of the FIGS. 22 or 23 example. Before the photoelectric detector 57, a quarter wave plate 70 and a polarizing plate 71 are disposed. Here, the quarter wave plate 70 is positioned with its retardant axis inclined by 45 deg. with respect to both the direction of polarization of the P-polarized light and that of the S-polarized light. By means of the polarization filter 71, a polarized light having a desired inclination can be extracted.

Figure 25:
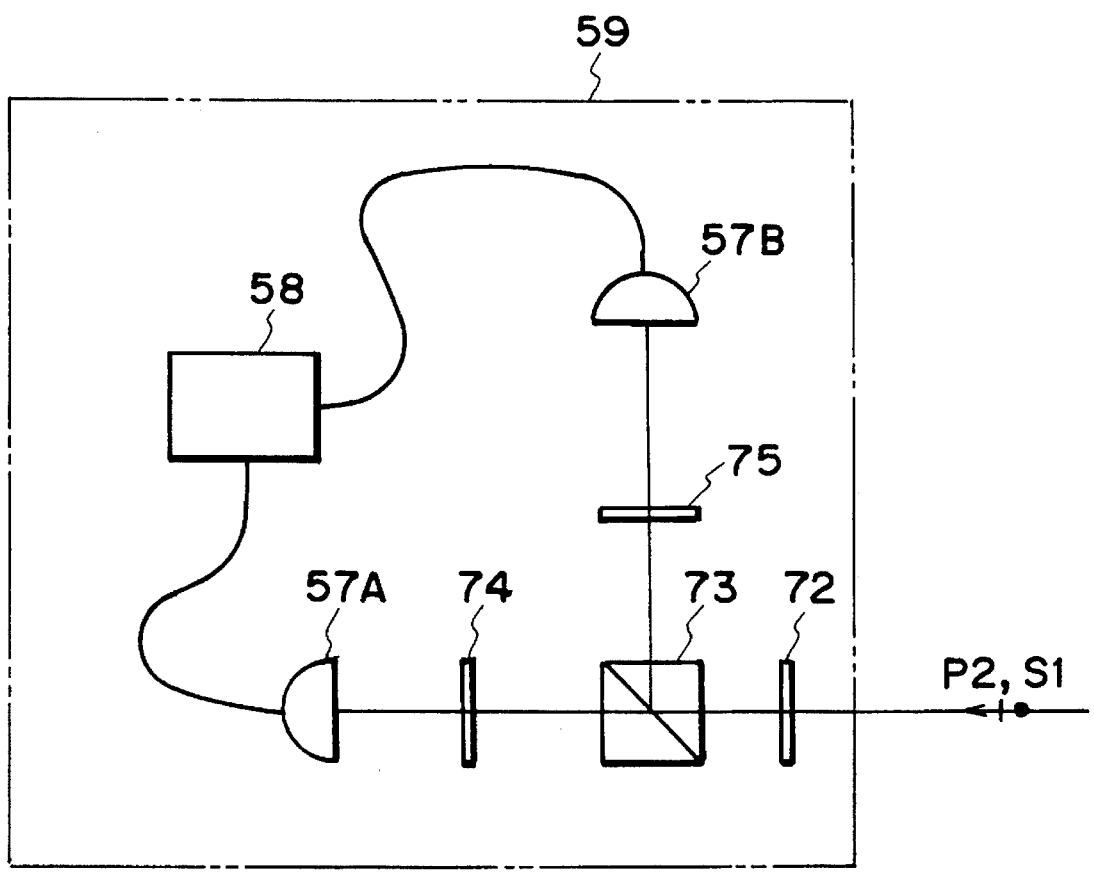
FIG. 25 is a schematic view of another modified form of a detection system.

FIG. 25 shows another modified form of the detection system 59. Quarter wave plate 72 is disposed with its retardant axis inclined by 45 deg. with respect to the directions of polarization of the P-polarized light and S-polarized light. Polarization beam splitter 73 serves to divide light into a component parallel to the sheet of the drawing and a component perpendicular thereto. The divided light beams are received by polarization filters 74 and 75, respectively, and then they are photoelectrically converted by photoelectric detectors 57A and 57B, respectively. The signals produced by these two detectors 57A and 57B are beat signals having a phase difference $\pi$, which phase difference can be adjusted by the distances from the polarization beam splitter 73 to the respective photoelectric detectors. Based on these two signals, a signal processing system 58 operates to execute particle inspection.

Embodiment 11

Figure 26:
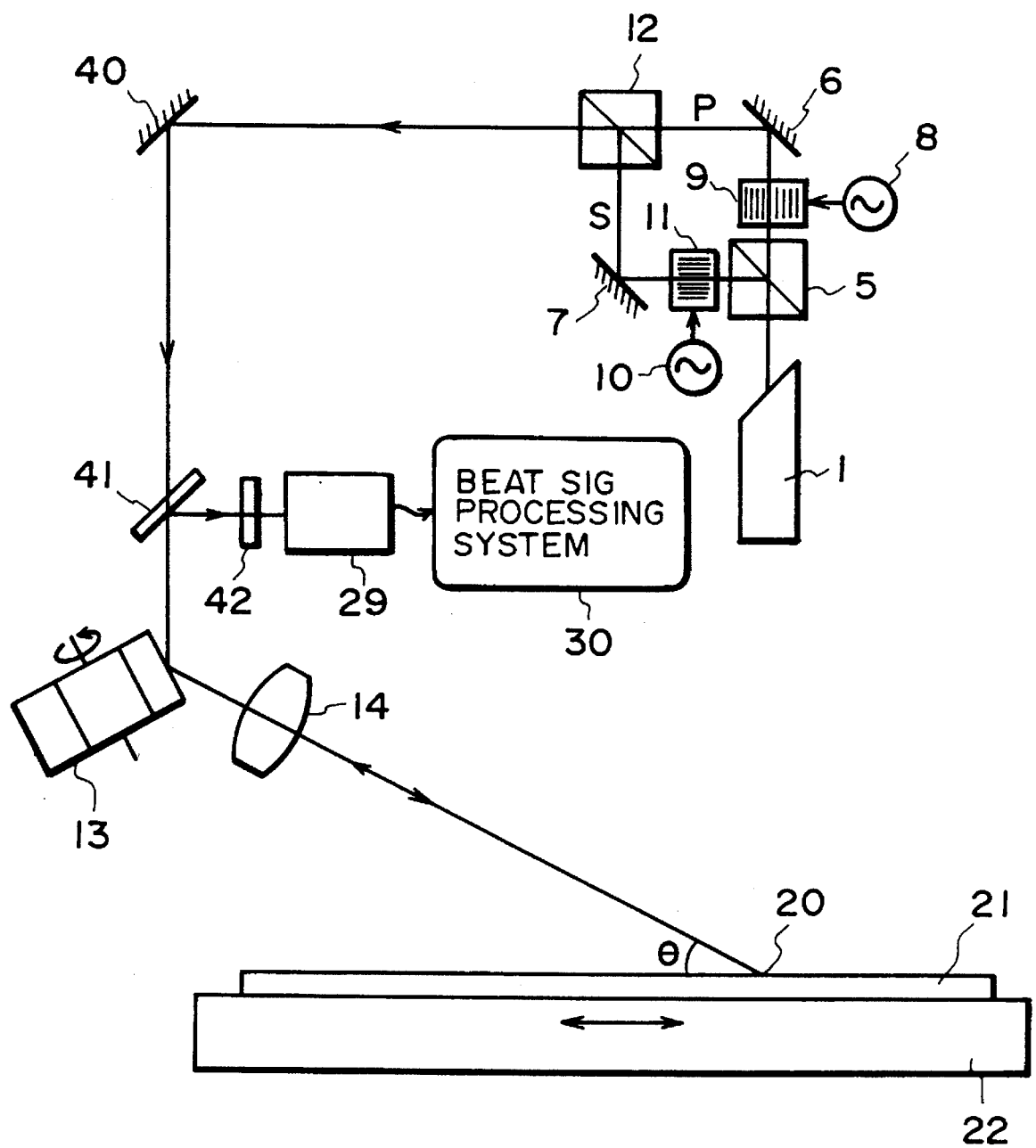
FIG. 26 is a schematic view of an eleventh embodiment of the present invention.

FIG. 26 shows the structure according to an eleventh embodiment wherein further structural simplification is sought. Like numerals as those used in the preceding embodiments are assigned to corresponding or similar elements. Denoted in the drawing at 40 is a reflection mirror; at 41 is a half mirror; and at 42 is a polarization filter provided to selectively transmit only P-polarized light or S-polarized light.

In the structure of the present embodiment, the light source system for providing a combined beam of a P-polarized laser beam modulated with a shift frequency $\omega$ and an S-polarized laser beam modulated with a shift frequency $\omega+\Delta\omega$, is like that of the preceding embodiment. This may of course be replaced by use of a Zeeman laser or control of an injection current to a semiconductor laser. The provided laser beam is reflected by the mirror 40, and light passing through the half mirror 41 enters a scanning optical system comprising a scanning mirror 13 and an f-$\theta$ lens 14 at an incidence angle $\theta$ by which it is scanningly deflected. Namely, in this embodiment, a single laser beam containing both the P-polarized light and the S-polarized light with a frequency difference, is projected to a spot 20.

Here, if there is a particle or fault or a circuit pattern within the spot 20, scattering of light occurs. Of the light scattered, the components scattered along the path of incidence of light go via the f-$\theta$ lens 14 and the scanning mirror 13 and reach the half mirror 41. Then, the light components reflected by the half mirror 41 are received by a polarization filter 27, by which the polarization planes of them are registered to the P-polarization or S-polarization, and then a signal is detected by a photoelectric detector 29. This signal is then processed by a beat signal processing system 30 as in the preceding embodiment.

Figure 27:
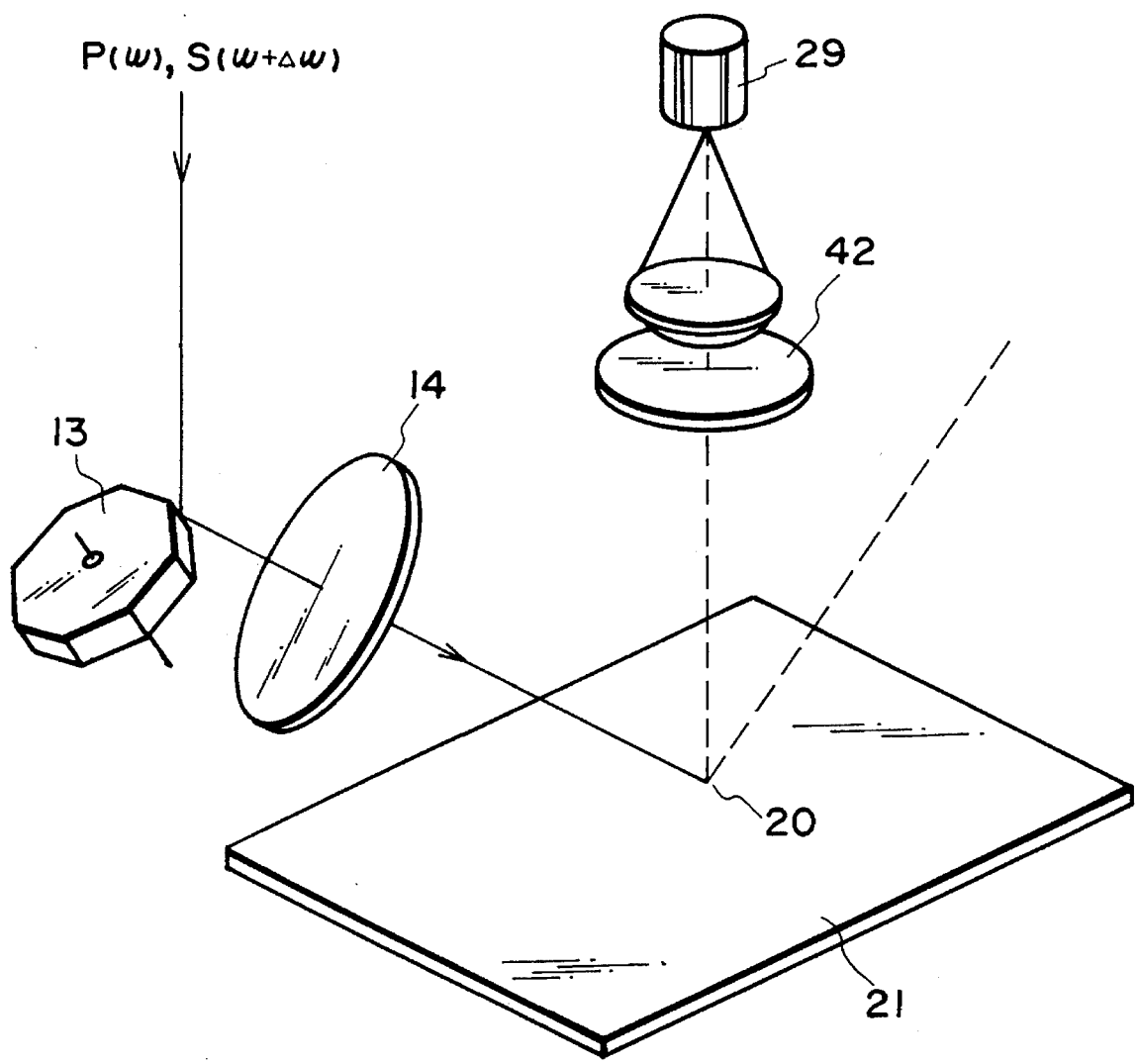
FIG. 27 is a perspective view of a portion of the FIG. 26 embodiment.

The direction of detecting the scattered light is not limited to the one disclosed in this embodiment. If the detection optical system is arranged such as shown in FIG. 27, for example, it is possible to detect the scattered light in a desired direction.

Here, the principle of detecting a particle or fault in the present embodiment will be explained. The linearly polarized laser beam projected to the scanning spot 20 and having a P-polarized component (shift frequency $\omega$) and an S-polarized component (shift frequency $\omega+\Delta\omega$), is depolarized by light scattering by the particle or fault, and thus an S-polarized component with a shift frequency $\omega$ and a P-polarized component with a shift frequency $\omega+\Delta\omega$ are newly produced. This depolarization is caused mainly by a particle or fault, and it substantially hardly occurs by a circuit pattern, as discussed in the foregoing. Thus, with the scattering by a circuit pattern, there occurs substantially no production of an additional light component like this.

If depolarization occurs, because of coinciding planes of polarization, heterodyne interference is caused by the originally presented P-polarized light component (frequency $\omega$) and the P-polarized light component (frequency $\omega+\Delta\omega$) resulting from the depolarization. Similarly, because of coinciding planes of polarization, heterodyne interference is caused by the originally presented S-polarized light component (frequency $\omega$) and the S-polarized light component (frequency $\omega+\Delta\omega$) resulting from the depolarization. Where the polarization filter 42 disposed in front of the photodetector is one adapted to selectively transmit the P-polarized light only, the photoelectric detector 29 receives only the heterodyne interference light of P-polarized component, and a corresponding beat signal is produced. Where the polarization filter 42 is one adapted to selectively transmit the S-polarized light only, the detector 29 receives only the heterodyne interference light of S-polarized component, and a corresponding beat signal is produced.

Next, the manner of distinguishing a particle or fault from a circuit pattern, will be explained in detail. Generally, the spot has a diameter of several tens of microns, and a particle to be detected has a size not greater than one-tenth ($\frac{1}{10}$) of it. Thus, the time period in which the scattered light is produced is approximately equal to the time period in which the spot passes the particle. If, as an example, the scanning mirror 13 comprises an octahedral polygonal mirror rotating at 2000 rpm, the scanning spot 20 passes a particle 201 in several hundred seconds. Thus, if a driving frequency difference of 20 MHz is applied to the acousto-optic devices 9 and 11, then in this period of several hundred seconds, frequency signals of about ten are superposed on a DC signal.

Figure 28:
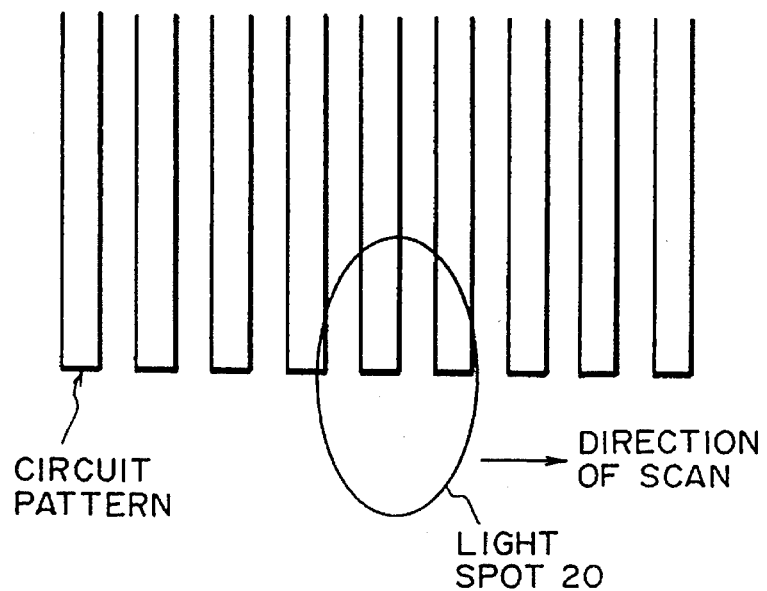
FIG. 28 is a schematic view, showing the relationship between a circuit pattern and a light spot.
Figure 29:
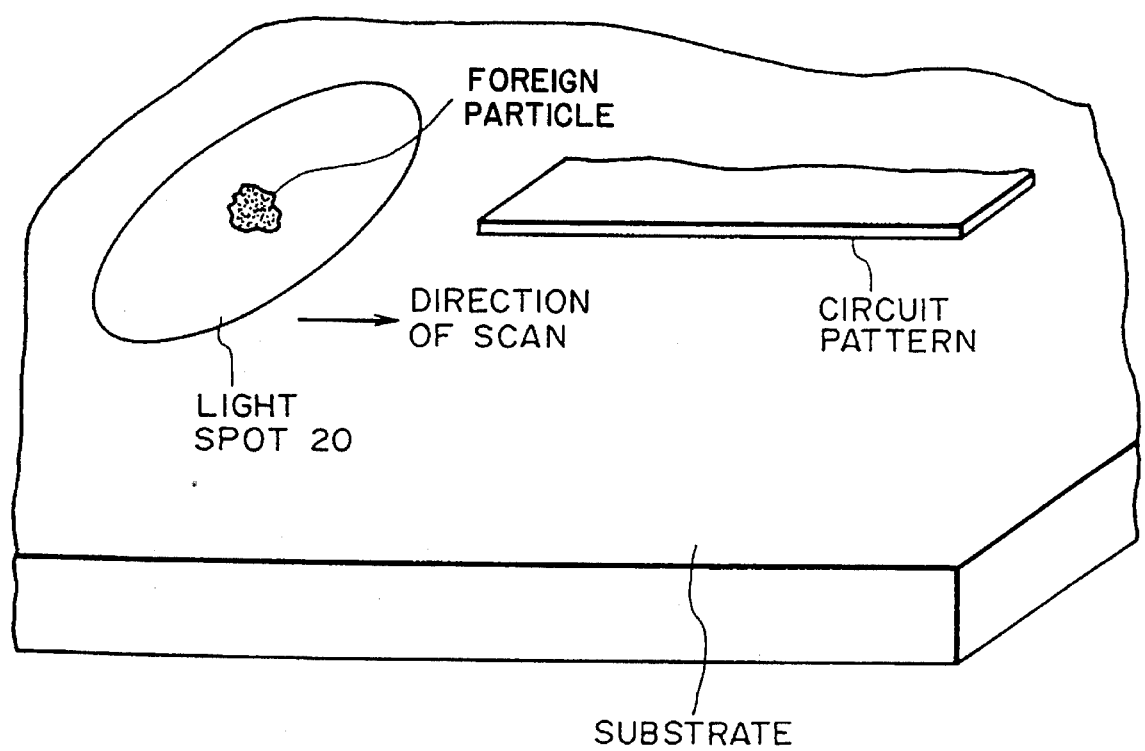
FIG. 29 is a schematic view, showing the manner of a scan of a surface, to be inspected, with a light spot.

On the other hand, in many cases the circuit pattern comprises repeated pattern elements such as shown in FIG. 28, and it is larger than the spot 20. If, as an example, both a particle and a circuit pattern are present in the scan region (FIG. 29), a resultant detection signal from the photodetector 29 may be such as shown in FIG. 30, for example. As described hereinbefore, since depolarization occurs in the light scattering by a particle or fault, a beat signal having a large amplitude is produced. On the other hand, in the light scattering by a circuit pattern, depolarization occurs substantially hardly. Thus, there is produced no beat signal, or only a very weak beat signal is produced. Consequently, the amplitude at a certain beat frequency is considerably larger in the case of a particle or fault (amplitude $a_p$) than in the case of a circuit pattern (amplitude $a_s$). Thus, based on this difference, it is possible to distinguish a particle or fault from a circuit pattern.

Figure 31:
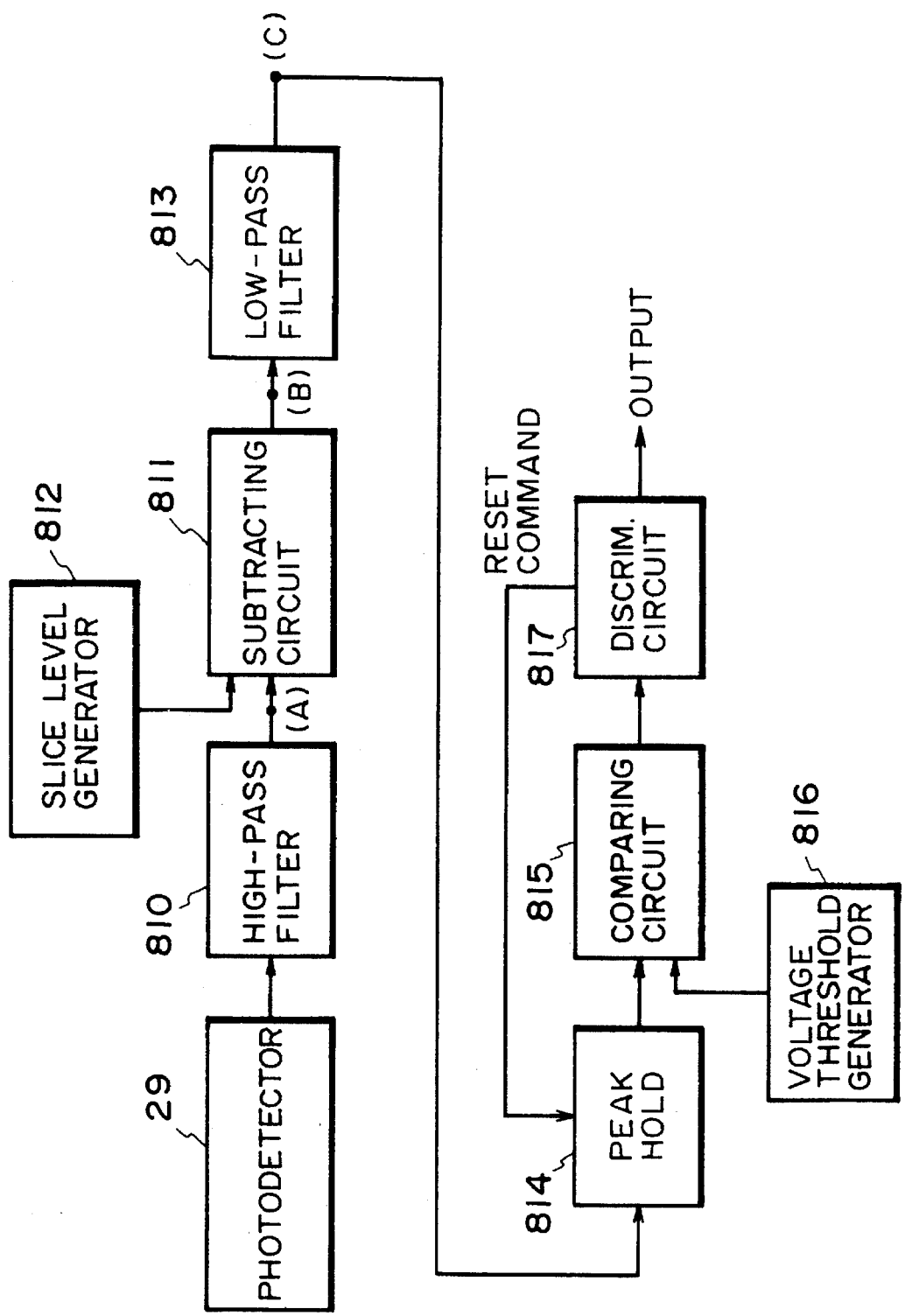
FIG. 31 is a diagrammatic view of a signal processing circuit.
Figure 32:
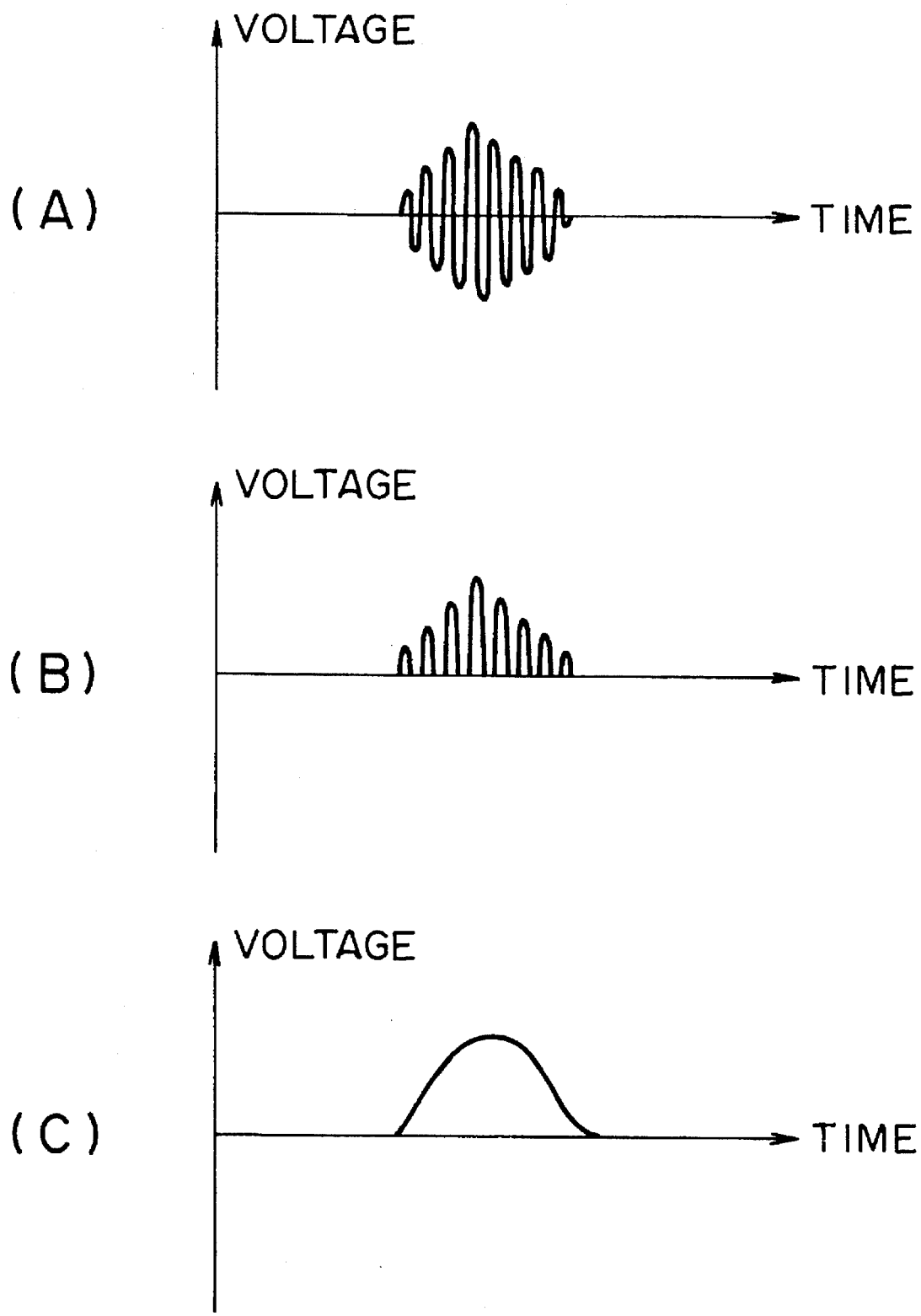
FIG. 32 is a schematic view, showing the waveforms of signals at respective portions of the signal processing circuit of FIG. 31.

FIG. 31 is a block diagram showing details of a signal processing circuit. FIG. 32 shows signal waveforms at respective portions in FIG. 31. Generally stating, the signal processing circuit comprises a block for converting a beat signal into an envelope, and a block for discriminating a particle or fault while distinguishing it from a circuit pattern on the basis of the level of the envelope.

The detection signal obtained through the photoelectric detector 29 is applied to a highpass filter 810 by which its DC components are removed (FIG. 32, (A)). Subtracting circuit 811 subtracts a predetermined voltage, as applied by a slice level generating circuit 812, from the output voltage of the highpass filter 810, whereby those lower than a predetermined voltage are removed (FIG. 32, (B)). Then, through a lowpass filter 813, it is shaped into an envelope of a beat signal (FIG. 32, (C)). This is the process of converting a beat signal into an envelope. The resultant envelope is applied to a peak-hold circuit 814 whereby the maximum signal level of it is held. Comparing circuit 815 compares in magnitude the peak-hold level and a voltage threshold level as applied from a threshold level generating circuit 816. On the basis of the result of this comparison, a discriminating circuit 817 discriminates a particle or fault while distinguishing it from a circuit pattern, and a corresponding signal is outputted. If the processing to one signal is completed, the discriminating circuit 817 applies a reset signal to the peak-hold circuit 814, for resetting the peak-hold level.

Embodiment 12

Figure 33:
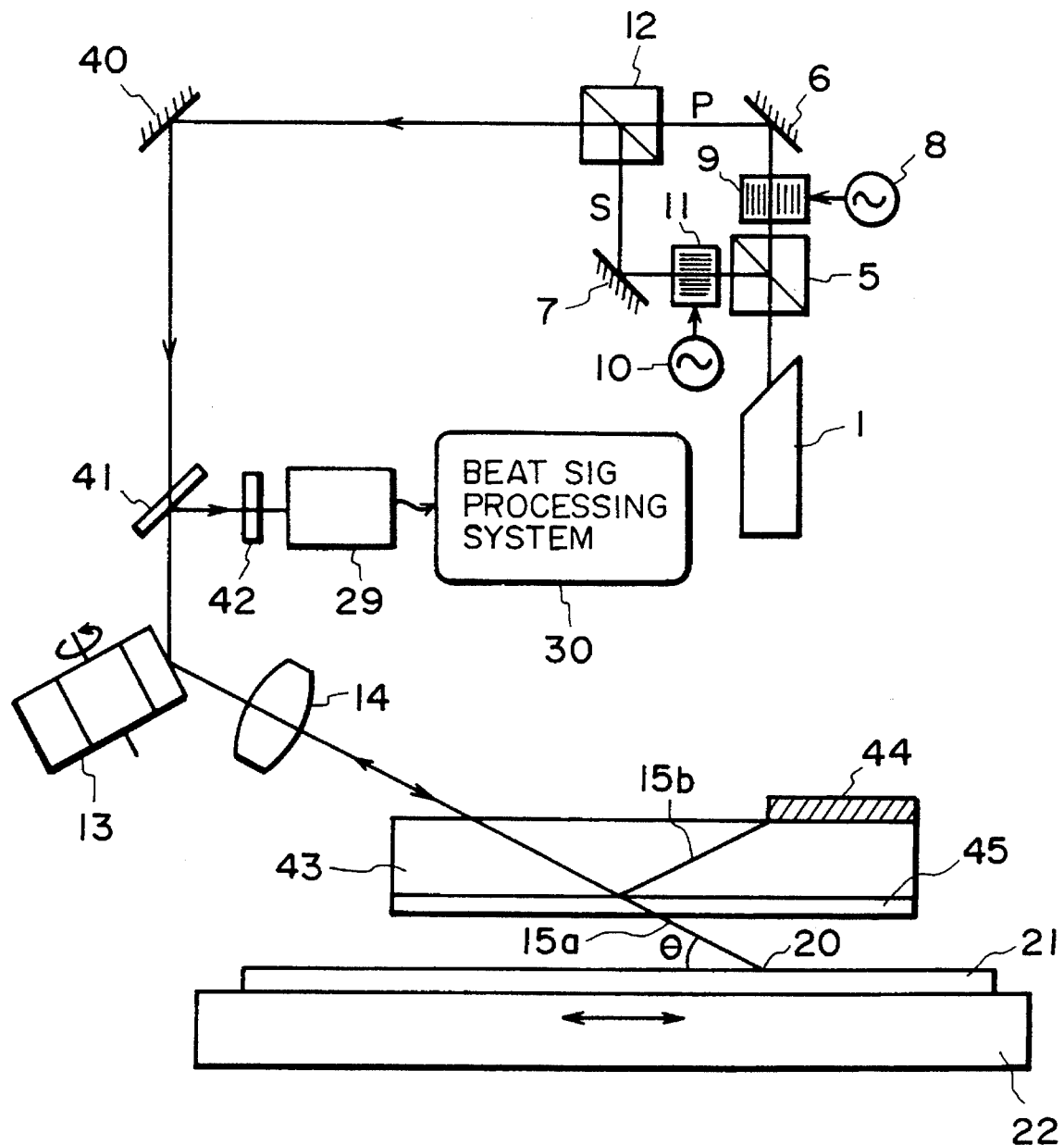
FIG. 33 is a schematic view of a twelfth embodiment of the present invention.

FIG. 33 shows the structure of a twelfth embodiment of the present invention. Like numerals as those of the FIG. 26 embodiment are assigned to corresponding or similar elements. In the drawing, a polarization filter 42 is so disposed as to have its axis of transmission inclined by 45 deg. to both of the planes of polarization of P-polarized light and S-polarized light. Denoted at 43 is a transparent flat glass plate; at 44 is a scattering member formed on the glass plate 43;

and at 45 is a polarization beam splitter provided at the bottom of the glass plate 43.

An important structural feature of this embodiment resides in that the flat glass plate 43, which has the scattering member 44 formed in a portion of the upper surface thereof and the polarization beam splitter 45 formed at its bottom, is disposed in front of the surface 21 to be inspected. The scattering member 44 has a structure effective to cause light scattering. It may comprise edges of patterns etched with chromium, like a circuit pattern. These edges may be formed along the scan line. The polarization beam splitter 45 has an optical property for transmitting P-polarized light components and reflecting S-polarized light components. By this polarization beam splitter 45, the scanning light from an f-θ lens 14 is separated into a P-polarized laser beam 15a (shift frequency ω) and an S-polarized laser beam 15b (shift frequency ω+Δω). The transmitted and separated P-polarized laser beam 15a is converged upon the surface 21 to be inspected to form a scanning spot thereon. On the other hand, the reflected and separated S-polarized laser beam 15b is converged on the edge portion of the scattering member 44 to scan the same.

If there is a particle or fault or a circuit pattern in an area scanned with the P-polarized laser beam 15a, scattered light is produced. On the other hand, scattered light is produced also by the S-polarized light 15b converged on the scattering member 44. Of these scattered lights, those components scattered along a path in the same direction as the path of light incidence go via the polarization beam splitter 45, the f-θ lens 14 and the scanning mirror 13 and impinge on a half mirror 41. Then, the P-polarized component and the S-polarized component reflected by the half mirror 41 are received by the polarization filter 42 by which the directions of polarization are aligned. As a consequence, due to optical heterodyne interference, there occurs beating of light intensity. This is photoelectrically converted by the photoelectric detector 29, whereby a beat signal is produced.

Figure 34:
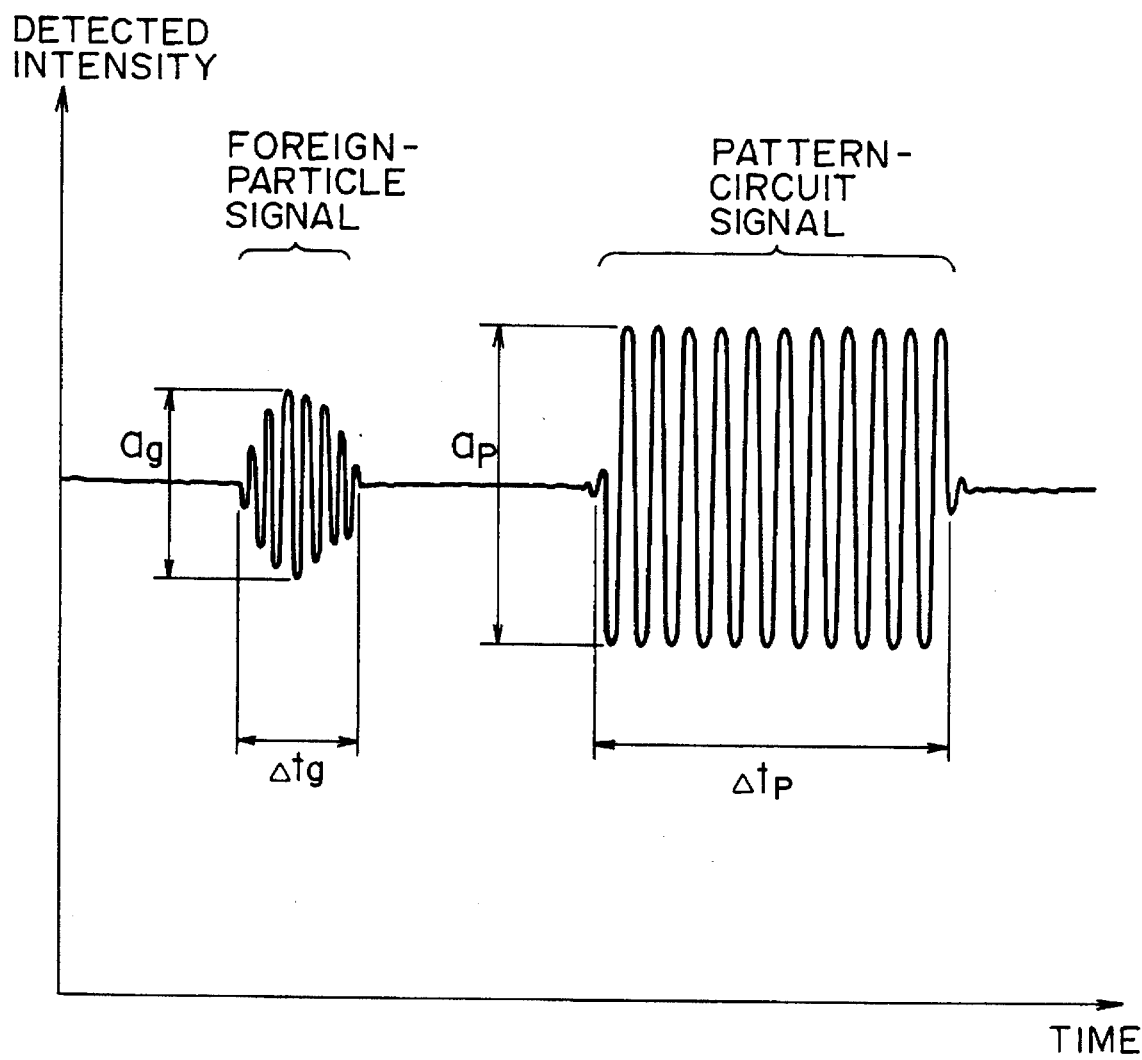
FIG. 34 is a schematic view, showing the waveform of a detection signal obtainable with the apparatus of the twelfth embodiment.

Now, the manner of distinguishing scattered light from a particle or fault, over scattered light from a circuit pattern, in this embodiment, will be explained. FIG. 34 shows signal waveforms which may be obtained through the apparatus of this embodiment under the same condition as the FIG. 29 example. Here, if the signal time width or period of a beat signal attributable to a particle is denoted by ΔTg while the signal time width or period attributable to a circuit pattern is denoted by ΔTp, then they are in the following relationship:

ΔTg<ΔTp

The present embodiment uses this time difference to discriminate a particle or fault from a circuit pattern. Practically, by counting the number of waves of the beat frequency, the time width is detected. Namely, while in the preceding embodiment a particle or fault is discriminated from a circuit pattern by utilizing depolarization attributable to the particle or fault, in the present embodiment they are distinguished on the basis of signal processing.

Figure 35:
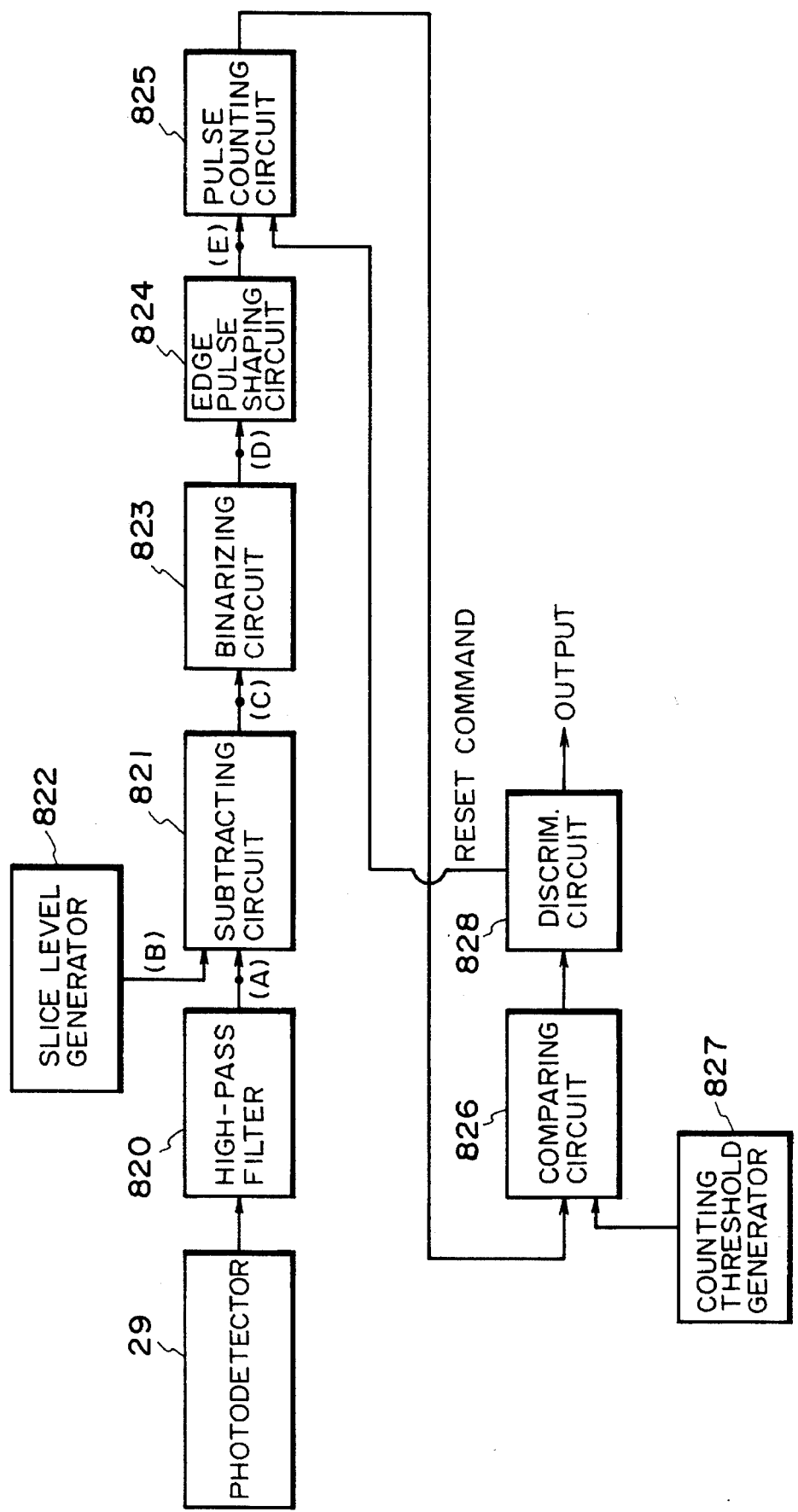
FIG. 35 is a diagrammatic view of a signal processing circuit.

FIG. 35 is a block diagram showing details of a signal processing circuit of this embodiment. FIG. 36 shows signal waveforms at respective portions of FIG. 35. Generally stating, the signal processing circuit comprises a block for converting a beat signal into pulses, and a block for discriminating a particle or fault while distinguishing it from a circuit pattern, on the basis of the number of the pulses.

The detection signal obtained through the photoelectric detector 29 is applied to a highpass filter 820 by which its DC components are removed (FIG. 36, (A)). Subtracting circuit 821 subtracts a predetermined voltage (FIG. 36, (B)), as applied by a slice level generating circuit 822, from the output voltage of the highpass filter 820, whereby those lower than a predetermined voltage are removed (FIG. 36, (C)). Then, a binarizing circuit 823 shapes the signal into a rectangular wave (FIG. 36, (D)). Edge pulse shaping circuit 824 then produces a pulse signal in response to each rise or fall in the rectangular wave (FIG. 36, (E)). This is the process of converting a beat signal into pulses. The resultant pulse signals are counted by a pulse counting circuit 825, and a comparing circuit 826 compares in magnitude the number of counted pulses (representing the time width of the beat signal) with a threshold level as applied from a threshold level generating circuit 827. On the basis of the result of this comparison, a discriminating circuit 828 discriminates a particle or fault while distinguishing it from a circuit pattern, and a corresponding signal is outputted. If the processing to one signal is completed, the discriminating circuit 827 applies a reset signal to the pulse counting circuit 825, for resetting the pulse counting.

Embodiment 13

A thirteenth embodiment of the present invention will now be described with reference to FIG. 37. In the drawing, denoted at 80 is a laser light source which emits a circularly polarized light beam; at 81 is a half mirror; at 82 and 83 are acousto-optic modulators; at 84, 85, 86 and 87 are reflection mirrors; at 89 and 94 are lens systems; at 90 is a surface to be inspected; and at 91 is a stage. Also, denoted at 88, 92 and 95 are filtering systems such as polarization filters, each including an adjusting mechanism for rotating the polarization filter to adjust the direction of the transmission axis. Denoted at 99 is a driver for controlling these adjusting mechanisms. Denoted at 96 is a photoelectric detector, and denoted at 97 is a signal processing system.

In this embodiment, the stage 91 is movable both rotationally and along an axis or, alternatively, it is movable along two axes, for two-dimensional scanning of the surface to be inspected. However, the structure is not limited to this. For example, the mirrors 85 and 87 may be replaced by a scanning mirror system having a galvano mirror or polygonal mirror, and the lens system 89 may be replaced by a scanning f-θ lens for beam scanning deflection, while the stage may be moved one-dimensionally in a direction intersecting with it.

Circularly polarized laser light from the laser light source 80 is divided by the half mirror 80 into two lights. These lights are then frequency modulated by the acousto-optic modulators 82 and 83, respectively, whereby lights L1 and L3 having slightly different frequencies are produced. By way of the mirrors 85 and 86, the light L3 is projected on the polarization filter 88 through which only a linearly polarized light component of predetermined direction of polarization passes. It is then projected by the lens system 98 upon the surface 90 to be inspected, as irradiation light L4.

The other light L1 is reflected by the mirror 87 and, by means of the polarization filter 92, only linearly polarized light of a predetermined direction of polarization is passed and directed as a reference light L2 toward the half mirror 93. The half mirror 93 combines the light L2 and the scattered light (measurement light L5) from the surface 90, whereby light L6 is produced.

As regards the scattered light L5 from the surface being inspected, its major polarization direction differs with whether the light scattering member comprises a particle or a fine structure such as a circuit pattern. Also, depending on the type of a circuit pattern, for example, the direction of polarization may change slightly.

In this embodiment, initially, by means of a signal from the driver 99, the axis of transmission of the polarization filter 88 is set in an appropriate direction best suited to the type of the circuit pattern to be inspected, to thereby determine the direction of polarization of the irradiation light L4. Then, by means of a signal from the driver 99, the axis of transmission of the polarization filter 92 is adjusted so that the direction of polarization of the reference light L2 extends orthogonally to the major polarization direction of the scattered light L5 from the circuit pattern. In addition thereto, by means of a signal from the driver 99, the axis of transmission of the polarization filter 95 is adjusted so that it is in the same direction as the direction of polarization of the reference light L2. For the adjustment of these polarization filters, a data table in which types of reticles to be inspected and corresponding set values for these polarization filters are stored, may preferably be prepared beforehand.

Since two linearly polarized lights having orthogonally intersecting directions of polarization do not interfere with each other, with the adjustment described above no optical interference occurs even if scattered light from a circuit pattern is directed to the detection system. Thus, no noise component is produced. On the other hand, as regards scattered light from a particle to be detected, its component in the same direction as the direction of polarization of the reference light interferes with the reference light, whereby an interference signal is produced. Here, since these two lights have slightly different frequencies, optical heterodyne interference occurs and the produced interference signal is a beat signal.

It is to be noted that an angle as close to 90 deg. should preferably be defined between the major polarization direction of the scattered light from a particle and that of the scattered light from a circuit pattern. Thus, the direction of polarization or the angle of projection of the irradiation light L4 as well as the disposition of the photoelectric detector 96 may be determined to provide such an angle.

Embodiment 14

Figure 37:
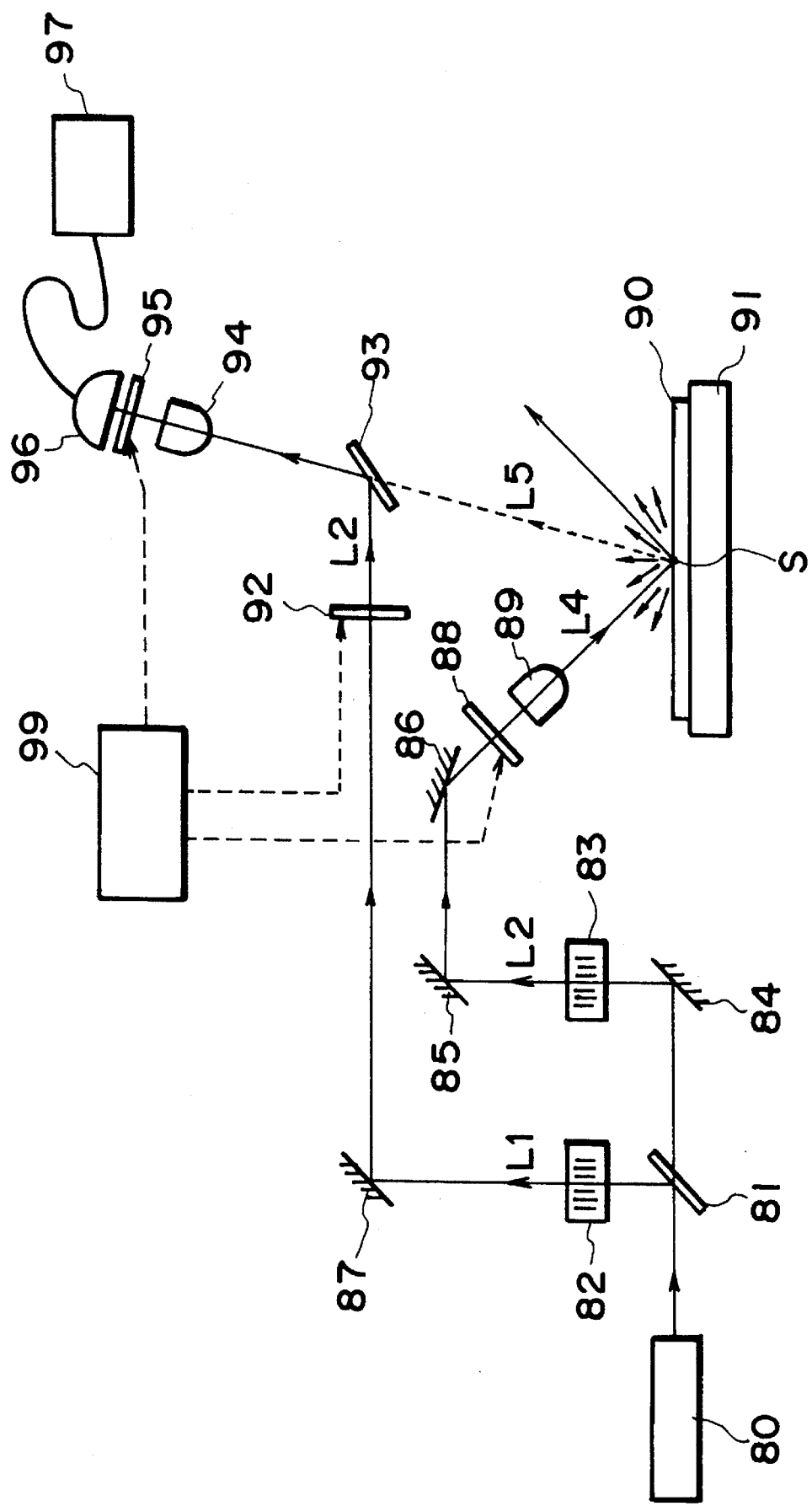
FIG. 37 is a schematic view of a thirteenth embodiment of the present invention.
Figure 38:
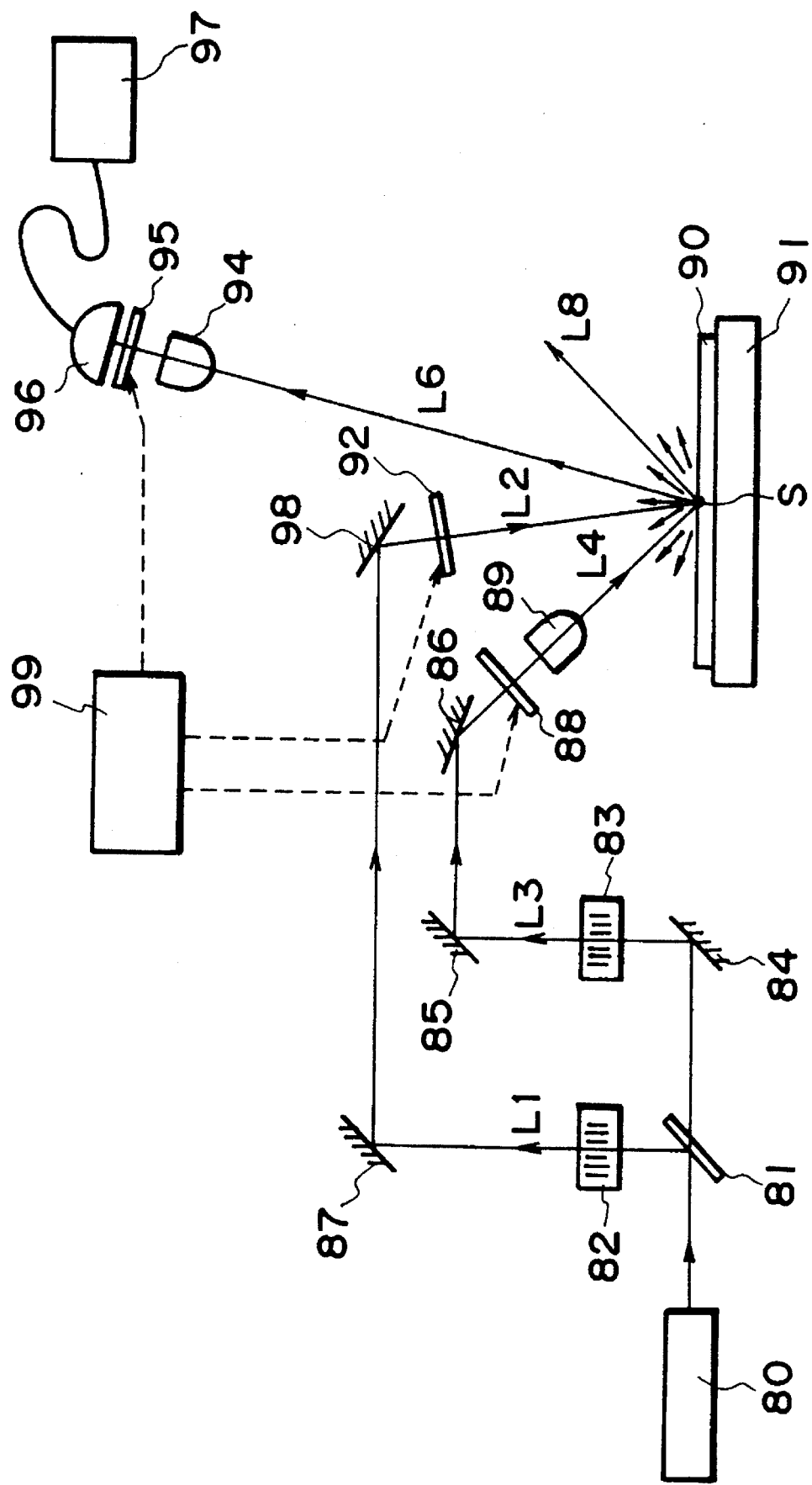
FIG. 38 is a schematic view of a fourteenth embodiment of the present invention.

FIG. 38 shows a fourteenth embodiment of the present invention, and like numerals as those in FIG. 37 are assigned to corresponding elements. While in the FIG. 37 embodiment the reference light L2 is not projected on the surface to be inspected, in the present embodiment the reference light also is projected on the surface to be inspected.

By means of a polarization filter 92, light L1 is transformed into a predetermined linearly polarized light which is then projected as a reference light L2 at the same position on the surface 90, being irradiated by the irradiation light L4. Photoelectric detector 96 is disposed in the direction along which the light L2 is regularly reflected by the surface 90. Thus, reflected light (zeroth order light) of the light L2 and reflected by the surface 90 is combined with the scattered light which, of the light scattered as a result of the irradiation by the light L4, has been scattered toward the photoelectric detector 96, whereby light L6 is provided. The light L6 then goes through the lens system 94 and the filter system 95, and impinges on the photoelectric detector 96.

In this embodiment, like the preceding embodiment, initially, by means of a signal from the driver 99, the axis of transmission of the polarization filter 88 is set in an optimum direction best suited to the type of a circuit pattern to be inspected, and the direction of polarization of the irradiation light L4 is determined. Then, by means of a signal from a driver 99, the axis of transmission of the polarization filter 92 is adjusted so that the direction of polarization of the reference light L2 extends orthogonally to the major polarization direction of the scattered light L5 from the circuit pattern. Additionally, by means of a signal from the driver 99, the axis of transmission of the polarization filter 95 is adjusted so that it is laid in the same direction as the polarization direction of the reference light L2.

Embodiment 15

Figure 39:
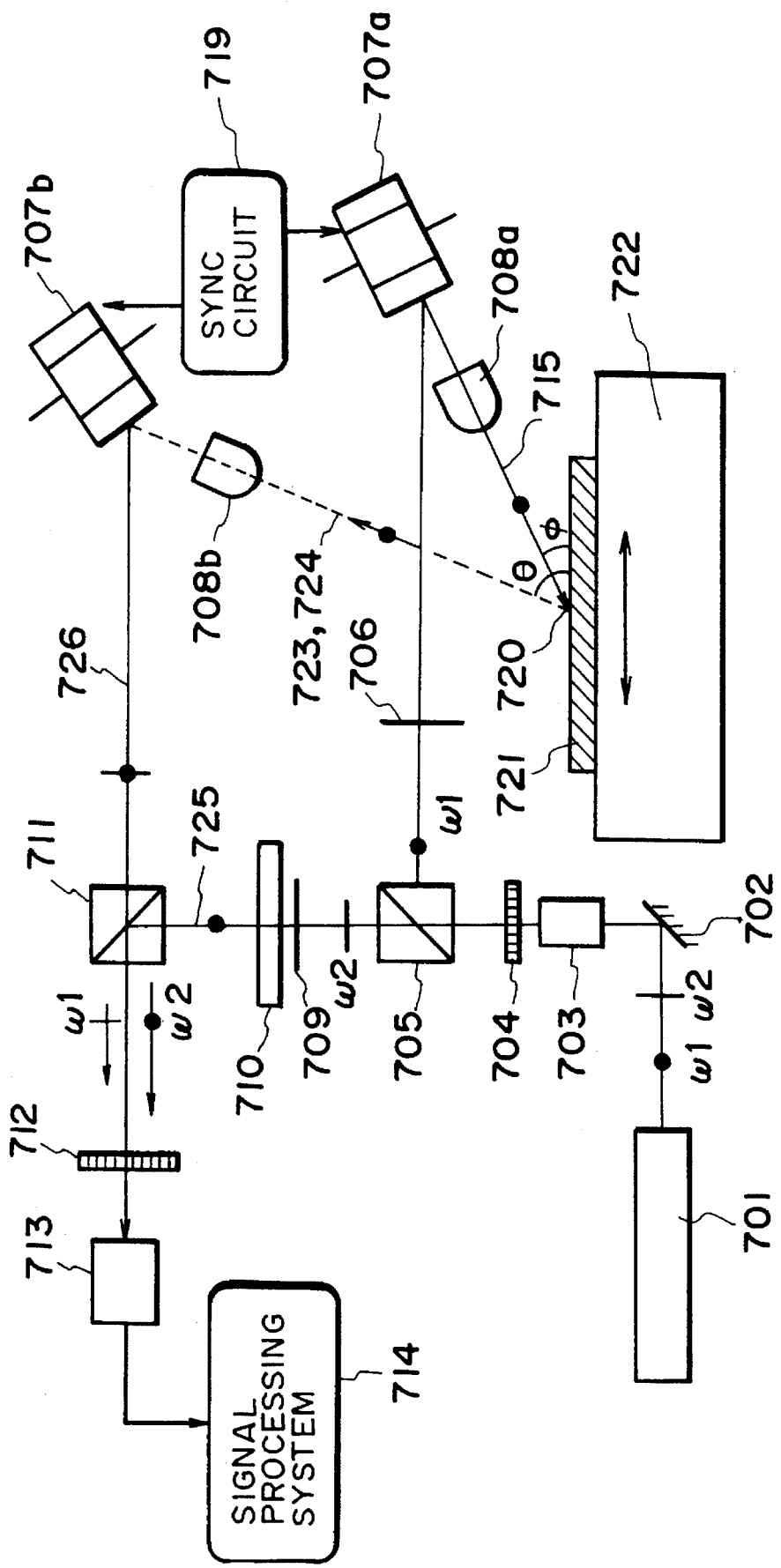
FIG. 39 is a schematic view of a fifteenth embodiment of the present invention.

FIG. 39 shows a fifteenth embodiment of the present invention. In the drawing, denoted at 701 is a light source means which produces a laser beam which contains two frequency components having orthogonal directions of polarization. Denoted at 702 is a mirror; at 703 is a collimator optical system for transforming the laser beam into one having an appropriate beam diameter; at 704 is a filtering system; at 705 is a wave dividing means such as a polarization beam splitter, for example, which serves to divide a linearly polarized laser having different frequencies into two linearly polarized lasers; and at 709 is a filtering system including an ND filter, for attenuating the laser beam intensity to provide one suited to particle/fault inspection. Denoted at 707a and 707b are polygonal mirrors, and denoted at 708a and 708b are f-θ lens systems. Denoted at 719 is a synchronizing circuit for providing complete synchronization in rotation between the two polygonal mirrors 707a and 707b. Denoted at 710 is a polarizing element such as a half wave plate, for example, for controlling the direction of polarization of the laser beam; at 711 is a wave combining means such as a polarization beam splitter, for example, for combining scattered light with reference light; at 712 is a polarizing element for registration of polarization direction; at 713 is a photoelectric detector such as a photomultiplier, for example; and at 721 is the surface to be inspected, which may be the surface of an original such as a reticle or a mask to be inspected. Denoted at 722 is a scanning stage system on which an original is to be placed and by which it is to be moved.

A laser beam produced by the light source means 701 comprises mutually orthogonal, linearly polarized lights having an S-polarized component of a frequency $\omega 1$ and a P-polarized component of a frequency $\omega 2$ ($=\omega 1+\Delta\omega$). This can be accomplished by using a Zeeman laser, for example, or by modulating an injection current to a semiconductor laser. Alternatively, one or two acousto-optic devices may be used to modulate two single-wavelength laser beams at a relative shift frequency $\Delta\omega$.

The laser beam produced by the light source means 701 goes via the mirror 702 and then it it collimated by the collimator optical system 703 and the filtering system 704. Subsequently, it is divided by the wave dividing means 5 into S-polarized laser light (reflected, of frequency $\omega 2$) and P-polarized laser light (transmitted, of frequency $\omega 1$).

The P-polarized laser transmitted through the dividing means 705 is attenuated by the filtering system 709, whereby an appropriate intensity is provided. After this, by means of the polarizing element 710, the direction of polarization thereof is rotated by 90 deg., whereby S-polarized laser light of frequency $\omega 2$ is provided. It is then introduced into the wave combining means 711 as a reference light 725.

On the other hand, the S-polarized laser reflected by the dividing means 705 is attenuated by the filtering system 706, whereby an intensity best suited to particle/fault inspection is set. Thereafter, it is introduced into a scanning irradiation optical system which comprises the polygonal mirror 707a and the f-θ lens system 708a, whereby an input light 715 is provided. It is projected on the surface 721 to be inspected, at an incidence angle $\phi$, whereby a scanning spot 720 is formed thereon. With the rotation of the polygonal mirror 707a, this scanning spot 720 displaces in a direction perpendicular to the sheet of the drawing, to thereby optically scan the surface 721 to be inspected. Also, the stage system 722 moves the surface 721 in a direction (denoted by an arrow) perpendicular to the direction of optical scan by the scanning spot 720. By this, the surface 721 to be inspected is scanned two-dimensionally.

As the surface 721 is irradiated with the scanning spot 720 and if there is a particle/fault or a circuit pattern in the irradiated area, there is produced (i) scattered light 723 (P-polarized light and S-polarized light) resulting from depolarization of S-polarized laser 15 by the particle or fault, or (ii) scattered light 724 (mainly comprising S-polarized light) due to the circuit pattern. Here, the reason why a particle or fault causes depolarization is that: since generally the surface of a particle or fault is rough, polarization is liable to be disturbed during irregular reflection and scattering, which in turn results in creation of a polarization component different from the incident polarization plane. As compared therewith, depolarization is very small in scattered light from an object such as a circuit pattern, which has a relatively uniform and smooth surface.

Among the scattered rays from the surface 721 being inspected, those back scattered components 723 and 724 which are along the back scattering direction (angle θ to the surface being inspected) different from the direction of incidence of the input light 715, are collected by a scanning collection optical system which comprises the polygonal mirror 707b and the f-θ lens 708b. Here, since the polygonal mirrors 707a and 707b are rotated while being completely synchronized with each other by means of the synchronizing circuit 719, at every moment the same point on the surface 721 is scanned by them. The scattered light 726 (frequency ω1) thus collected is introduced into the wave combining means 711. It is to be noted that, in the optical arrangement of this embodiment, the axis of the chief ray of the scattered light 726 as collected is fixed and undisplaceable regardless of the optical scan.

The reference light 725 and the scattered light 726 are combined with each other by the wave combining means 711. Here, while the light 726 contains both of the S-polarized component and the P-polarized component, what can pass through the wave combining means 711 is only the P-polarized component produced as a result of depolarization due to a particle or fault. Thus, the combined light consists of a P-polarized component of a frequency ω1 (i.e. a depolarized component due to the particle or fault) and the S-polarized component of a frequency ω2 (i.e. reference light).

The light combined by the wave combining means 711 is received by the polarizing element 712 by which the direction of polarization is registered, and then it impinges on the photoelectric detector 713. On the photoelectric conversion surface of this detector 713, optical heterodyne interference occurs, as a result of which a beat signal of a frequency Δω (=|ω1−ω2|) can be observed. The polarizing element 712 may comprise a polarizer having its axis of transmission inclined by 45 deg. with respect to both of the directions of P-polarization and S-polarization, such that it may serve to register the polarization direction along the direction of its transmission axis. Alternatively, it may comprise a combination of a quarter wave plate and a linear polarizer, having a function for registering the direction of polarization.

The particle/fault detection in this embodiment is based on the phenomenon that: Of the scattered rays, what is contributable to produce a beat signal is the P-polarized light component resulting from depolarization. Even if scattered light from a circuit pattern is mixed, the dominant is the S-polarized light component. It is not combined by the wave combining means 711 and, therefore, it is not contributable to the optical heterodyne interference. Thus, it does not contribute to produce a beat signal. This means that, even if there is a scattered light from a circuit pattern, it does not produce a beat signal or, if a beat signal is produced, the signal is very feeble. Namely, the system of this embodiment ensures particle/fault inspection of very high sensitivity and good S/N ratio. The signal processing system 714 detects a beat signal and discriminates a particle or fault.

The optical arrangement of this embodiment may be modified so that the relationship between the S-polarized light and the P-polarized light is totally inverted. Particle/fault detection is attainable essentially in the same manner.

In the embodiment described above, a scanning light collection optical system is provided and disposed in a direction different from the angle of irradiation by a scanning irradiation optical system, by which it is assured to collect scattered light in a direction of high detection sensitivity, while avoiding diffraction light from a circuit pattern. It is therefore possible to provide particle/fault inspection of high S/N ratio and high sensitivity.

Embodiment 16

Figure 40:
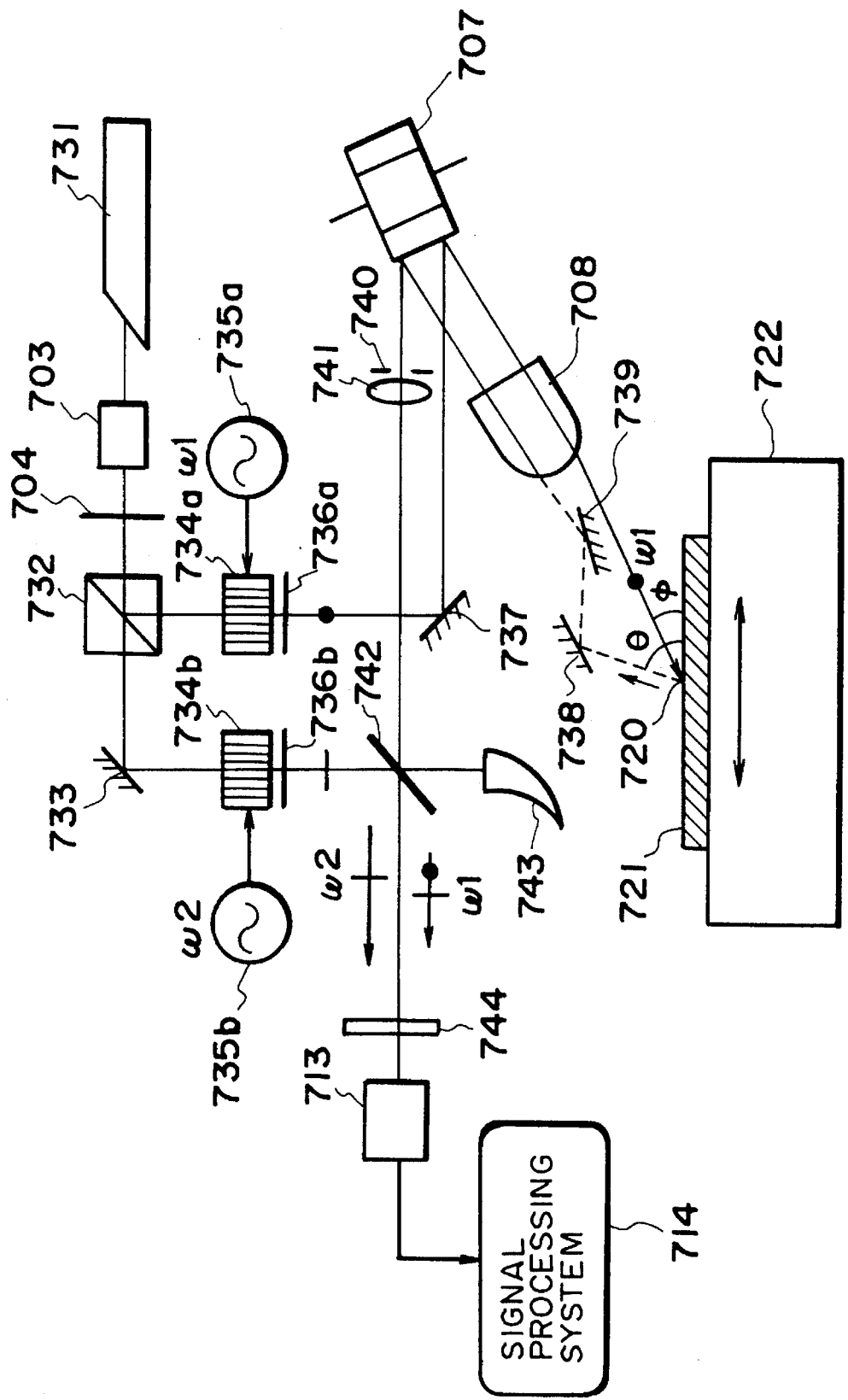
FIG. 40 is a schematic view of a sixteenth embodiment of the present invention.

FIG. 40 shows a sixteenth embodiment of the present invention, and like numerals as those of FIG. 39 are assigned to corresponding elements. In the drawing, denoted at 731 is a laser source; at 732 is a polarization beam splitter for dividing the laser beam into two orthogonal, linearly polarized lights; at 733 is a mirror; at 734a and 734b are acousto-optic devices each for modulating the laser with an appropriate frequency; at 735a and 735b are drivers for driving corresponding acousto-optic devices, respectively; at 736a and 736b are filtering systems each including an ND filter for setting light intensity; at 737, 738 and 739 are mirrors; at 740 and 741 are correction optical systems; at 742 is a half mirror having a high transmissivity; at 743 is a beam trap; and at 744 is a polarizing element.

The basic principle of particle/fault detection in this embodiment is the same as that of the fifteenth embodiment. A laser beam from the laser source 731 goes through a collimator system 703 and a filtering system 704, and then it is divided by the polarization beam splitter 732 into S-polarized laser and P-polarized laser light. By means of the acousto-optic devices 734a and 734b, they are modulated into frequencies ω1 and ω2 (|ω1−ω2|=Δω). These structural elements provide a light source unit. In place of using an acousto-optic device, a light source unit with an equivalent function, including a Zeeman laser or a semiconductor laser, may be used.

The S-polarized light modulated to the frequency ω1 is reflected by the mirror 737. Then, by means of a scanning optical system comprising a polygonal mirror 707 and an f-θ lens system 708, it is projected on the surface 721 to be inspected, at an incidence angle φ, whereby a scanning spot 720 is formed thereon. It is to be noted that the f-θ lens system 708 is used in off-axis.

In the spot 720, the properties of scattered rays caused by a particle or fault or by a circuit pattern are such as described with reference to the fifteenth embodiment, and the P-component of the scattered light produced as a result of depolarization due to a particle or fault can be detected as a beat signal. In order to collect such scattered light within a collection angle θ, the mirrors 738 and 739 which are of elongated shape corresponding to the scan region, are used to change the path of advancement of the scattered light such that it is projected again on the f-θ lens system 708 in off-axis. The scattered light as collected by the f-θ lens system 708 is parallel to the input light incident on the reflection surface of the polygonal mirror 7. Subsequently, the light goes through a correction optical system comprising the aperture member 740 and the lens system 741, and it is received by the half mirror 742. Here, the correction optical system is provided to correct any focus error due to a difference between the input light path and the collected light path, from the f-θ lens system 708 to the surface 721 to be inspected. While in the preceding embodiment two polygonal mirrors rotating in synchronism with each other are used, in the present embodiment a single polygonal mirror is used in common. Namely, the scanning system comprising the polygonal mirror 707 and the f-θ lens 708 functions both as a scanning irradiation optical system and as a scanning light collection optical system.

The scattered light as collected (containing the P-polarized component of frequency ω1, resulting from depolarization due to a particle or fault) and the P-polarized laser (reference light) modulated by the acousto-optic device 734b with a frequency ω2, are combined with each other by the half mirror 742. Any unwanted light if produced in this wave combination is trapped by the beam trap 743. The half mirror 742 may have a set transmissivity of about 90%, for example. Such a high transmissivity is for introducing a largest quantity of feeble scattered light from a particle or fault, into the photoelectric detector 713. The combined light enters the linear polarizer 744 which serves to block S-polarized component, such that only the P-polarized light component, corresponding to the depolarized component due to a particle or fault, contributes to cause optical heterodyne interference. Thus, a beat signal is detected by the photoelectric detector 713 and, through a similar signal processing operation as in the preceding embodiment, particle/fault inspection is executed.

In the present embodiment, as compared with the fifteenth embodiment, only a pair of a polygonal mirror and an f-θ lens system is necessary. Thus, it is contributable to an improvement of reliability and to reduction of cost.

Embodiment 17

Figure 41:
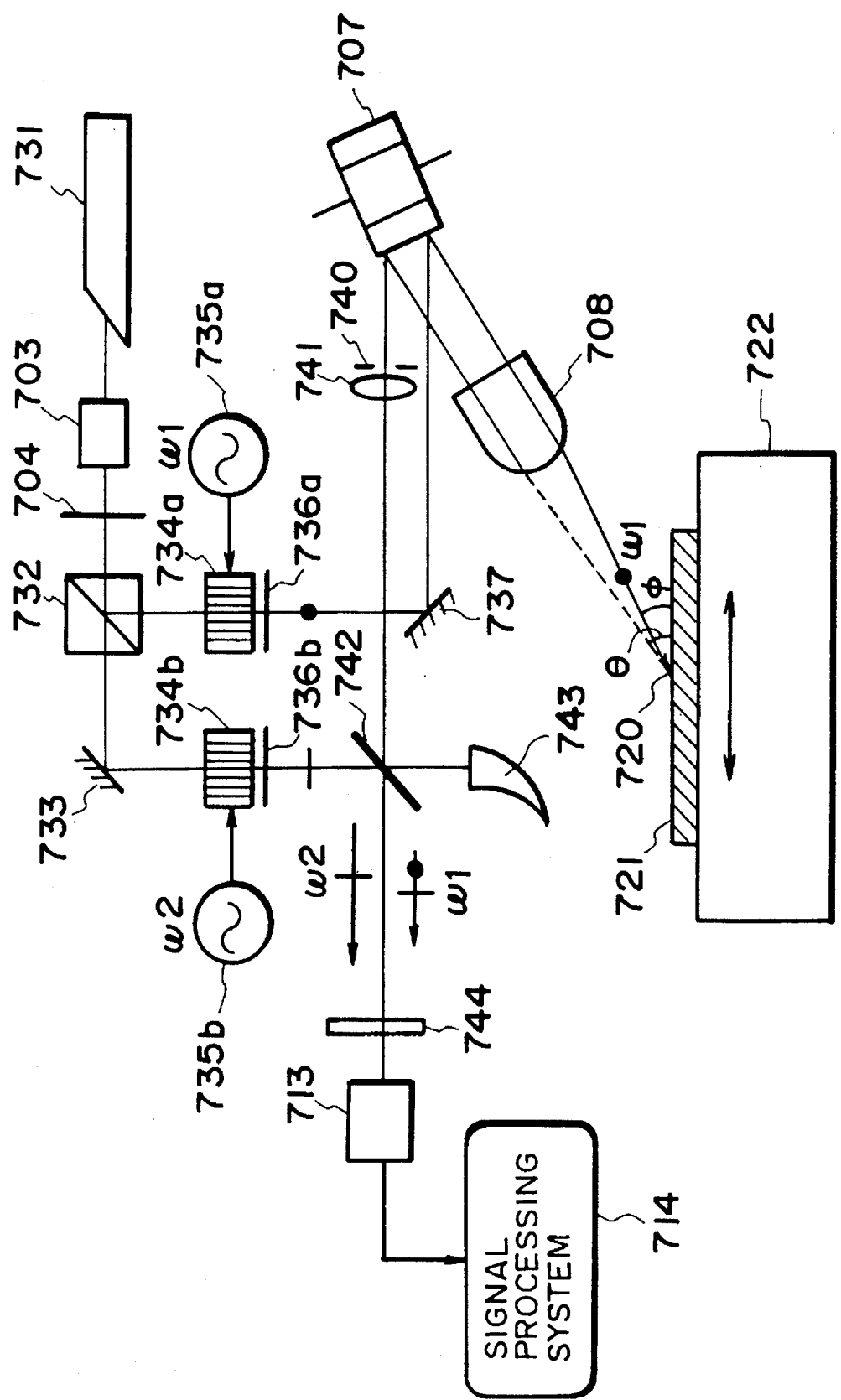
FIG. 41 is a schematic view of a seventeenth embodiment of the present invention.

FIG. 41 shows a seventeenth embodiment of the present invention, which corresponds to a modified form of the sixteenth embodiment of FIG. 40. Like numerals as those of FIG. 40 are assigned to corresponding elements. The structure of FIG. 40 with the mirrors 738 and 739 being omitted, corresponds to the present embodiment. The structure of the present embodiment is effective particularly on an occasion when the difference between the incidence angle φ and the collection angle θ should be made small.

Embodiment 18

Figure 42:
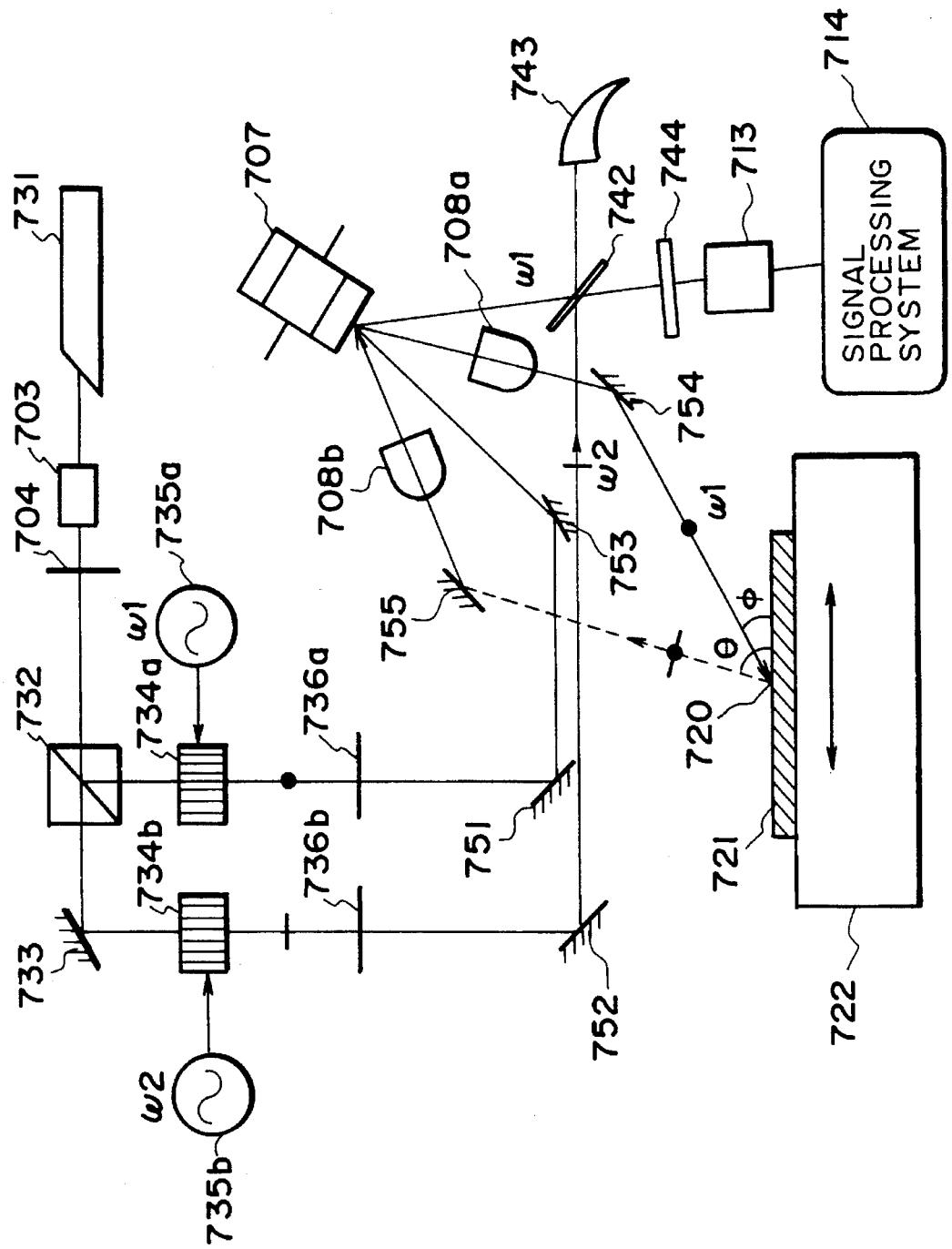
FIG. 42 is a schematic view of an eighteenth embodiment of the present invention.

FIG. 42 shows an eighteenth embodiment of the present invention, and like numerals as those of the preceding embodiments are assigned to corresponding elements. In the drawing, denoted at 751–757 are all mirrors. An important feature of this embodiment is that two f-θ lens systems 708a and 708b and a single common polygonal mirror 707 cooperate to provide a scanning irradiation optical system and a scanning collection optical system.

Embodiment 19

Figure 43:
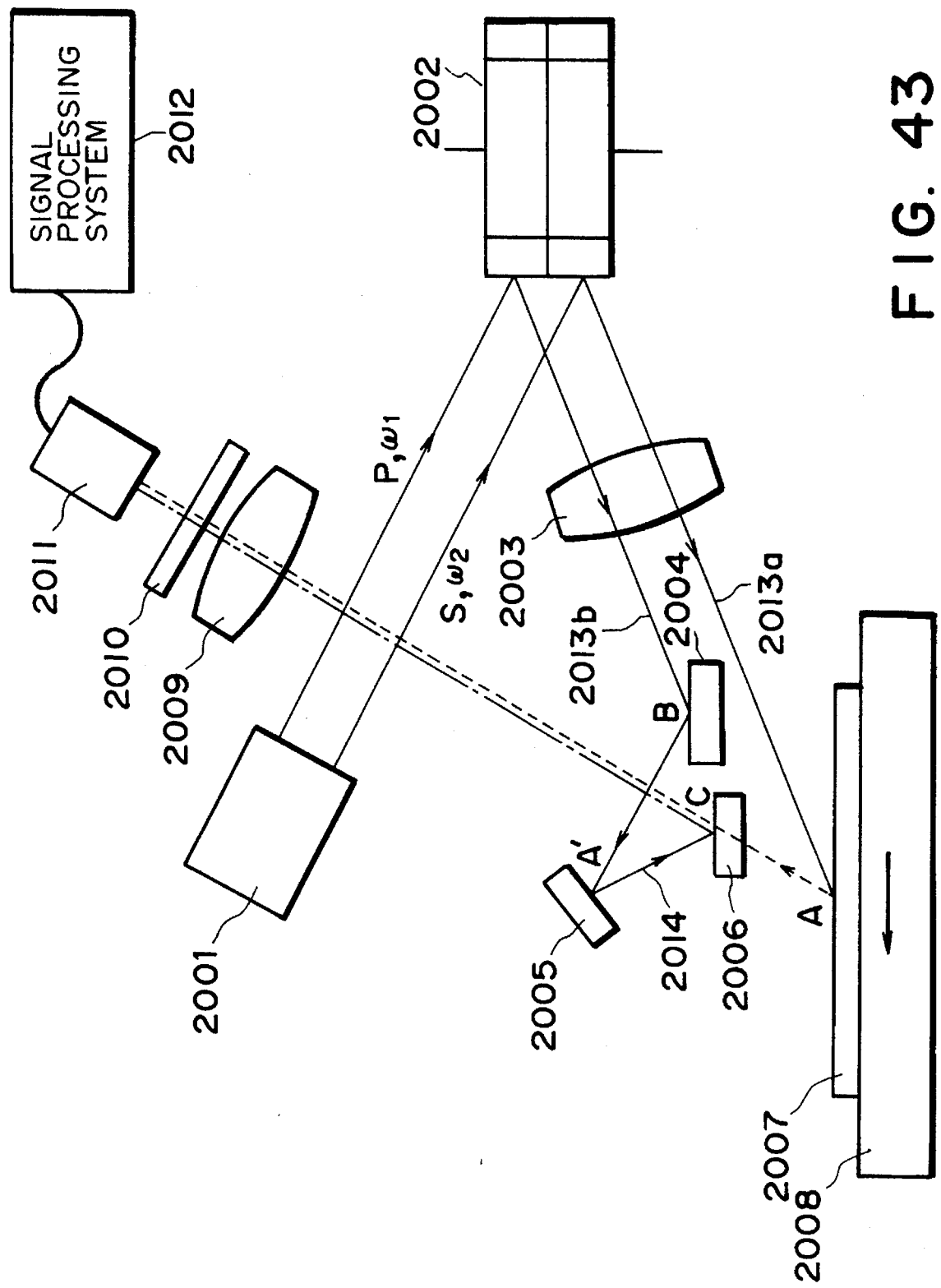
FIG. 43 is a schematic side view of a nineteenth embodiment of the present invention.
Figure 44:
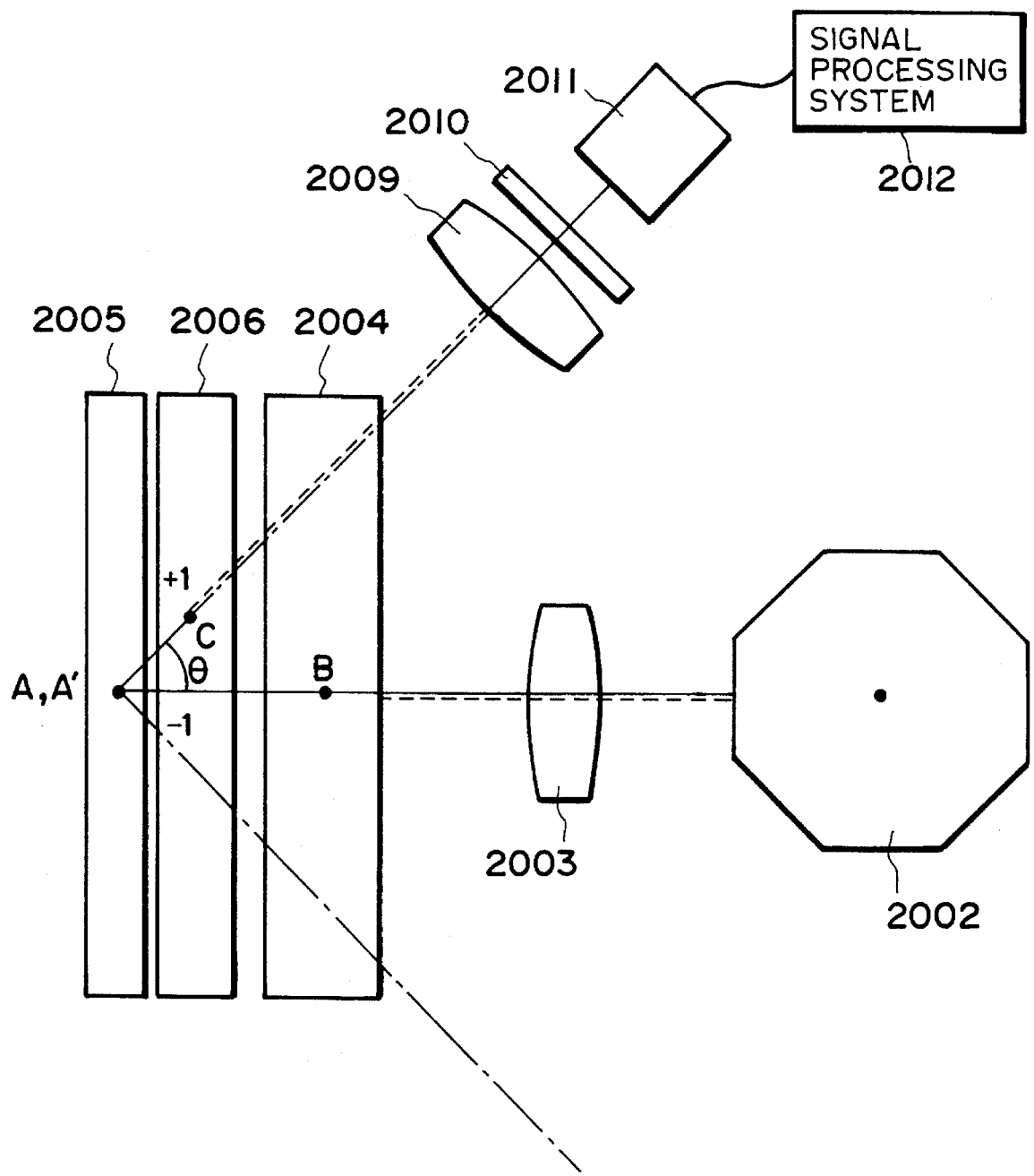
FIG. 44 is a schematic plan view of the nineteenth embodiment of the present invention.

FIGS. 43 and 44 show the structure of an inspection apparatus according to a nineteenth embodiment of the present invention, wherein FIG. 43 is a side view and FIG. 44 is a top plan view. In these drawings, denoted at 2001 is a light source device for producing two parallel laser beams having different wavelengths and different polarization directions. Denoted at 2002 is a polygonal mirror and denoted at 2003 is an f-θ lens system, which cooperate with each other to provide a scanning optical system for scanningly deflecting the laser beams from the light source device 2001. Denoted at 2004 is a mirror, denoted at 2005 is a diffraction grating and denoted at 2006 is a half mirror for combining scattered light from the surface, being inspected, and a reference light from the diffraction grating 2005. These elements 2004–2006 each has an elongated shape corresponding to the scan region. Denoted at 2007 is the surface to be inspected and, in this example, this is the surface of an original (reticle or photomask) on which a circuit pattern of a semiconductor device or devices is formed. Denoted at 2008 is a stage for carrying thereon and moving the original in a predetermined direction as denoted by an arrow in the drawing. Denoted at 2009 is a condensing lens for collecting scattered light, denoted at 2010 is a polarization plate for transmitting only light of a predetermined polarization component (P-polarized component, in this example), and denoted at 2011 is a photoelectric detector (photo-multiplier) for detecting interference light. The elements 2009–2011 cooperate with each other to provide a detection optical system. Denoted at 2012 is a signal processing system for discriminating the state of the surface, being examined, on the basis of the output of the photoelectric detector 2011.

The light source device 2001 produces a P-polarized laser beam of a frequency $w_1$ and an S-polarized laser beam of a frequency $w_2$, directed in parallel to each other. More specifically, it is arranged so that a dual-frequency laser beam from a dual-frequency Zeeman laser light source, as having a predetermined frequency difference and having orthogonally intersecting directions of polarization, is separated into a P-polarized laser and an S-polarized laser by means of a polarization beam splitter, for example. Alternatively, one or two acousto-optic devices may be used to frequency-modulate two laser beams. As a further alternative, injection current to a semiconductor laser may be controlled to provide laser beams of two different frequencies.

The two parallel laser beams produced by the light source device 2001 are directed to the scanning optical system which comprises the polygonal mirror 2002 and the f-θ lens system 2003. Of these two laser beams, one 2013a (S-polarized light with a frequency $w_2$) is projected on a point A on the surface 2007 being examined, to scan the surface one-dimensionally in a particular direction. Simultaneously, the surface 2007 is displaced by the stage 2008 in a direction perpendicular to the particular direction. As a result, the surface 2007 is scanned two-dimensionally.

When the light 2013a is incident on the surface 2007 and if there is a particle or defect or, alternatively, a circuit pattern at the position being irradiated, the S-polarized light 2013a is depolarized by such a particle or defect to produce scattered light (P-polarized light and S-polarized light) or the light 2013a is scattered by the circuit pattern to produce scattered light (mainly consisting of S-polarized light). Here, the reason why the light is depolarized by a particle or defect may be that: generally, the surface of such a particle or defect is rough and, therefore, polarization is disturbed when the light is irregularly reflected and scattered by that surface such that a polarization component different from the plane of polarization of the light as the same is inputted is generated. As compared therewith, if the light is scattered by an object such as a circuit pattern, having a relatively even and flat surface, depolarization is small.

Figure 45:
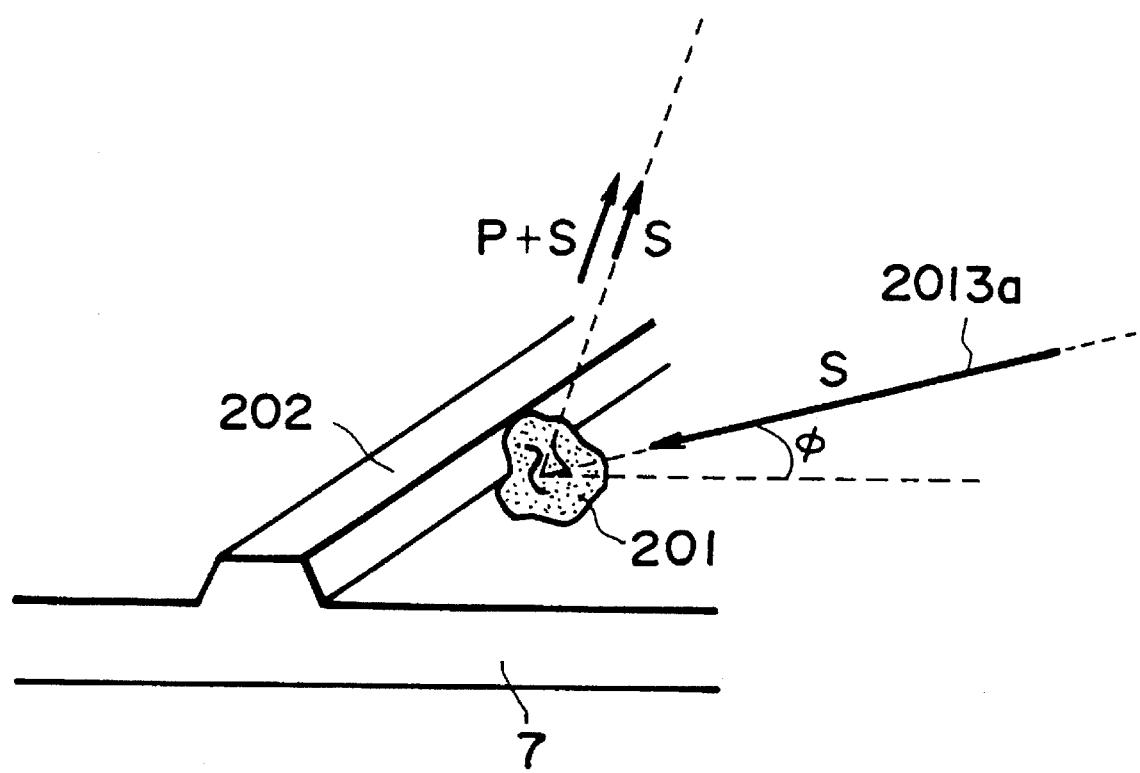
FIG. 45 is a schematic view for explaining the generation of scattered light from the surface being inspected.

FIG. 45 is an enlarged view, illustrating presence of a particle and a circuit pattern in the neighborhood of a scanning spot. Denoted at 201 is a particle of a size of about 0.3 micron, adhered to the surface 7. Denoted at 202 is a circuit pattern. As the S-polarized light 2013a is projected on the surface with an angle of incidence of φ, it is depolarized by the particle 201 and, thus, scattered light of P- and S-polarized components is produced isotropically from the particle 201. Also, non-depolarized (or little depolarized) scattered diffraction light of S-polarization is produced from the circuit pattern 202. Thus, by arranging the system so that the direction for the detection of the scattered light is placed in such direction along which no diffraction light comes from the circuit pattern 202, it is possible to improve the S/N ratio. This direction for the detection of scattered light may be determined as desired on the basis of the positional relationship among the mirror 2004, the diffraction grating 2005 and the half mirror 2006 as well as the pitch of the diffraction grating 2005 (to be described later). In this embodiment, the system is arranged so as to detect the scattered light being scattered backwardly and sidewardly of the input light 2013*a*. However, the system may be modified so as to detect the scattered light being scattered forwardly and sidewardly of the input light or being scattered sidewardly at a right angle: in such sideward direction only small diffraction light comes from the circuit pattern.

Referring back to FIGS. 43 and 44, the other 2013*b* (P-polarized light with a frequency $w_1$) of the light beams scanningly deflected by the scanning optical system, is reflected at a point B on the mirror 2004 and is directed to a point A' on the diffraction grating 2005. Then, from the point A', diffraction light is produced at a predetermined diffraction angle. This diffraction angle θ is determined in accordance with the following equation:

$$P\sin\theta = \pm m\lambda$$

where P is the pitch of the diffraction grating, θ is the diffraction angle, λ is the wavelength and m is the order of diffraction.

In this embodiment, of the diffraction light emanating from the diffraction grating 5 at a diffraction angle θ, positive first-order diffraction light 2014 (frequency $w_1$) is used as a reference light. This positive first-order diffraction light 2014 is reflected at a point C on the half mirror 2006 toward the detection optical system. Here, the point A' of light incidence upon the diffraction grating 2005 and the point A of light incidence upon the surface 2007 are in an optically conjugate relationship with each other. As a result, both the positive first-order diffraction light (reference light) 2014 from the diffraction grating 2005 and the scattered light from the surface 2007, being examined, are collected by the condensing lens 2009. Then, by means of the polarization plate 2010, only the P-polarized component is selected. Thus, due to heterodyne interference between the reference light (P-polarized light with a frequency $w_1$) and the light wave (P-polarized light with a frequency $w_2$) among the scattered light and being depolarized by the particle or defect, a beat of a frequency $\Delta w$ ($=|w_2-w_1|$) is produced. This beat is detected as a beat signal by the photoelectric detector 2011 and, on the basis of which, the particle or defect is detected by the signal processing system 2012 while being discriminated from a circuit pattern.

The particle/defect detection in this embodiment is based on the fact that: such a component of the scattered light that can be transformed into a beat signal through optical heterodyne interference is only the P-polarized light component which is the resultant of depolarization; and even if scattered light from a circuit pattern is contained, it mainly consists of an S-polarized light component which does not participate in the optical heterodyne interference and thus cannot be transformed into a beat signal by the photoelectric detector 2011. This means that only the scattered light from a particle or defect is detected as a beat signal and that, even if there is scattered light from a circuit pattern, it is not transformed into such a beat signal (even if it is so transformed, the produced beat is very low). In this manner, the inspection system of this embodiment assures a very high sensitivity and a very high S/N ratio for the particle/defect inspection.

It is to be noted here that the optical structure as described hereinbefore may be modified so that the relationship between lights of S-polarization and P-polarization is inverted. Similar particle or fault detection is possible with such a modified structure.

Embodiment 20

Figure 46:
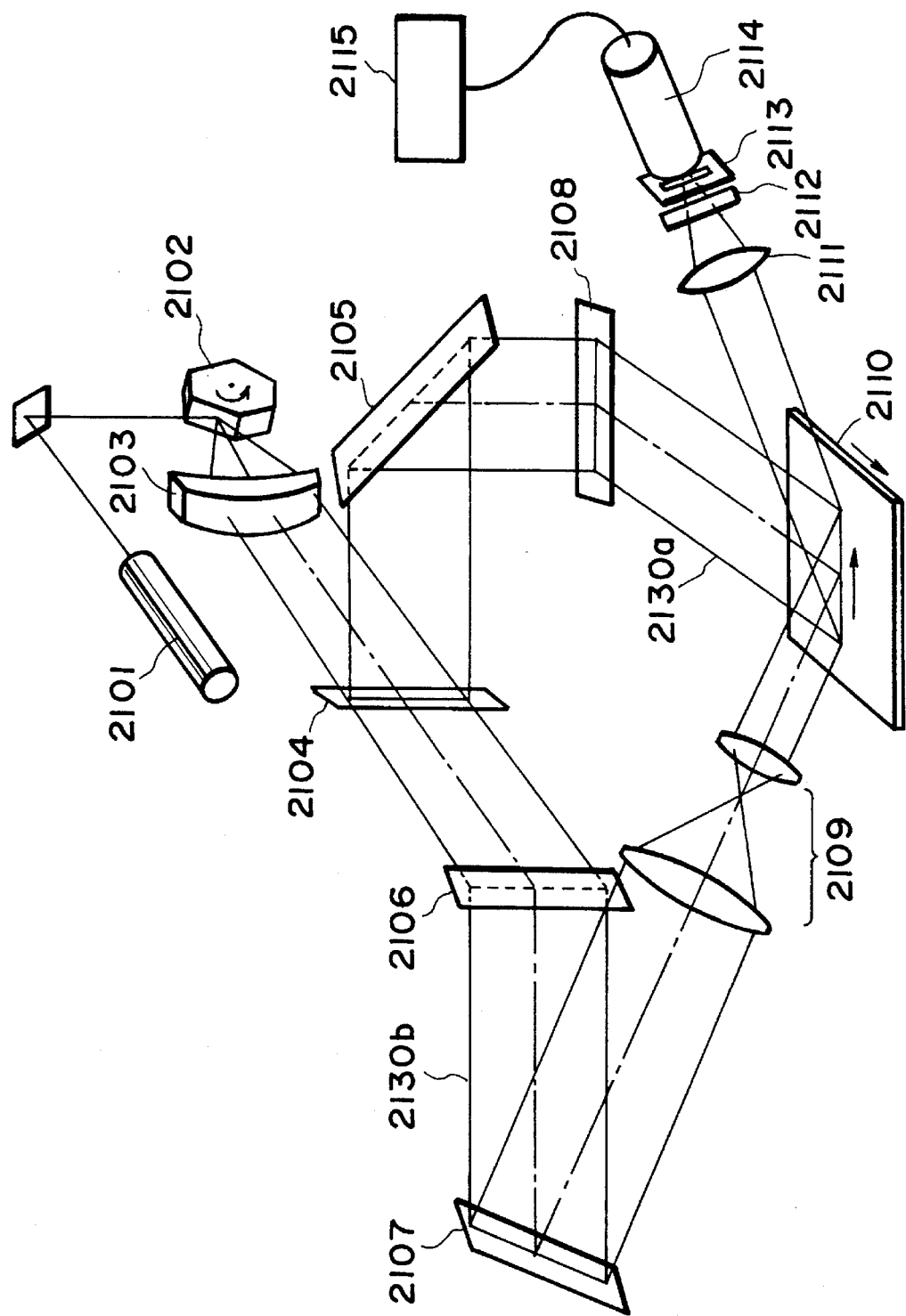
FIG. 46 is a schematic perspective view of a twentieth embodiment of the present invention.
Figure 47:
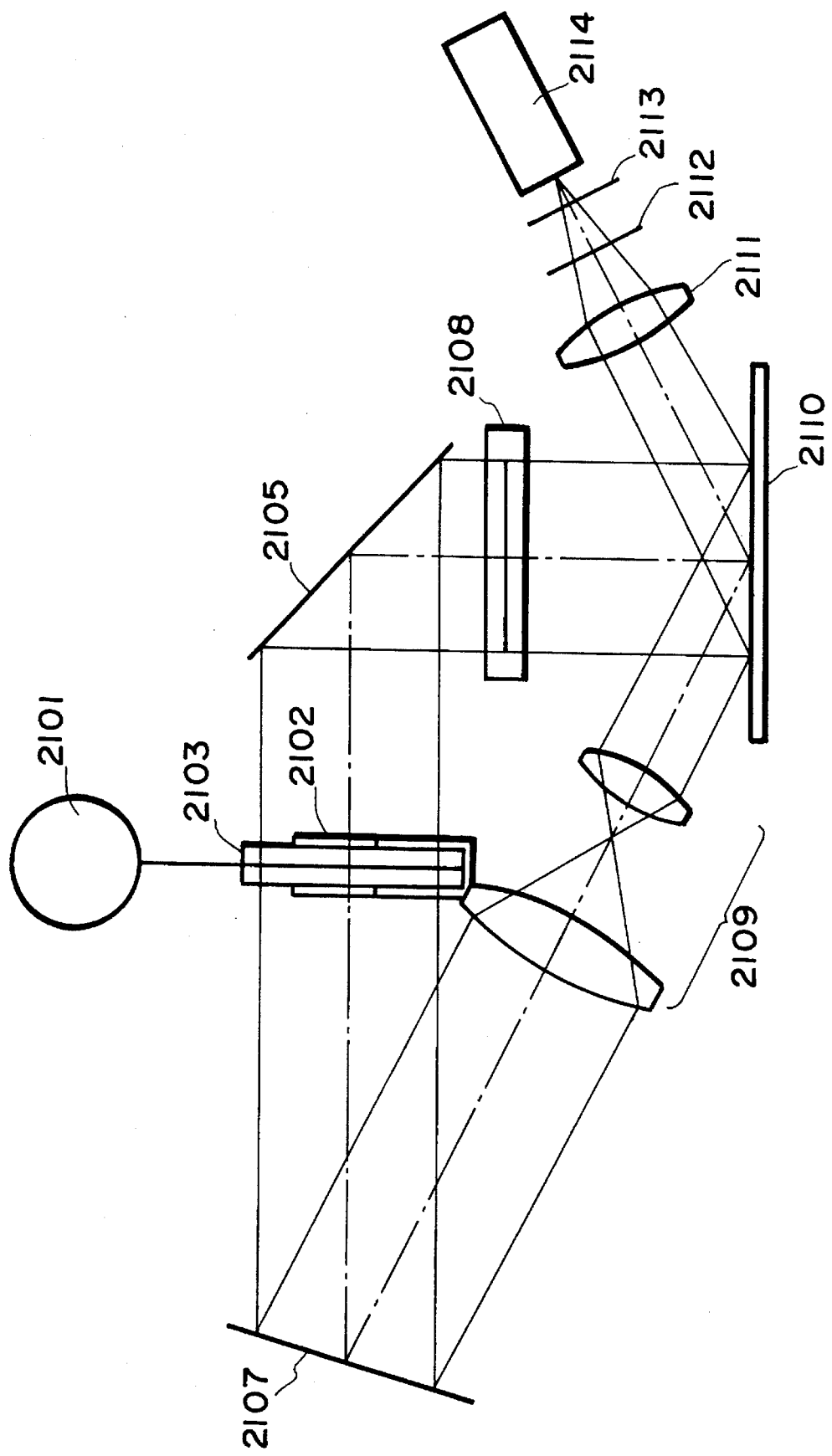
FIG. 47 is a schematic front view of the twentieth embodiment of the present invention.
Figure 48:
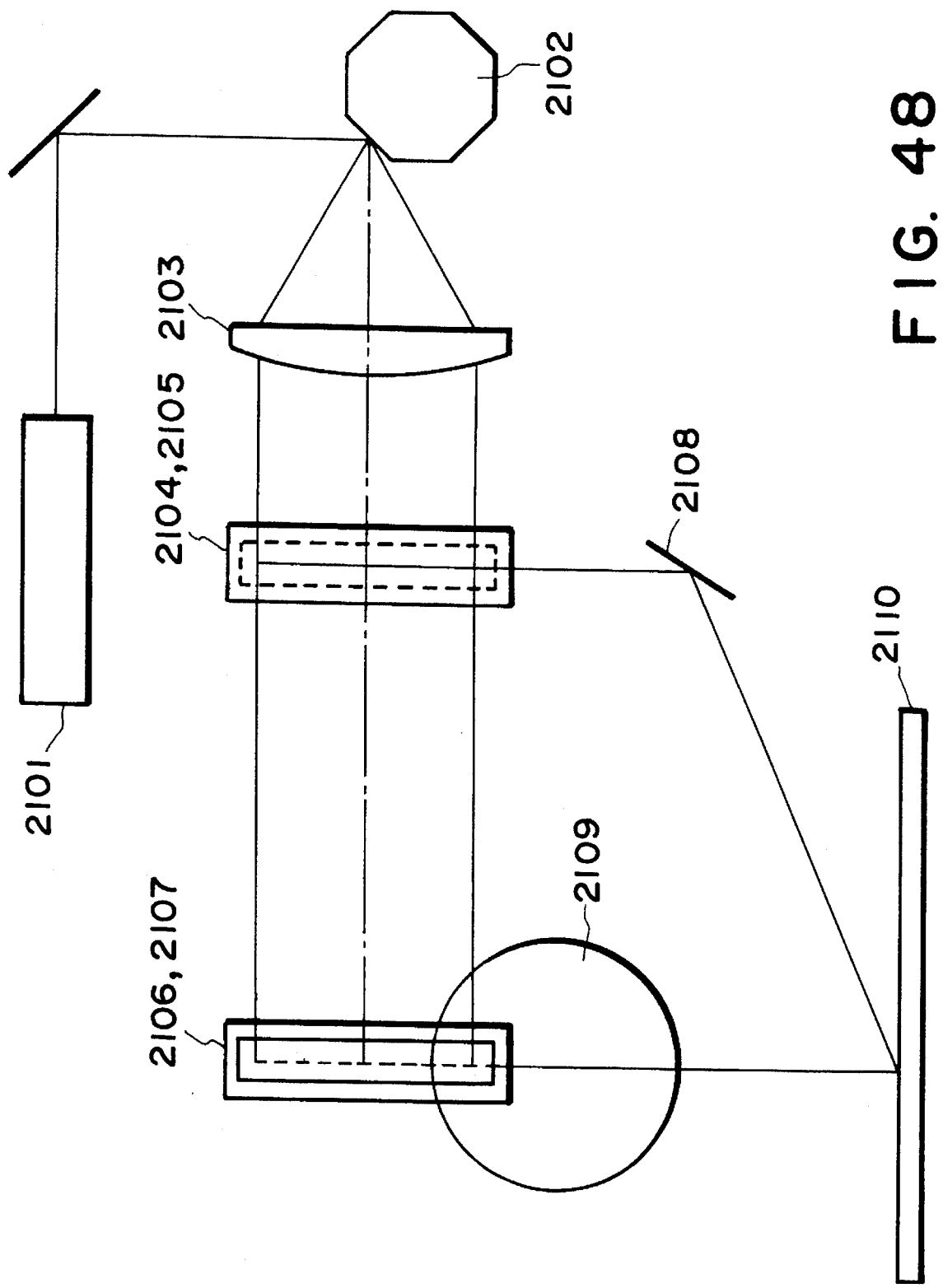
FIG. 48 is a schematic side view of the twentieth embodiment of the present invention.
Figure 49:
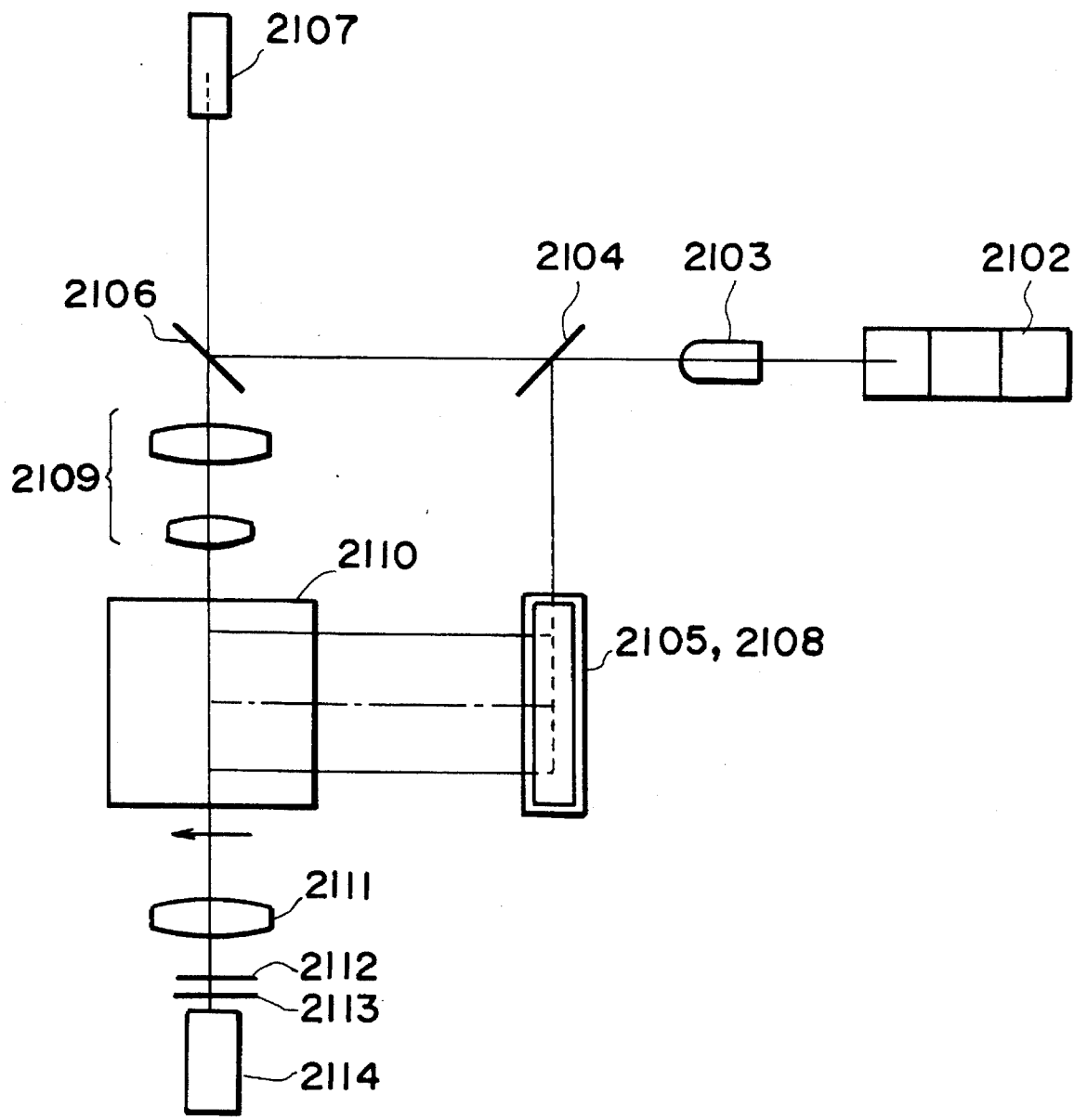
FIG. 49 is a schematic plan view of the twentieth embodiment of the present invention.

A twentieth embodiment of the present invention will be described with reference to FIGS. 46–49, wherein FIG. 46 is a perspective view showing the general structure of the twentieth embodiment and FIGS. 47, 48 and 49 are a front view, a side view and a plan view of the twentieth embodiment, respectively.

Denoted at 2101 is a light source device which, like the light source device 2001 of the nineteenth embodiment, produces a P-polarized laser beam of a frequency $w_1$ and an S-polarized laser beam of a frequency $w_2$, superposed one upon another on the same optical axis. Denoted at 2102 is a polygonal mirror and denoted at 2103 is an f-θ lens system, which cooperate with each other to provide a scanning optical system. Denoted at 2104 is a polarization beam splitter and denoted at 2105, 2106, 2107 and 2108 are mirrors, respectively, each having an elongated shape corresponding to the scan range. Denoted at 2109 is an afocal converter for changing the width of scan by the scanning light. Denoted at 2110 is the surface to be inspected, and this surface can be displaced in a direction intersecting the direction of scan by the scanning light. Denoted at 2111 is a condensing lens for collecting the combined wave of (i) scattered light, from the surface 2110 being examined, of the light 2130*a* scanningly deflected through the mirror 2108 and scanning the surface 2110 and (ii) reference light from the afocal converter 2109 and reflectively scattered by the surface 2110. Denoted at 2112 is a polarization plate for registering the plane of polarization, for the purpose of detection of a heterodyne signal. Denoted at 2113 is an aperture having a rectangular opening corresponding to the scan range, for suppressing DC components of the heterodyne signal. Denoted at 2114 is a photoelectric detector (photo-multiplier), and denoted at 2115 is a signal processing system.

The laser beam from the light source device 2101 is scanningly deflected by the scanning optical system which comprises the polygonal mirror 2102 and the f-θ lens system 2103. The polarization beam splitter 2104 transmits a P-polarized light component (frequency $w_1$) and reflects an S-polarized light component (frequency $w_2$), and thus it separates the laser beam into two beams. Of these two laser beams, the reflected light 2130*a* is then deflected by two mirrors 2105 and 2108, such that it is projected on the surface 2110, to be inspected, along a predetermined direction to scan the same one-dimensionally.

On the other hand, the light 2130*b* scanningly deflected by the scanning optical system and then transmitted through the polarization beam splitter 2104, is deflected by two mirrors 2106 and 2107 toward the afocal converter 2109. The afocal converter reduces the scan range of the light 2130*b* and, additionally, reverses the direction of scan. The resultant light is projected on the surface 2110, along a direction different from the direction of projection of the light 2130*a* (perpendicular thereto as viewed from above). Here, under the influence of the afocal converter 2109, the light 2130*a* and the light 2130*b* are superposed one upon another on the surface 2110, such that at any moment during the scanning period these two lights scan the same point on the surface 2110.

When the light 2130a (S-polarized light with a frequency $w_2$) is incident on the surface 2110 and if there is a particle or defect or, alternatively, a circuit pattern at the position being irradiated, the S-polarized light 130a (frequency $w_2$) is depolarized by such a particle or defect to produce scattered light (P-polarized light and S-polarized light) or the light 2130a is scattered by the circuit pattern to produce scattered light (mainly consisting of S-polarized light). Here, the reason why the light is depolarized by a particle or defect may be that: generally, the surface of such a particle or defect is rough and, therefore, polarization is disturbed when the light is irregularly reflected and scattered by that surface such that a polarization component different from the plane of polarization of the light as the same is inputted is generated. As compared therewith, if the light is scattered by an object such as a circuit pattern, having a relatively even and flat surface, depolarization is small.

The detection optical system which comprises the condensing lens 2111 is disposed in the direction of zeroth order light caused by the light 130b (P-polarized light of a frequency $w_1$) projected to the surface 2110. Also, the light 2130a (S-polarized light of frequency $w_2$) is incident on the same point upon the surface 2110, but in a direction different (by 90 deg.) from the direction of the light 2130b. As a result, there are produced (from the same point on the surface 2110) a reference light (substantially of P-polarization) from the light 2130b and containing zeroth order light as well as sideward (90 deg.) scattered light (S-polarization and P-polarization) from the light 2130a. Both of the thus produced lights enter the condensing lens 2111. Then, by means of the polarization plate 2112, only the P-polarized component is selected. Thus, due to heterodyne interference between the reference light (P-polarized light with a frequency $w_1$) and the light wave (P-polarized light with a frequency $w_2$) among the scattered light from the light 2130a and being depolarized by the particle or defect, a beat of a frequency $\Delta w$ ($=|w_2-w_1|$) is produced. This beat is detected as a beat signal by the photoelectric detector 2114 and, on the basis of which, the particle or defect is detected by the signal processing system 2115 while being discriminated from a circuit pattern in the same manner as the first embodiment.

Figure 50:
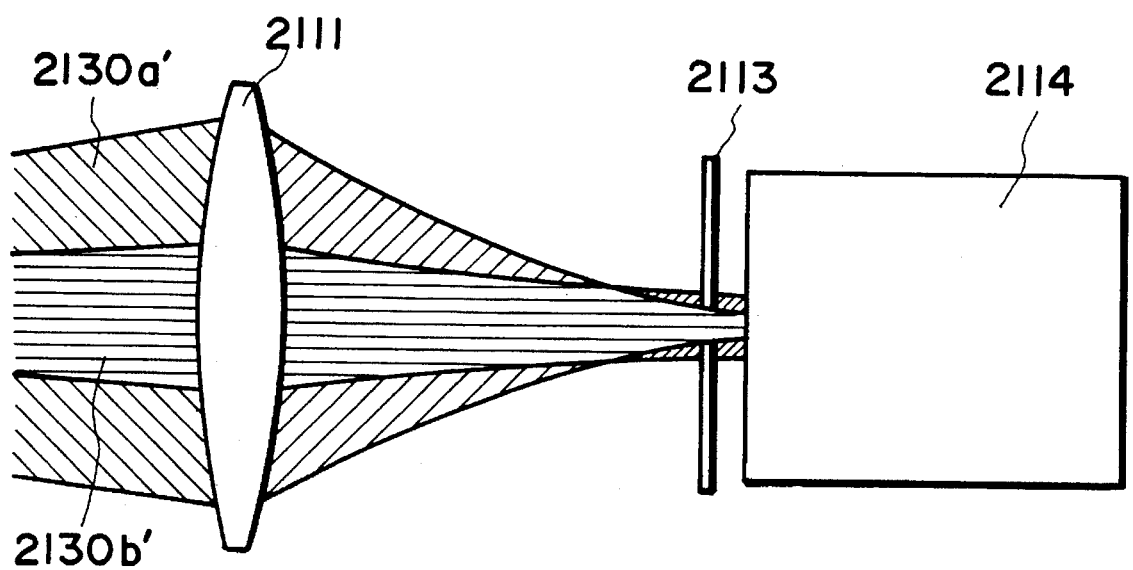
FIG. 50 is a schematic view for explaining the function of an aperture of the twentieth embodiment.
Figure 51:
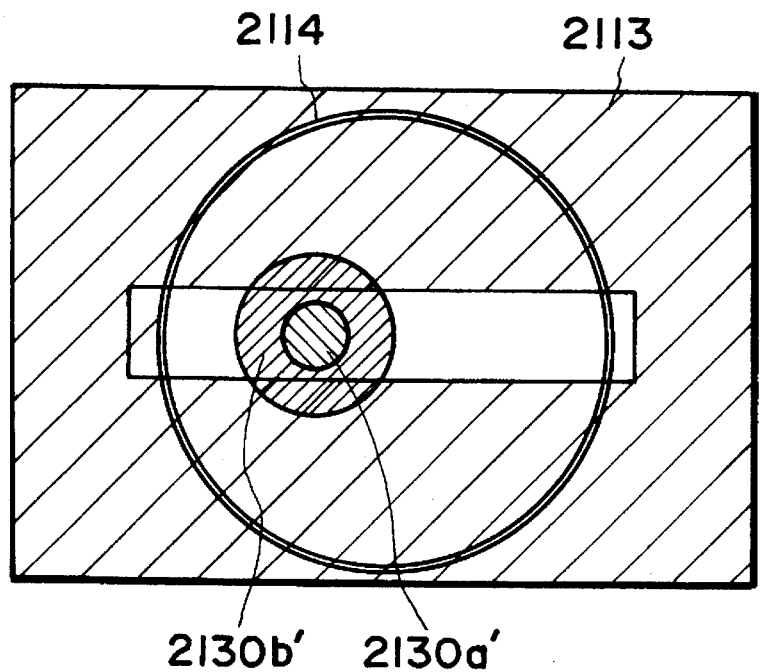
FIG. 51 is a schematic view for explaining the function of the aperture of the twentieth embodiment.

FIGS. 50 and 51 are schematic views for explaining the function of an aperture 2113 which is disposed between the condensing lens 2111 and the photoelectric detector 2114. FIG. 50 is a side view and FIG. 51 is a view as seen on the optical axis. The scattered light produced laterally widely as a result of irradiation of a particle or defect upon the surface, being examined, with the light 2130a is projected upon the whole diameter of the condensing lens 2111, as depicted at 2130a'. On the other hand, since the light 2130b is reflectively scattered by the surface being examined, it is not diverged so widely and is projected upon a limited portion of the diameter of the condensing lens 2111, as depicted at 2130b'. Thus, they have different numerical apertures (NAs). Consequently, on the detection surface (photoelectric detection surface) of the photoelectric detector 2114 upon which these lights are converged, the converged lights have different light spot diameters. This leads to that, in a portion other than the overlapping portion (interfering portion) of the converged light spots, these lights do not interfere with each other and, as a result of which the AC component of the beat signal is reduced. In consideration of such an inconvenience, in the present embodiment an aperture 2113 is disposed along the scan range so as to block an unnecessary portion of the reference light 2130b' to ensure an increase in the S/N ratio.

While this embodiment is arranged so as to detect scattered light, scattered sidewardly by 90 deg., the structure may be modified so as to detect light scattered forwardly and sidewardly or scattered backwardly and sidewardly (in such sideward direction, only small diffraction light comes from a circuit pattern).

Embodiment 21

Figure 52:
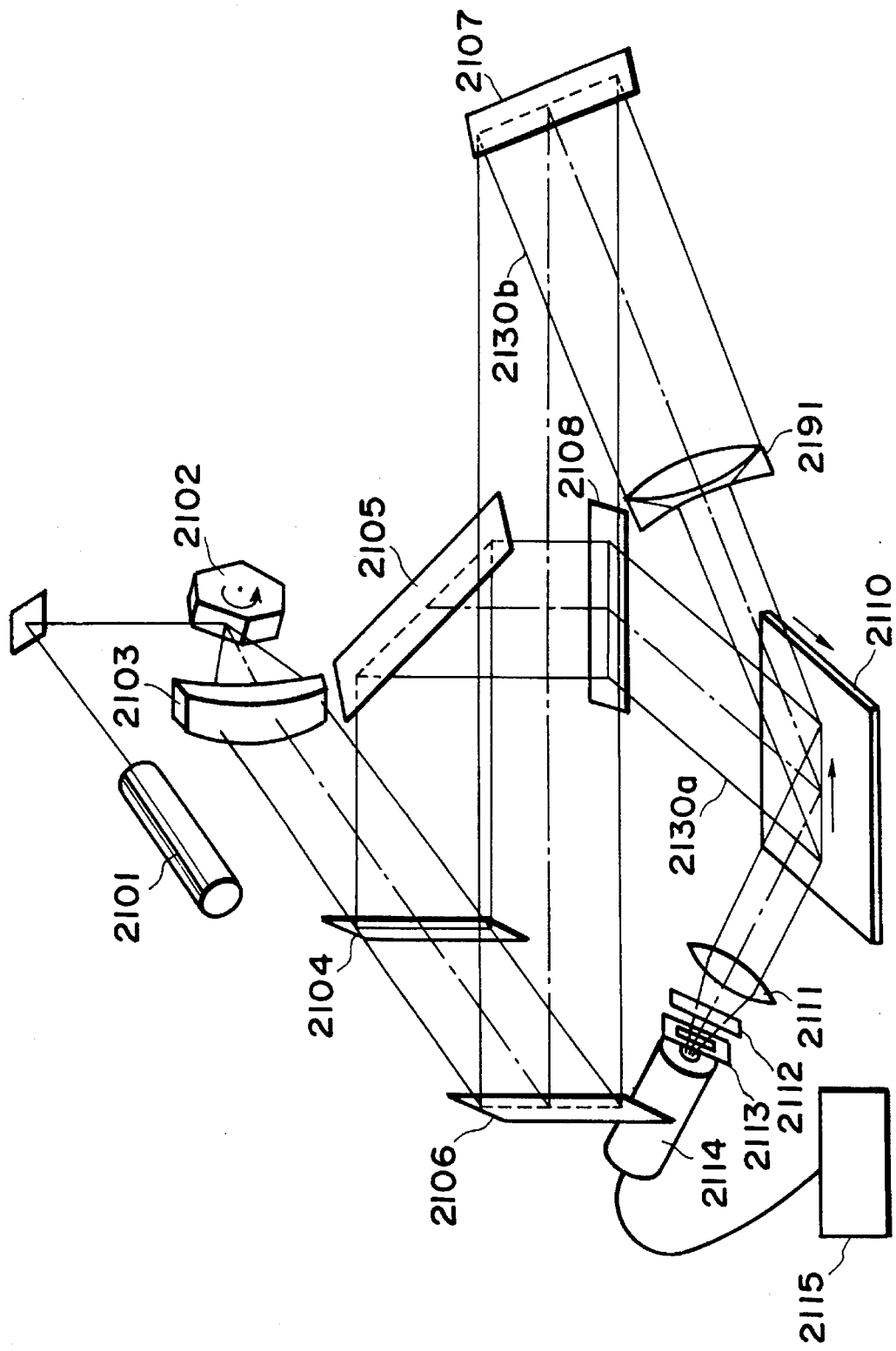
FIG. 52 is a schematic perspective view of a twenty-first embodiment of the present invention.

FIG. 52 shows a twenty-first embodiment which corresponds to a partially modified form of the twentieth embodiment. The principle of detection is basically the same as that of the second embodiment. In the structure of FIG. 52, the position of the mirror 2107 with respect to the optical system shown in FIG. 46 is changed to widen the flexibility with respect to the placement of the afocal converter 2191. Since in the afocal converter 2191 of this embodiment it is not necessary to reverse the scan direction, it comprises a combination of a convex lens and a concave lens, rather than a combination of two convex lenses such as shown in FIG. 46.

Embodiment 22

Figure 53:
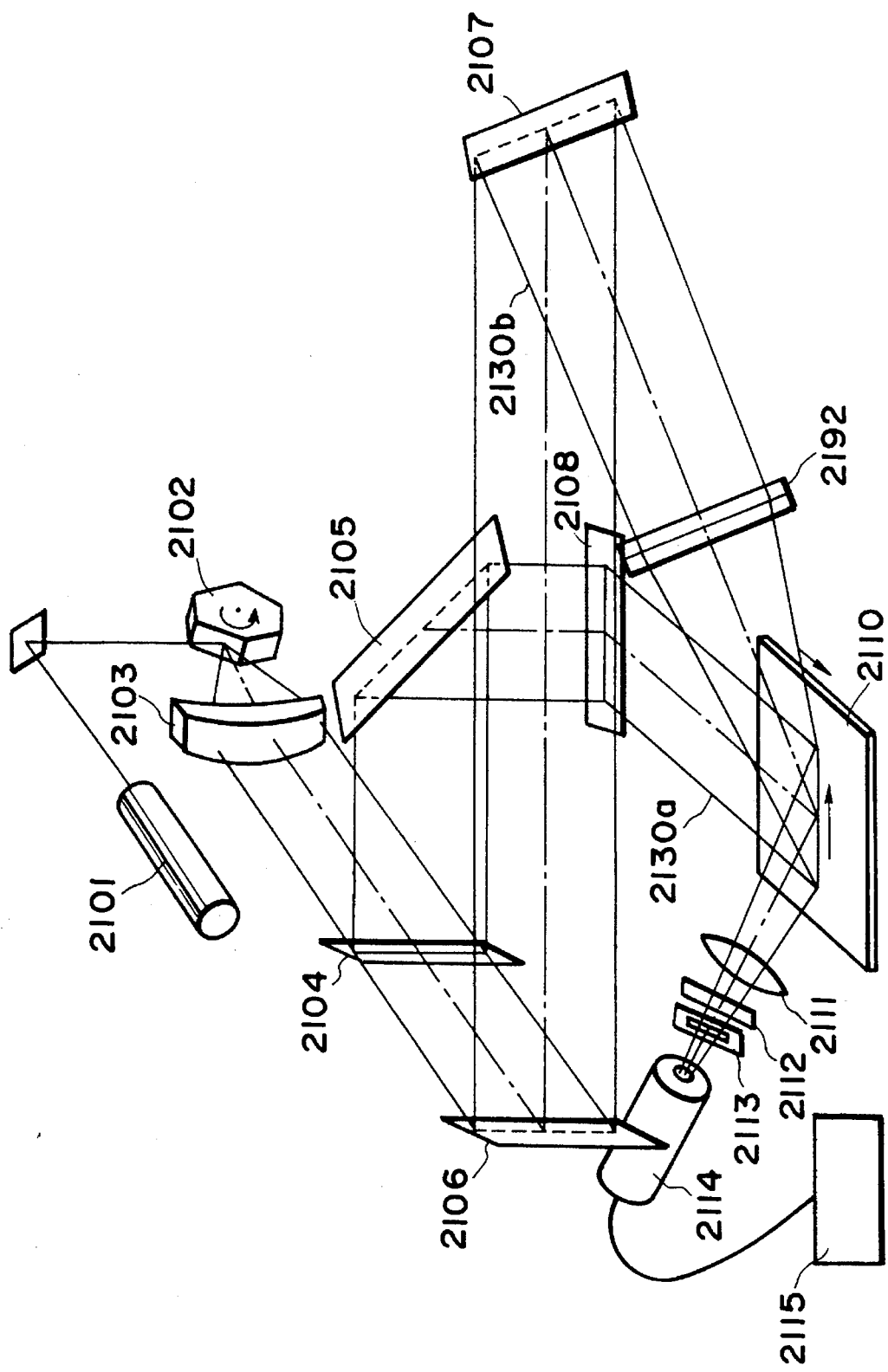
FIG. 53 is a schematic perspective view of a twenty-second embodiment of the present invention.

FIG. 53 shows a twenty-second embodiment which corresponds to a modified form of the twenty-first embodiment. In this embodiment, a hologram 2192 is used in place of the afocal converter 2191 of FIG. 52. The hologram 2192 is a physical optic element having a function for transforming an input wavefront of a received input light into a predetermined wavefront, and the hologram 2192 is disposed so that light is continuously converged on the locus of scan on the surface 2110. This assures substantially the same advantageous results as attainable with the third embodiment.

Embodiment 23

Figure 54:
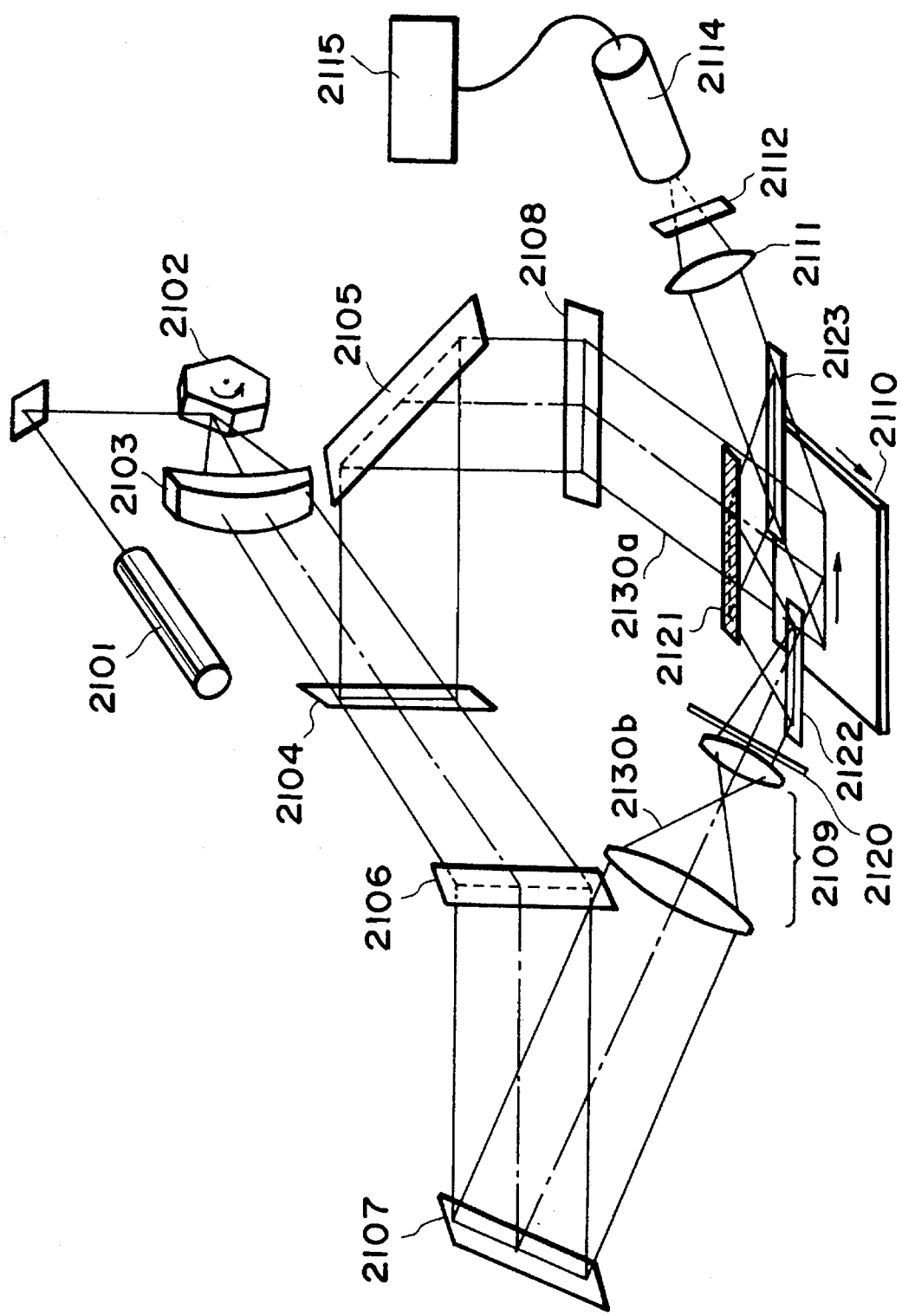
FIG. 54 is a schematic perspective view of a twenty-third embodiment of the present invention.
Figure 55:
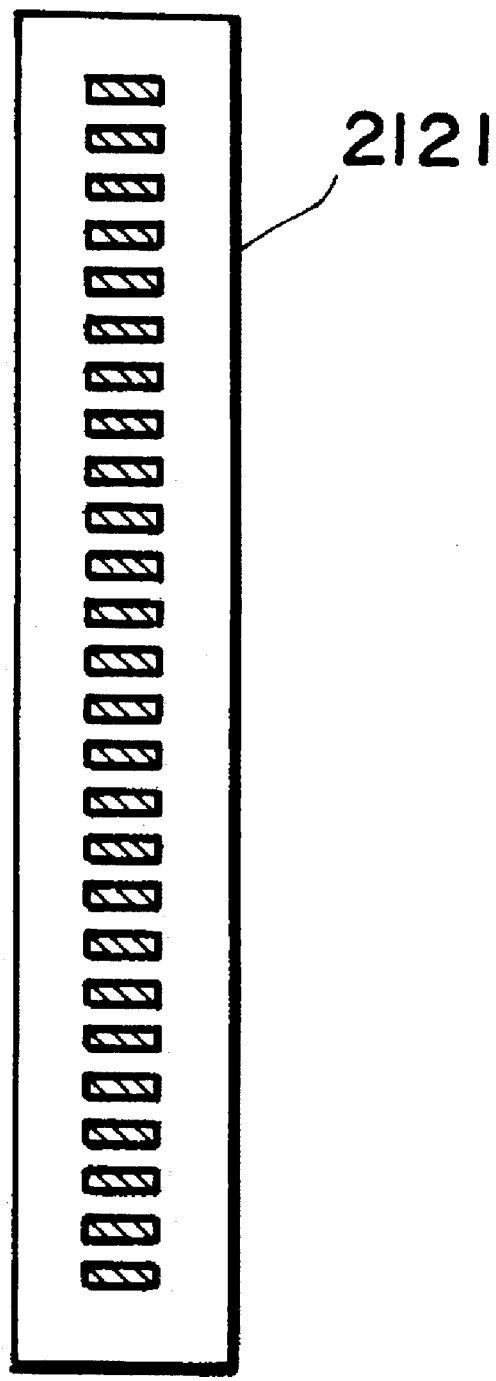
FIG. 55 is an enlarged view of a light scattering structure used in the twenty-third embodiment.

FIG. 54 shows a twenty-third embodiment, and like numerals as those of FIG. 46 are assigned to corresponding elements. In this embodiment, the light 2130b is not projected on the surface to be examined but is directly combined with the scattered light. Denoted in the drawing at 2120 is a $\lambda/2$ plate, denoted at 2121 is a light scattering structure, denoted at 2122 is a mirror, and denoted at 2123 is a half mirror. The light 2130b passed through the afocal converter 2109 goes through the $\lambda/2$ plate, by which the direction of polarization thereof changes. This polarization direction is coordinated with that of the polarization plate 2112. The light from the $\lambda/2$ plate is reflected by the mirror 2122 and is projected on the scattering structure 2121. The scattering structure 2121 has such an arrangement, as shown in FIG. 55, for example, wherein a glass substrate is patterned with a plurality of patterns of Cr material, for example, in the manner that their edges lie in the scan direction. It serves to produce scattered light, widely in predetermined directions. The light scattered by the pattern of the scattering structure 2121 enters the half mirror 2123. On the other hand, the sideward scattered light from a particle, produced as a result of irradiation with the light 2130a, also enters the half mirror 2123. Thus, by the half mirror, these lights are combined with each other. Here, the point of convergence of the light 130a, impinging on the surface being examined, and the point of irradiation on the scattering structure 2121 being irradiated with the light 2130b are in an optically conjugate relationship with each other with respect to the half mirror 2123.

Since in this embodiment the light which then provides the reference light is widely scattered by the scattering structure 2121, there is only a small difference between the light spot diameters of the two lights as having been described with reference to FIGS. 50 and 51. Thus, even with the omission of the aperture 113, it is possible to produce a beat signal of good quality.

Embodiment 24

Figure 56:
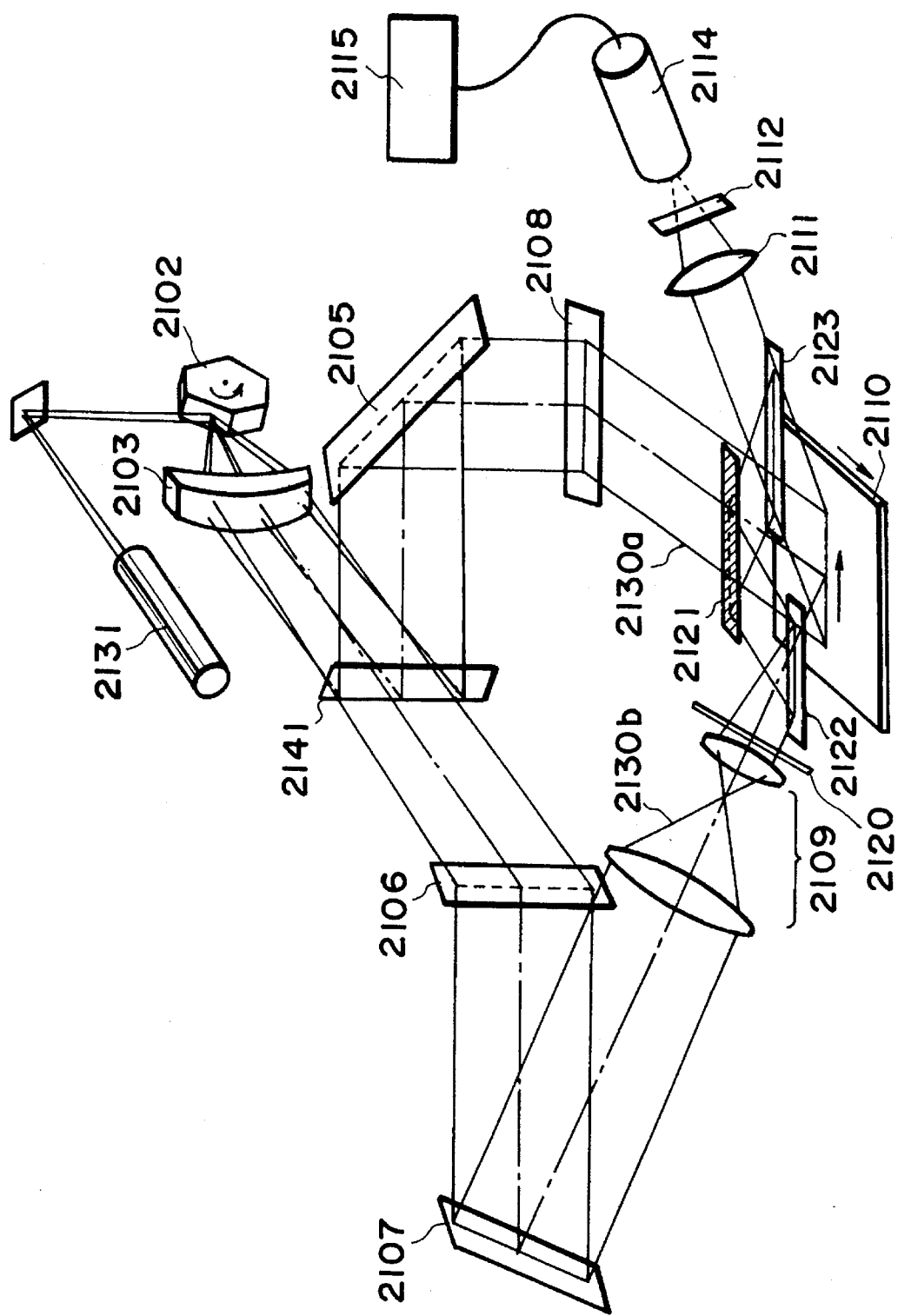
FIG. 56 is a schematic perspective view of a twenty-fourth embodiment of the present invention.

FIG. 56 shows a twenty-fourth embodiment which corresponds to a modified form of the twenty-third embodiment. As compared with the preceding embodiments, this embodiment uses a light source device 2131 which produces a P-polarized laser beam of a frequency $w_1$ and an S-polarized laser beam of a frequency $w_2$ and which emits them separately in parallel to each other, rather than in the form of a single beam. These two parallel light beams are scanned by a scanning optical system, and only one of them (i.e., only the S-polarized light of frequency $w_2$) is reflected by a reflection mirror 2141. The structure and function of the remaining portion of the inspection system are essentially the same as those of the embodiment of FIG. 54. Since in this embodiment it is not necessary to use a polarization beam splitter of elongated shape which is generally expensive, the cost of the inspection system can be reduced significantly.

Embodiment 25

Figure 57:
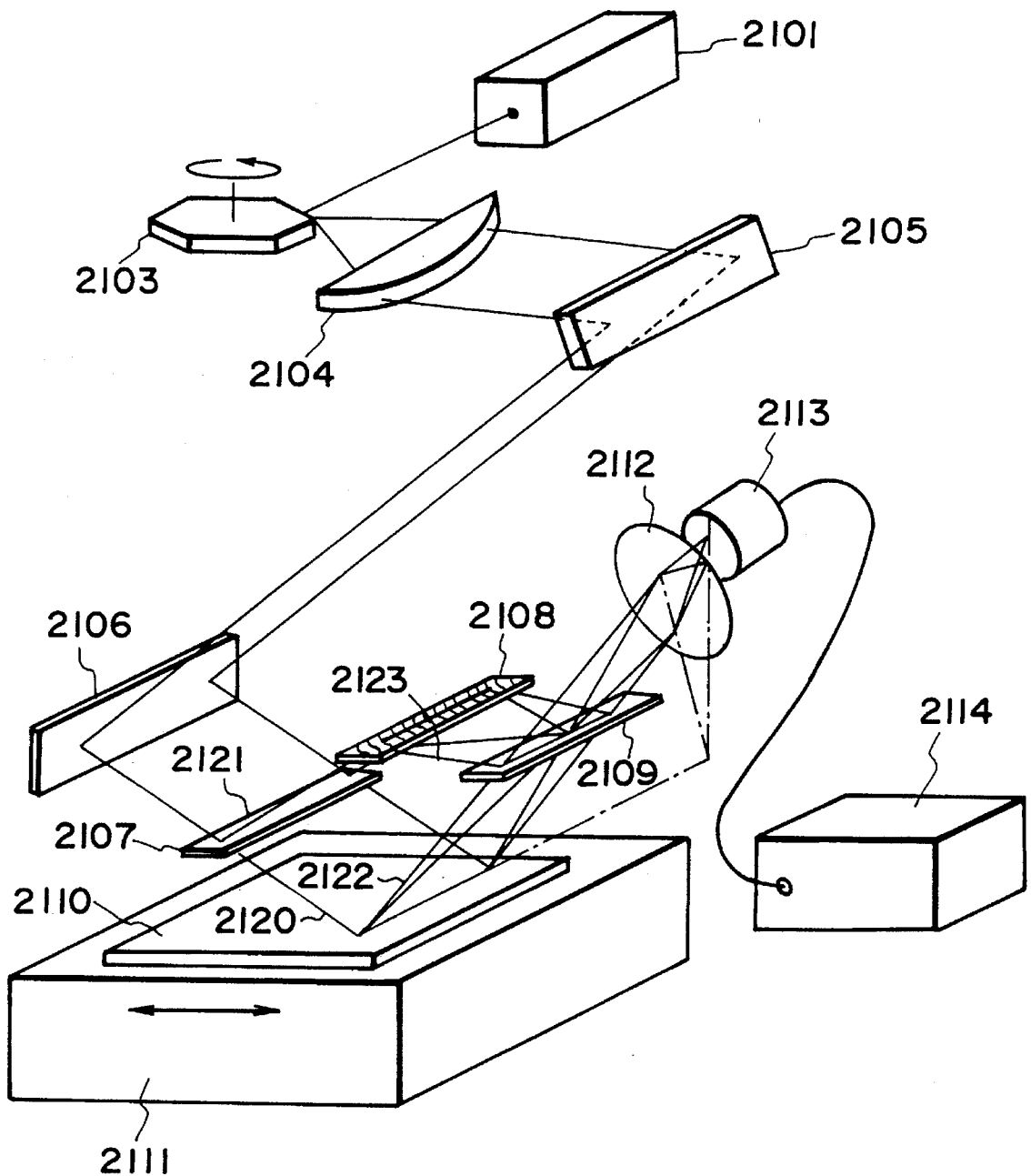
FIG. 57 is a schematic view of a twenty-fifth embodiment of the present invention.

FIG. 57 shows a twenty-fifth embodiment of the present invention. In the drawing, denoted at 2101 is a dual-frequency laser source such as a Zeeman laser, a semiconductor laser or an optical system using acousto-optic means. Denoted at 2103 is a scanning mirror; at 2104 is an f-θ lens; at 2105 and 2106 are reflection mirrors; at 2107 is a polarization beam splitter; at 2108 is a diffraction grating; at 2109 is a half mirror; at 2110 is the surface to be inspected; at 2111 is a scanning stage; at 2112 is a condensing lens; at 2113 is a photoelectric detector; and at 2114 is a beat signal processing system.

A laser beam from the dual-frequency laser source 2101 is directed by a scanning optical system comprising the scanning mirror 2103 and the f-θ lens 2104, whereby it is scanningly deflected. Then, it goes via the mirrors 2105 and 2106 and, by means of the polarization beam splitter 2107, it is subsequently divided into an S-polarized laser beam (shift frequency ω) 2020 and a P-polarized laser beam (shift frequency ω+Δω) 2121. The divided S-polarized laser beam 2120 is converged into a spot upon the surface 2110 to be inspected. Scattered rays from a particle/fault or a circuit pattern within the spot, providing side-scattered light 2122, are collected, after being passed through the half mirror 2109, by the condensing lens 2112 which is disposed sideways by approx. 90 deg. of the direction of incidence of the S-polarized laser beam 2120. On the other hand, the P-polarized laser beam 2121 is converged upon the diffraction grating 2108, by which diffraction light is produced. Here, the system is so arranged that, of the produced diffraction light, first order diffraction light 2123 is directed to the half mirror 2109. The half mirror 2109 then combines the first order diffraction light 2123 and the side scattered light 2122. The diffraction grating 2108 is so designed that it produces first order diffraction light sideways by approx. 90 deg. to the incident light such that, in accordance with the position of a light spot being displaced by the scanning optical system, the first order diffraction light is continuously combined with the side scattered light 2122 by the half mirror 2109. The P-polarized light component (being depolarized by a particle or fault) contained in the side scattered light 2122 and the first order diffraction light (P-polarized light component) from the diffraction grating 2108, having been combined by the half mirror 2109, are imaged through the condensing optical system 2112 upon the sensing surface of the photoelectric detector 2113 and they cause optical heterodyne interference. The resultant signal is processed by the beat signal processing system 2114.

While in this embodiment the sensing surface of the photoelectric detector 2113 is placed in a conjugate relationship with the spot on the surface 211o being inspected, it may be disposed upon a pupil plane. Further, the relationship between the P-polarized light and the S-polarized light may be inverted.

Figure 58A:
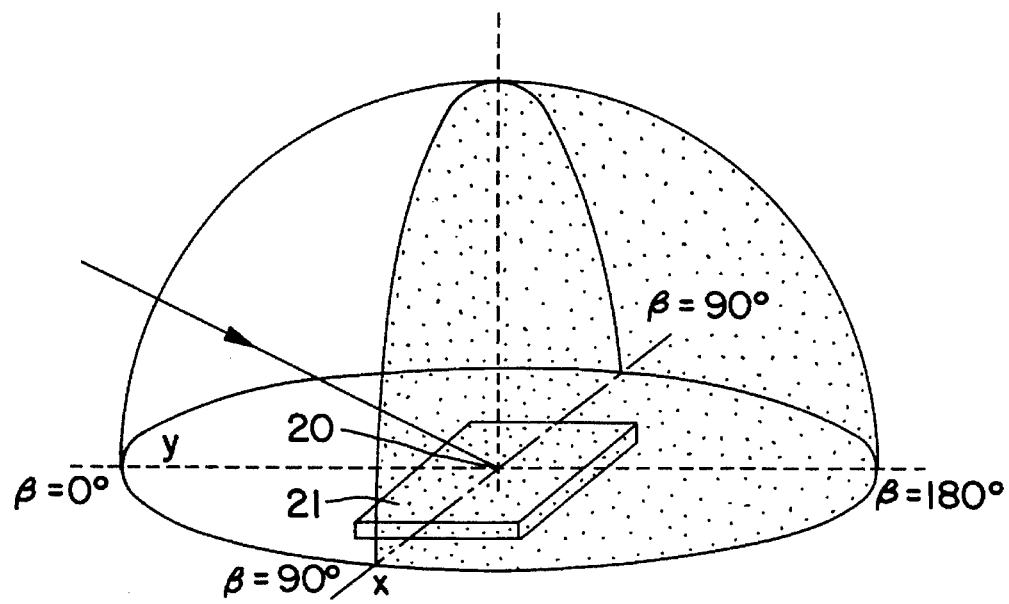
FIGS. 58A and 58B are schematic views each for explaining a preferable direction of detection for scattered light.
Figure 58B:
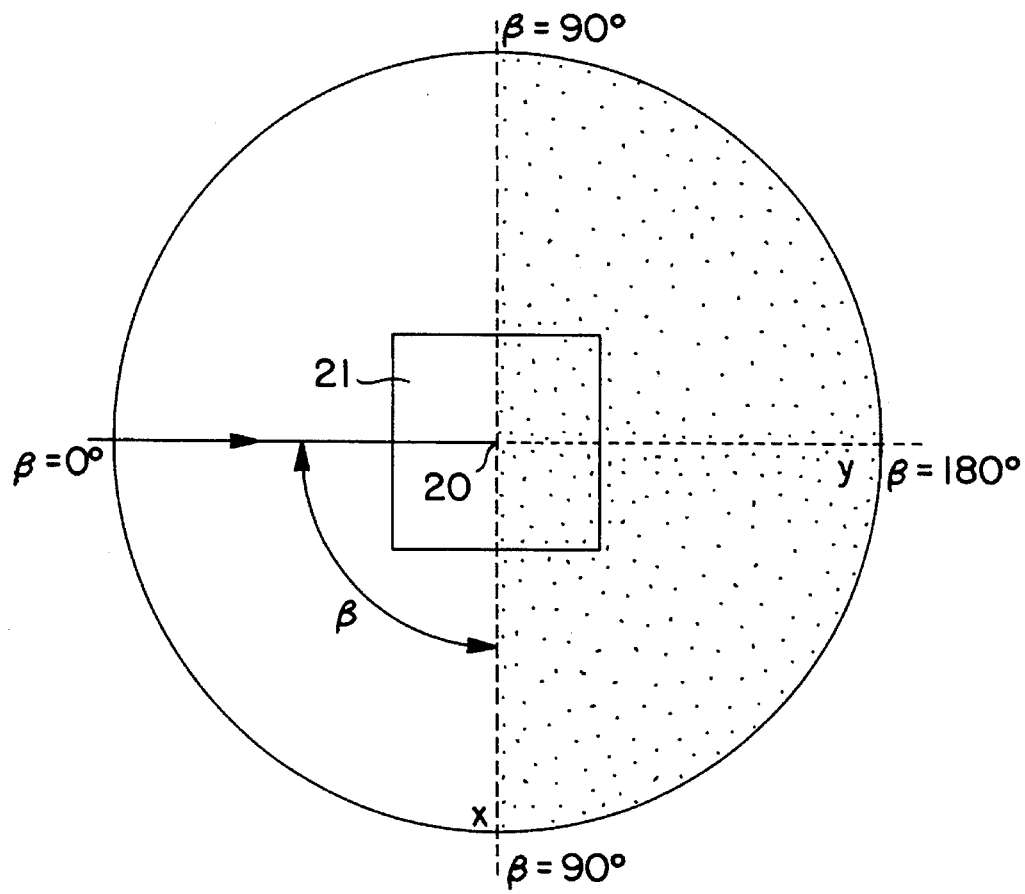

The nineteenth to twenty-fifth embodiments described hereinbefore are arranged to detect scattered light which advances sideways with respect to incident or input light. The inventors have examined a preferable detection angle in relation to a particle of a size of about 0.3 micron. From the results, it has been found that a high detection sensitivity is preferably obtainable if the photoelectric detector is so disposed that the angle β defined between orthogonal projection lines, being defined by projecting upon the surface to be inspected the input light and the light incident on the photoelectric detector, is within a range of 90–180 deg. In other words, it is preferable to dispose the photoelectric detector within a range as depicted by hatching in FIG. 58A or 58B.

Embodiment 26

Referring now to FIG. 59, a modified form of signal processing through the beat signal processing system of any of the preceding embodiments will now be explained. In the drawing, denoted at 401 is a preamplifier for amplifying a beat signal produced by the photoelectric detector. Denoted at 402 is an AC/DC separator for separating AC and DC components of the beat signal from each other. Denoted at 403 is a phase comparator; at 404 and 409 are low pass filters; at 405 is an amplifier for raising the loop gain; and at 406 is a voltage controlled oscillator; at 407 is a 90-deg. phase shifter for correcting a 90-deg. phase shift of an output signal of the voltage controlled oscillator 406. Denoted at 408 is a multiplier for performing multiplication to a beat signal and an output signal of the voltage controlled oscillator; and denoted at 410 is a peak correcting circuit for correcting the wave height of an output signal pulse of the low pass filter to thereby remove any effect of an intensity change in zeroth order diffraction light. Denoted at 411 is a zeroth order diffraction light monitoring circuit for monitoring any change in intensity of zeroth order light, based on a change in DC component of a beat signal. Denoted at 412 is a counter which serves to evaluate an output pulse of the peak correcting circuit to discriminate the presence of a particle or fault; and denoted at 413 is a computer which is operable to memorize or display the number or positions of particles or faults.

Figure 60A:
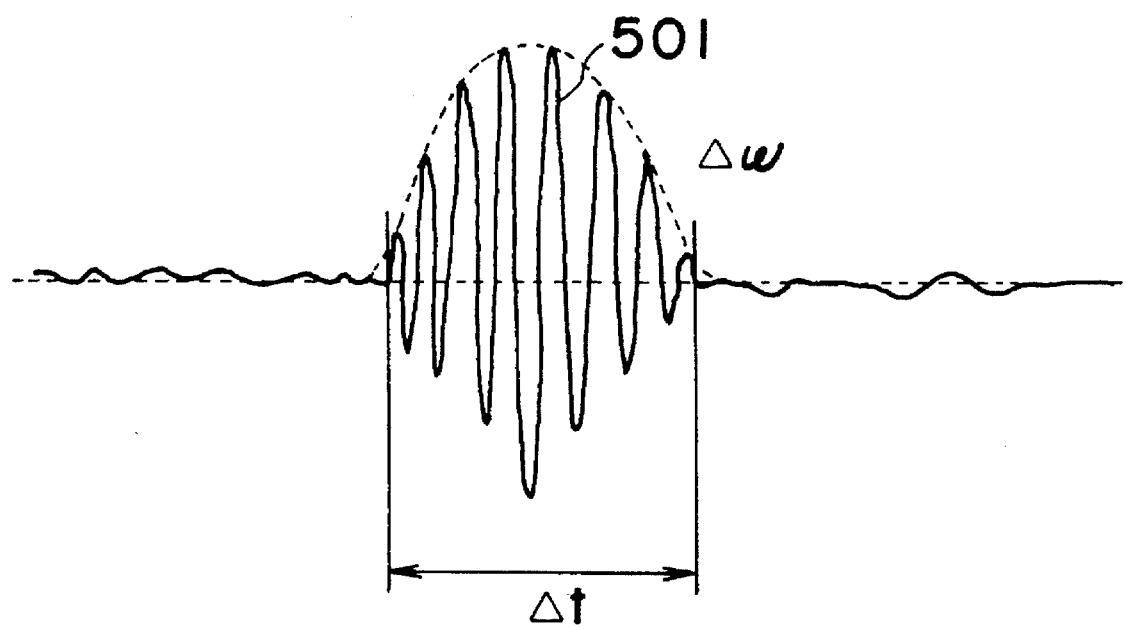
FIGS. 60A and 60B are schematic views each for explaining a beat signal detected.
Figure 60B:
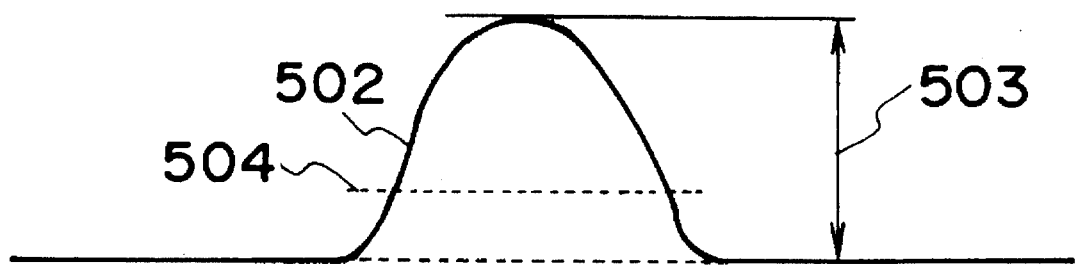

The signal processing operation in this signal processing system is made in the following sequence. As shown in FIGS. 60A and 60B, a beat signal detected by the photoelectric detector comprises a DC component 303 and an AC component 304. Such a beat signal is amplified by the preamplifier 401 of FIG. 59 at a suitable gain and, after this, the DC component and the AC component are separated from each other by means of the AC/DC separator 402. As an example, the separator 402 may comprise a combination of a low pass filter and a narrow-band amplifier or a capacitor. Here, the DC component is proportional to the intensity change of the zeroth order diffraction light, while the AC component is the beat signal component produced by a particle or fault. The thus separated AC component of the beat signal is such as depicted at 501 in FIG. 60A, for example, and it is applied to the phase comparator 403.

Now, a phase synchronous loop circuit (PLL circuit) which is peculiar to the present embodiment and which is provided by the phase comparator 403, the low pass filter 404, the amplifier 405 and the voltage controlled oscillator 406, will be explained. This is a feedback loop, comprising the phase comparator 403, the low pass filter 404 and the voltage controlled oscillator 406, and it provides a kind of automatic control circuit.

Where no particle or fault is present on the surface to be inspected, no beat signal is produced and the AC component is null. Thus, no input signal is applied to the phase comparator 403, such that a differential voltage 420 outputted is equal to zero. In such case, the voltage controlled oscillator 406 oscillates at a set frequency $\omega_0$. This frequency is usually called a "free running frequency". The frequency of a beat signal to be detected corresponds to the difference $\Delta\omega$ in wavelength between the two lights which are to be optical-heterodyne interfered with each other. For this reason, the free running frequency $\omega_0$ is normally set to be exactly equal to or close to that frequency.

If a particle or fault is present on the surface to be inspected, a beat signal is produced. In response to reception of such a beat signal as an input signal, the phase comparator 403 compares the rising portion of the received beat signal (frequency $\Delta\omega$) with the oscillated frequency of the voltage controlled oscillator 406, with respect to the phase and frequency, and produces a differential voltage 420 which is proportional to the phase difference and frequency difference between these two signals. A high frequency component of this differential voltage is removed by the low pass filter 404. Thus, only the low frequency component is amplified by the amplifier 405, for raising the loop gain, and a control voltage 421 for the voltage controlled oscillator 406 is provided. This control voltage 421 is applied to the voltage controlled oscillator 406 so as to control the oscillation frequency thereof to reduce the difference between it and the frequency $\Delta\omega$ of the input signal. The frequency of the output signal of the voltage controlled oscillator 406 becomes equal to that of the input signal as a result of the operation described above, and this is called "the PLL is locked". As the PLL circuit is locked to the beat signal, the voltage controlled oscillator 406 produces the same frequency as the beat signal frequency $\Delta\omega$. Once it is locked, the state $\omega_0=\Delta\omega$ continues unless a phase difference is produced between the frequencies $\Delta\omega$ and $\omega_0$. But, if in the locked state a phase difference is produced between the frequencies $\Delta\omega$ and $\omega_0$, such difference is detected by the phase comparator 403 and the voltage controlled oscillator 406 is controlled by changing the control voltage thereto to resume the state $\Delta\omega=\omega_0$ to thereby maintain the locked state.

Since the output signal from the voltage controlled oscillator 406 contains a phase shift of 90 deg. due to the PLL circuit, for correction of the same the 90-deg. phase shifter 407 is provided and, by passing the signal through the phase shifter, the phase of the signal of the voltage controlled oscillator 406 is brought into agreement with that of the beat signal. Then, these two signals are applied to the multiplier 408 and, by multiplying them in this multiplier, a wave-rectified detection output is produced. The detection output has a high frequency component which is twice higher than the beat frequency $\Delta\omega$, and, by removing this by using the low pass filter 409, a pulse signal 502 (FIG. 60B) corresponding to an envelop of the beat signal is produced.

Since the PLL circuit is responsive only to a frequency quite close to the free running frequency, it shows very good frequency selectiveness. As a result, it is possible to remove the effect of shot noise of the photoelectric detector and to assure detection of only the beat signal of a frequency $\Delta\omega$, at a high S/N ratio.

The thus produced pulse signal 502 is applied to the peak correcting circuit 410. Since the AC component of the beat signal changes in proportion to a change in intensity of the zeroth order diffraction light (reference light) from the surface inspected, in accordance with such a change the wave height 503 of the pulse signal 502 of FIG. 60B is proportional to the change in intensity of the zeroth order diffraction light. In order to correct this effect, the DC component 303 is monitored through the zeroth order diffraction light monitor 411, and a correction signal 422 is applied to the peak correction circuit 410. Based on this correction signal 422, in the peak correction circuit 410, as an example the amplification rate to the frequency-filtered signal is changed, whereby the pulse height is corrected and the effect of the intensity change of the zeroth order diffraction light is removed. This assures that the intensity of an output pulse produced by the peak correcting circuit 410 is proportional solely to the intensity of scattered light from a particle. The counter 411 provides an appropriate threshold 504 to the noise level, and it evaluates whether the output pulse results from a particle/fault or a noise. The result of counting is applied to the computer 413 in which data memorization, particle size evaluation, mapping, displaying, etc., are executed.

Since in this embodiment a beat signal is processed by a phase synchronous loop (PLL) circuit having superior frequency selectiveness, the effect of shot noise is removed and particle/fault detection of high S/N ratio is assured.

Embodiment 27

Next, an embodiment wherein the signal processing system of the preceding embodiment is improved, will be explained. In the embodiments described hereinbefore, if a particle or fault to be detected is extraordinarily small, the intensity of a signal obtainable from a photoelectric detector becomes very low and, thus, the time width in which a beat signal is produced become very short. In the present embodiment, in consideration of this, the signal processing system is modified so as to provide what may be called a "double heterodyne detection system", to assure good detection of even a very small particle or fault.

Details will now be explained. In the arrangement of FIG. 61, a light source system 200 and a detection optical system 201 are of the same structure as those of any one of the preceding embodiments, and optical heterodyne interference occurs in response to a particle or fault and thus a beat signal is produced by a photoelectric detector 202. Denoted at 203 is an oscillator; at 204 is a multiplying circuit; at 25 is a frequency filter; and 206 is a threshold circuit: and at 207 is a computer.

The higher the frequency of the beat signal detected by the photoelectric detector is, the better the result is. Since the frequency of the beat signal corresponds to the difference in frequency of two light beams which interfere (heterodyne interference) with each other, it is possible to make higher the frequency of the beat signal by providing a larger difference in frequency to them. Assuming now that two frequencies $f_1$ and $f_2$ constituting a beat signal has a difference of, e.g., $|f_1-f_2|=\Delta\omega/2\lambda=10$ GHz, then as described the electric fields $E_1$ and $E_2$ of the light emanating from the detection optical system 201 can be expressed as follows:

$$E_1 = A_1 \cdot \exp[j\{\omega t + \theta_1\}] \qquad (11)$$

$$E_2 = A_2 \cdot \exp[j\{(\omega + \Delta\omega)t + \theta_2\}] \qquad (12)$$

Here, the signal intensity $I_{PD}$ after the photoelectric conversion through the photoelectric detector 202 is expressed as follows:

$$I_{PD} = |E_1 + E_2|^2 \quad (13)$$
$$= A_1^2 + A_2^2 + 2A_1A_2 \cos(\Delta\omega t + \theta_2 - \theta_1)$$

From the third term of equation (13), it follows that the frequency of the beat signal is $\Delta\omega/2\lambda=10$ GHz. If, therefore, the time width of a pulse is about 200 ns., for example, about 2000 periods of 10 GHz beat signals are included in this pulse.

The oscillator 203 produces a sine wave of a frequency slightly different from $\Delta\omega/2\lambda=10$ GHz, and here its frequency $f_{FG}$ is denoted as $f_{FG}=(\Delta\omega+\delta\omega)/2\lambda=10.1$ GHz. The beat signal detected by the photoelectric detector 202 and the signal from the oscillator 203 are applied to the multiplying circuit 204, and they are multiplied. Here, the intensity $I_{FG}$ of the signal from the oscillator 203 is:

$$I_{FG}=D_{FG}+A_{FG} \cos\{(\Delta\omega+\delta\omega)+\theta_{FG}\} \quad (14)$$

Assuming, for simplifying the coefficients of equation (13), that $A_1^2+A_2^2=D_{PD}$ and $2A_1A_2=A_{PD}$, then:

$$I_{PD}=D_{PD}+A_{PD}\cdot\cos(\Delta\omega t+\theta_2-\theta_1)$$

It follows that the signal $I_{MC}$ from the multiplying circuit is:

$$\begin{aligned} I_{MC} =\ & D_{PD}\cdot D_{FG}+ \\ & D_{PD}A_{FG}\cdot\cos\{(\Delta\omega+\delta\omega)t+\theta_{FG}+\} \\ & D_{FG}A_{PD}\cdot\cos(\Delta\omega t+\theta_2-\theta_1)+ \\ & (A_{PD}A_{FG}/2)\cdot\cos(\delta\omega t+\theta_{FG}-\theta_2+\theta_1)+ \\ & (A_{PD}A_{FG}/2)\cos\{(2\Delta\omega+\delta\omega)t+\theta_{FG}+\theta_2-\theta_1\} \end{aligned} \quad (15)$$

Since $\Delta\omega/2\pi=10$ GHz and $f_{FG}=(\Delta\omega+\delta\omega)/2\pi=10.1$ GHz, the frequency in each of the second and third terms of equation (15) is equal to about 10 GHz while that in the fifth term is equal to about 20 GHz. As compared, the frequency in the fourth term is $\delta\omega/2\pi=100$ MHz. On the basis of the output signal from the multiplying circuit 204 as represented by equation (15) and by means of the frequency filter 205, the component of a frequency 100 MHz is extracted. This signal $I_{FF}$ can be expressed as:

$$I_{FF}=(A_{PD}A_{FG}/2)\cdot\cos(\delta\omega t+\theta_{FG}-\theta_2+\theta_1) \quad (16)$$

This signal is applied to the threshold circuit 206 and is compared with a predetermined threshold level. If the signal is higher than the threshold level, it is discriminated that there is a particle or fault. This is counted by the computer 207. Since the amplitude of the signal from the frequency filter 205 is proportional to $A_{FG}$, as seen from equation (16), a further enhancement of the detection sensitivity is attainable by enlarging the amplitude of the oscillator 203.

Figure 62:
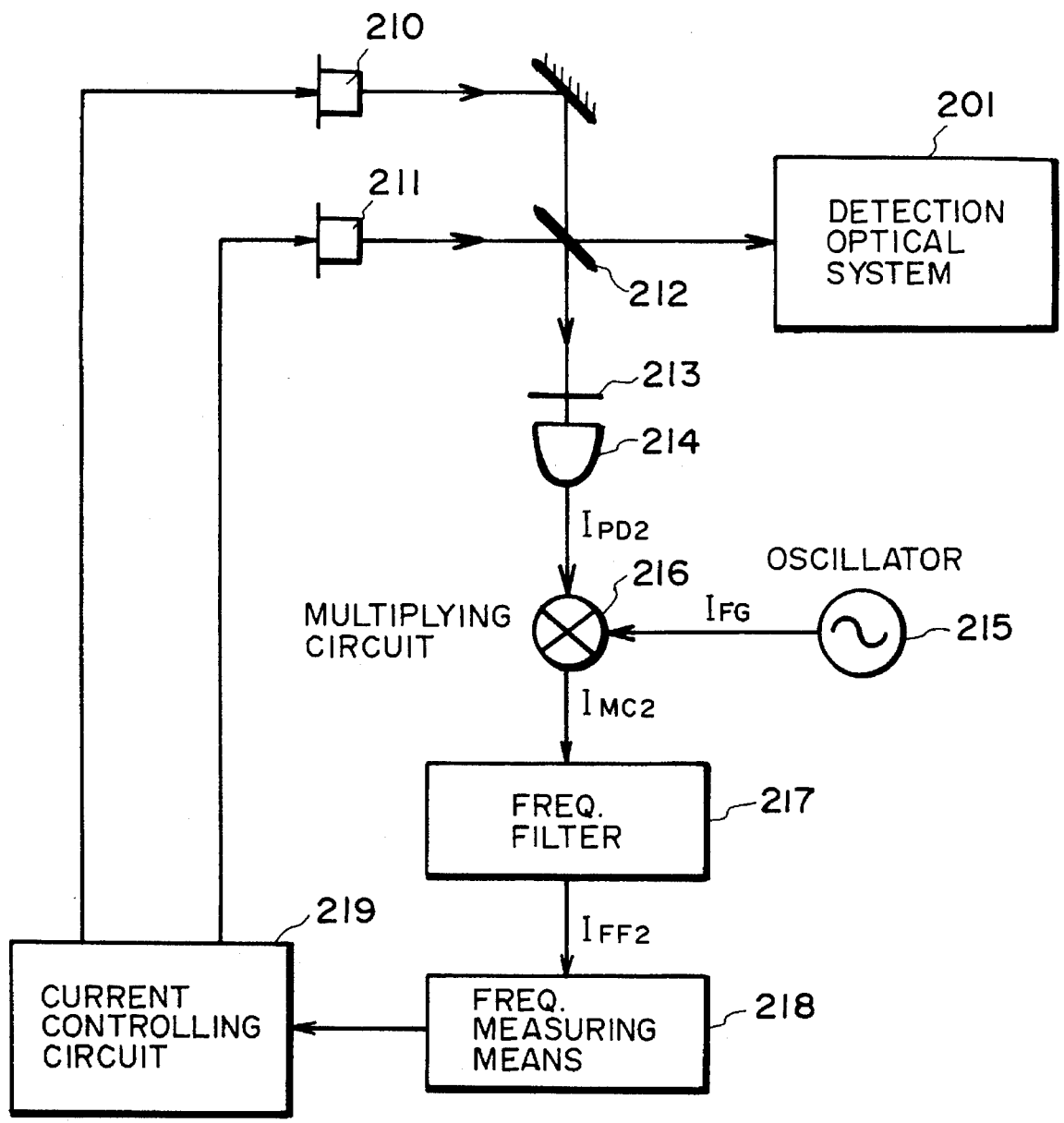
FIG. 62 is a schematic and diagrammatic view of an example of the light source system of the twenty-seventh embodiment.

FIG. 62 shows details of the light source system 200 of FIG. 61. Denoted in the drawing at 210 and 211 are semiconductor lasers oscillating with mutually orthogonal planes of polarization, and they produce laser beams of slightly different frequencies $f_1$ and $f_2$. The lights from these two semiconductor lasers are combined by a half mirror 212 and advance in two directions. One of the lights is directed to the detection optical system as described, and it is used as a particle inspecting light. The other light is directed toward a photoelectric detector 214. Before the detector 214, there is provided a polarization filter 213 having its direction of polarization inclined by 45 deg. so as to cause heterodyne interference of the two frequency components.

Oscillator 215 produces a high-frequency electric signal $I_{FG}$ of a frequency 10.1 GHz, for example. The oscillator 203 of the aforementioned detection system may be used in common as the oscillator 215. The signal $I_{PD2}$ from the detector 214 and the electric signal $I_{FG}$ are applied to a multiplying circuit 216 and they are multiplied. The output signal from the multiplying circuit is applied to a frequency filter 217 which is adapted to selectively extract a frequency component of about 100 MHz. The extracted signal $I_{FF2}$ is applied to a frequency measuring means 218. Current controlling circuit 219 first operates to inject a certain current $I_{LD1}$ into the laser 210. Then, by sweeping an injection current $I_{LD2}$ to the laser 211 with a level close to $L_{LD1}$, the signal $I_{FF2}$ can be applied to the frequency measuring means 218 only when the frequency difference between the signal $I_{PD2}$ from the detector 214 and the signal $I_{FG}$ from the oscillator 215 comes close to 100 MHz, that is, only when the beat signal $I_{PD2}$ is at 10.0 GHz or 10.2 GHz. The frequency measuring means 218 signals to the current controlling circuit 219 the detection of $I_{FF2}$, and the current controlling circuit 219 controls so as to maintain the injection current $I_{LD2}$ to the laser 211 substantially at that level. After this, the frequency measuring means 218 measures the frequency of $I_{FF2}$ and feedbacks any deviation from 100 MHz to the current controlling circuit 219 and, in accordance with this, the current controlling circuit 219 controls the injection current $I_{LD2}$ to the laser 211. With such a feedback system, the beat frequency of a dual-frequency light source can be maintained at a constant and high level.

In this embodiment as described, an optical heterodyne signal and a signal from an oscillator adapted to provide a high-frequency electric signal, of a frequency slightly different from the heterodyne signal, are mutually multiplied by a multiplying circuit, and through a frequency filter a signal of desired frequency is extracted out of an output signal of the multiplying circuit. This enables setting the frequency of the optical heterodyne signal high. Namely, what may be called "double heterodyne detection" is executed. As a consequence, the number of periods of the optical heterodyne signal to be photoelectrically converted by the photoelectric detector when one particle or particulate is to be detected, increases. Also, the occurrence of the optical heterodyne interference can be discriminated more accurately. Further, with an increase in the amplitude of an electric signal, it is possible to enlarge the amplitude of a detection signal. This enables to provide a high detection signal from a weak optical heterodyne signal. Moreover, by means of a frequency filter adapted to selectively extract a particular frequency, it is possible to remove undesirable DC components of a detection signal. This provides assured detection. In summary, the present embodiment assures the following advantageous effects:

(1) Even with heterodyne interference of low intensity, an amplified detection signal is obtainable by enlarging the signal intensity from an oscillator. Thus, an increased detection sensitivity is assured.

(2) Because of the possibility of increasing the beat frequency, the occurrence of beating can be detected even if a particle or the like to be detected is very small and the time period of beat signal production is very short.

(3) Through adjustment of the optical heterodyne frequency and the frequency of a signal from the oscillator, such a frequency being able to be easily extracted by the frequency filter can be set. Thus, a detection signal can be separated from DC components or noises efficiently, and an enhanced S/N ratio is assured.

Embodiment 28

Next, a twenty-eighth embodiment of the present invention will be explained. In the ninth embodiment described above, a high-frequency signal is generated by means of an electric oscillator, for "double heterodyne detection". In this embodiment, as compared, a similar high-frequency signal is generated optically, to execute similar "double heterodyne detection".

Figure 63:
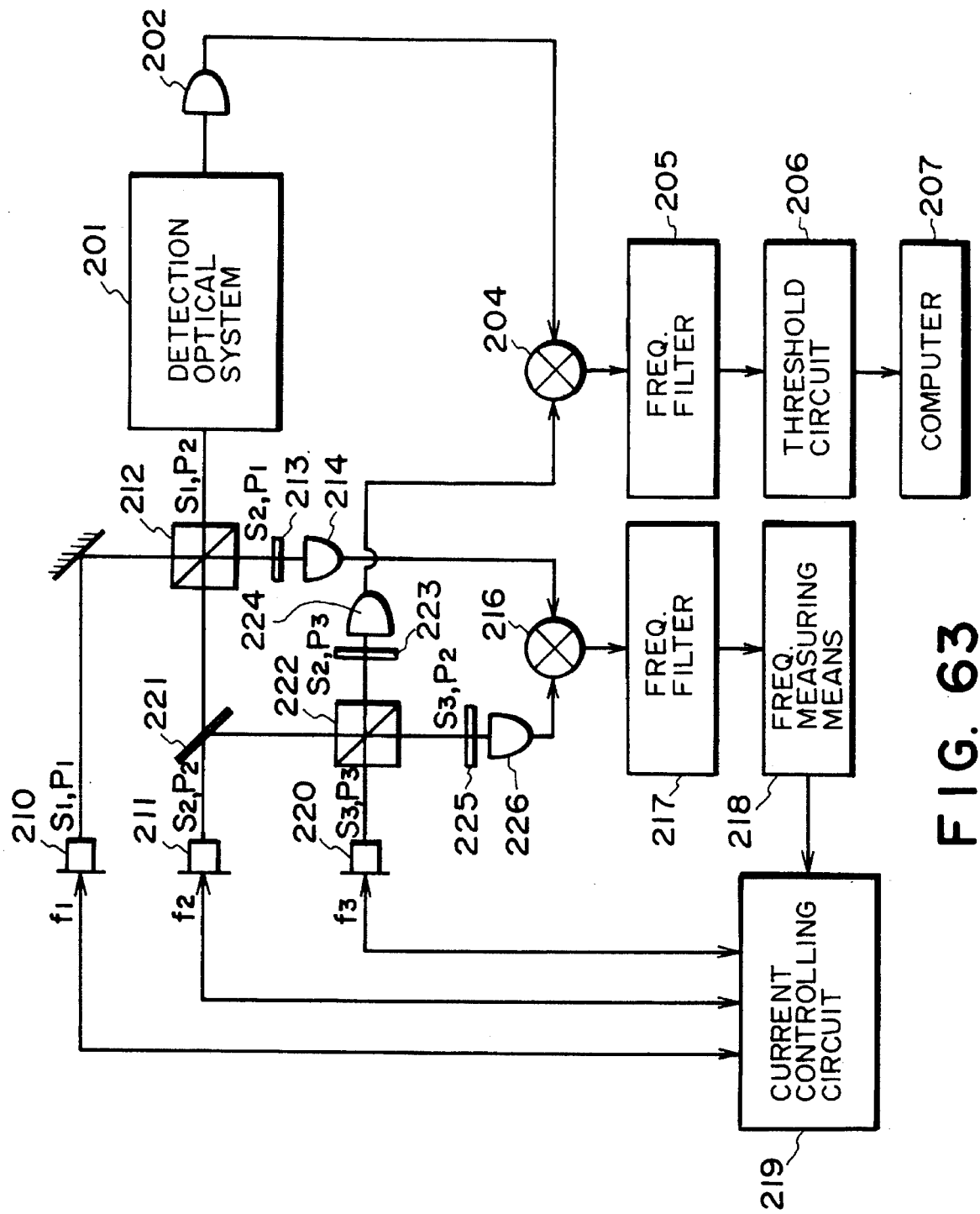
FIG. 63 is a schematic and diagrammatic view of a twenty-eighth embodiment of the present invention.

FIG. 63 shows the structure of this embodiment, which is based on basically the same concept as that of the twenty-seventh embodiment. Like numerals as those in FIGS. 61 and 62 are assigned to corresponding or similar elements. An important structural feature of this embodiment resides in the provision of a semiconductor laser 220, a half mirror 221, a polarization beam splitter 222, a polarization filter 223, a photoelectric detector 224, a polarization filter 225 and a photoelectric detector 226. These elements ensure a similar function as that of the electric oscillator of the ninth embodiment. The semiconductor laser 220 produces a laser beam of a frequency $f_3$ which is slightly different from the frequencies $f_1$ and $f_2$ of semiconductor lasers 210 and 211, respectively. While not shown in the drawing, a quarter phase difference plate is disposed adjacent to the exit portion of each semiconductor laser, so that each laser can provide a laser beam, transformed from linearly polarized light into circularly polarized light. In this embodiment, the semiconductor lasers 210 and 211 have a frequency difference of 10.0 GHz. Thus, a beat signal attributable to a particle of fault and obtainable with a photoelectric detector 202, is 10.0 GHz. Also, the semiconductor lasers 211 and 220 have a frequency difference of 10.1 GHz. Thus, through each of the photoelectric detectors 224 and 226, a beat signal of 10.1 GHz, namely, a signal similar to the high-frequency signal as obtainable through the oscillator of the twenty-seventh embodiment, is obtainable.

In this embodiment, one of the two light beams, more particularly, the light beam from the light source 211, is divided by the half mirror for production of a high-frequency signal. However, this may be replaced by use of an additional or fourth semiconductor laser.

Detection optical system 201 may have a similar structure as that of any one of the embodiments described hereinbefore. Heterodyne interference light obtained therein is detected by the photoelectric detector 202. An output (10.0 MHz) thereof as well as an output (10.1 MHz) of the photodetector 224, detecting the optically produced high-frequency signal, are mutually multiplied by a multiplying circuit 204, such that, through the heterodyne detection based on similar signal processing as in the FIG. 61 example, a particle or fault can be detected with good precision. On the other hand, an output (10.0 MHz) of the photodetector 214 and an output (10.1 MHz) of the photoelectric detector 226 are mutually multiplied by a multiplying circuit 216 and, through similar signal processing as in the FIG. 28 example, the frequency stabilization of the light source means is assured.

Embodiment 29

Figure 64:
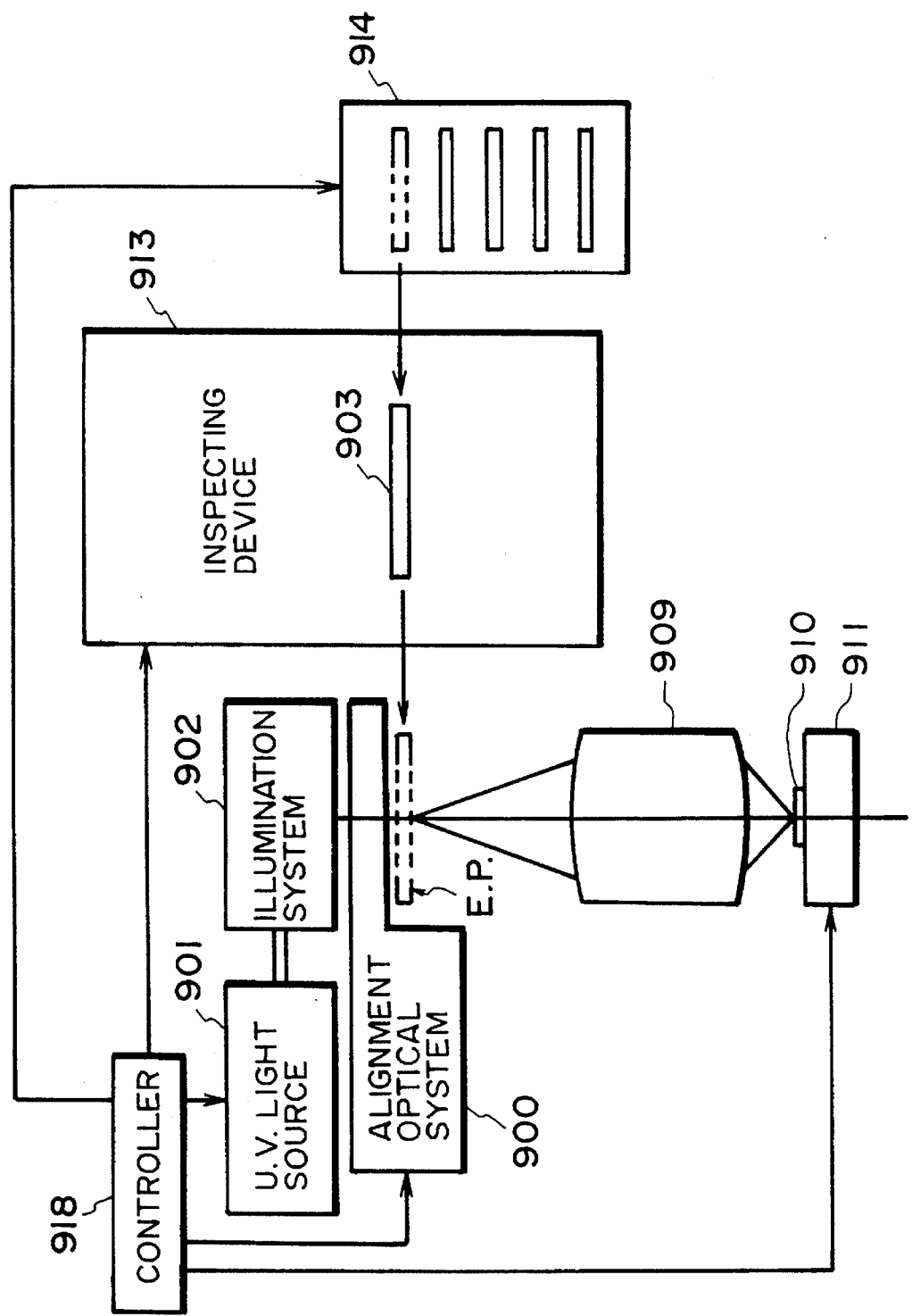
FIG. 64 is a schematic and diagrammatic view of a twenty-ninth embodiment of the present invention, which is applied to a semiconductor device manufacturing system.

FIG. 64 shows an embodiment of a semiconductor device manufacturing system for printing a circuit pattern of an original such as a reticle or photomask upon a silicon wafer. Generally stating, this system comprises an exposure apparatus, an original storing device, an original inspecting device and a controller, all being placed in a clean room.

Denoted at 901 is a deep ultraviolet light source such as an excimer laser, for example, and denoted at 902 is an illumination system unit for illuminating an original, held at an exposure position (E.P.), simultaneously (whole surface illumination) from above and with a predetermined numerical aperture (NA). Denoted at 909 is an ultra-high-resolution lens system (or mirror system) for transferring the circuit pattern formed on the original onto a silicon wafer 910.

Upon printing, the wafer is shifted one-shot by one-shot with stepwise motion of a movable stage 911 so that repeated exposures are made thereto. Denoted at 900 is an alignment optical system for aligning the original and the wafer prior to the exposure operation. It includes at least one original observing microscope system. These elements constitute the exposure apparatus.

On the other hand, denoted at 914 is the original storing device for accommodating therein a plurality of originals. Denoted at 913 is the original inspecting device which has the structure according to any one of the preceding embodiments. The inspecting device 913 serves to execute particle inspection to a selected one of the originals, taken out of the storing device 914, before it is placed at the exposure station EP. The principle and manner of particle inspection is the same as that of the corresponding embodiment. Controller 918 serves to control the sequence of the while system and, as an example, it controls the operation of the storing device 914 and the inspecting device 913 as well as the alignment and exposure operation and wafer stepwise operation which are basic operations of the exposure apparatus.

A semiconductor device manufacturing process using the system of the present embodiment will now be explained. First, an original to be used is taken out of the original storing device 914 and it is placed in the inspecting device 913. Then, particle inspection to this original is executed through the inspecting device. If, as a result of inspection, it is discriminated that no particle is present on the original, the original is then placed at the exposure station EP in the exposure apparatus. Subsequently, a silicon wafer 910 which is an article to be exposed is placed on the movable stage 911. Then, while moving the movable stage 911 stepwise and shifting the wafer one-shot by one-shot in accordance with the step-and-repeat method, the pattern of the original is projected in a reduced scale on different zones of the silicon wafer to expose them. After the exposure process to one wafer is completed, this wafer is off-loaded and a new silicon wafer is loaded, and step-and-repeat exposures of it to the pattern of the original are repeated in the same manner.

The "exposed" wafer whose exposure process is completed, is subjected to a developing process, an etching process and so on through respective devices provided separately from the illustrated system. After this, it is subjected to assembling processes such as dicing, wire bonding, packaging and so on, whereby semiconductor devices are finished.

Embodiment 30

Figure 65:
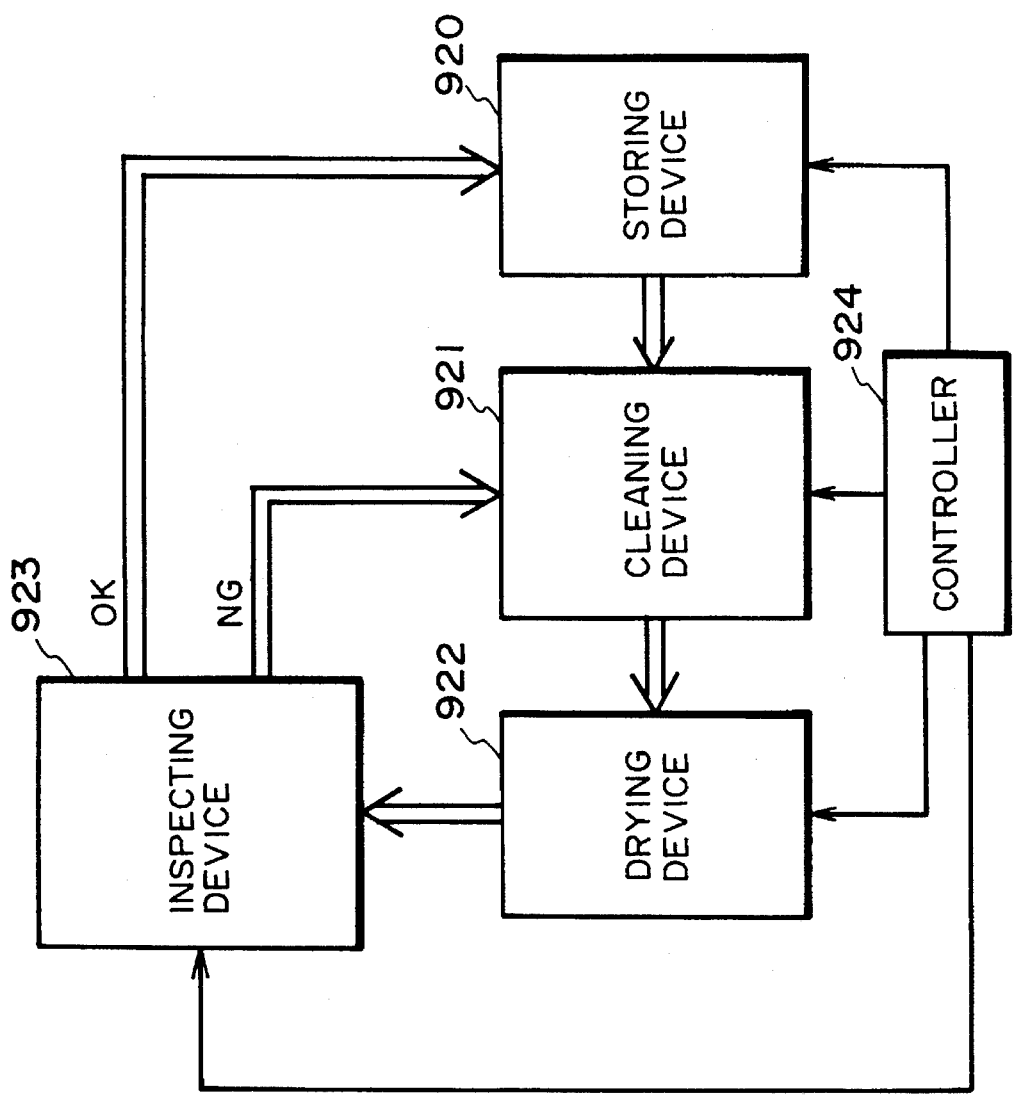
FIG. 65 is a schematic and diagrammatic view of a thirtieth/embodiment of the present invention, which is applied to an original cleaning and inspection system.
Figure 66:
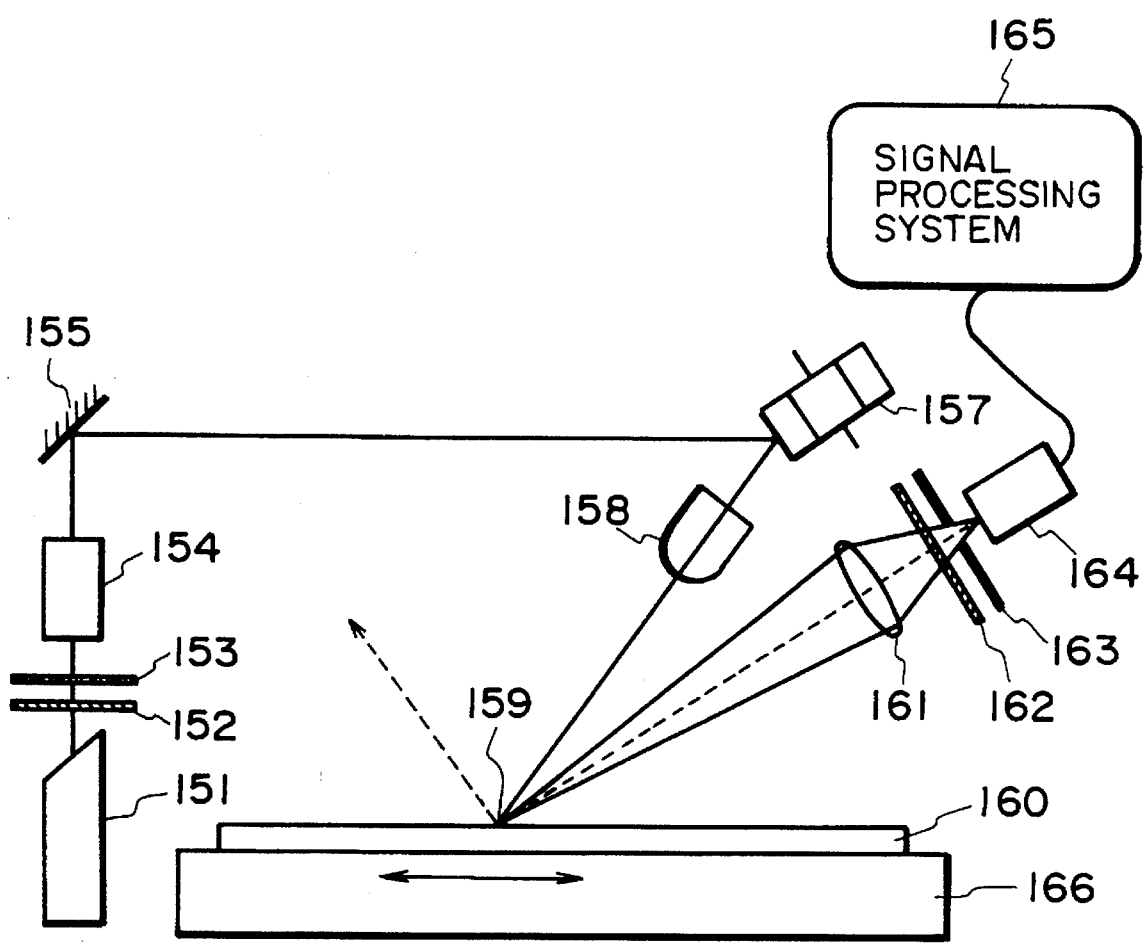
FIG. 66 is a schematic view of a known type inspection apparatus.

FIG. 65 shows an embodiment of an original cleaning and inspecting system for manufacture of semiconductor devices. Generally stating, the system comprises an original storing device, a cleaning device, a drying device, an inspecting device and a controller, all being placed in a clean room.

Denoted at 920 is an original storing device for storing therein some originals. It is operable to selectively supply an original to be cleaned. Denoted at 921 is a cleaning device for cleaning an original by using pure water. Denoted at 922 is a drying device for drying a cleaned original. Denoted at 923 is an original inspecting device which is arranged in accordance with any one of the preceding embodiments and which serves to execute particle inspection to a cleaned original. Denoted at 924 is a controller which serves to execute the sequence control to the system as a whole.

The operation will be explained. First, an original to be cleaned is taken out of the original storing device 920 and it is moved into the cleaning device 921. After the cleaning in the cleaning device 921, the cleaned original is moved into the drying device 922 and is dried. After it is dried, it is moved into the inspecting device 923. In this inspecting device, any foreign particles on this original is inspected in accordance with the method of any one of the embodiments described hereinbefore. If as a result of inspection no particle is detected, the original is moved back into the storing device 920. If any particle is detected, the original is moved back to the cleaning device 921 and, after repetition of the cleaning and drying operation, it is inspected again. This is repeated until particles are totally removed, and a completely cleaned original is moved back into the storing device 920.

Subsequently, such a cleaned original is placed in an exposure apparatus and the printing of a circuit pattern of the original on a silicon wafer is executed, for manufacture of semiconductor devices.

While the invention has been described with reference to the structures disclosed herein, it is not confined to the details set forth and this application is intended to cover such modifications or changes as may come within the purposes of the improvements or the scope of the following claims.

What is claimed is:

1. An inspection apparatus for inspecting a particle, if any, on a substrate having a pattern, said apparatus comprising:

light producing means for producing (i) first light having a first state of polarization and a first wavelength, and (ii) second light having a second state of polarization, different from the first state of polarization, and a second wavelength, different from the first wavelength;

light projecting means for projecting at least the first light to a position of inspection upon the substrate;

detecting means for detecting heterodyne interference light produced on the basis of the second light and light scattered at the inspection position and having its state of polarization changed, by the scattering, from the first state of polarization; and inspecting means for inspecting a particle, if any, on the substrate on the basis of an output of said detecting means.

2. An inspection apparatus according to claim 1, wherein said light projecting means comprises scanning means for deflecting at least the first light to optically scan a surface to be inspected.

3. An apparatus according to claim 2, further comprising a lens system for imaging a scanning area of the surface upon a detection surface of said detecting means.

4. An apparatus according to claim 1, wherein the second light is projected at the same position irradiated with the first light.

5. An apparatus according to claim 1, wherein the second light is not projected on the surface to be inspected and wherein the second light and scattered light resulting from the first light are caused to interfere with each other.

6. An apparatus according to claim 1, wherein said light producing means produces the first light and second light in a combined flux.

7. An apparatus according to claim 1, wherein said light producing means produces the first light and the second light separately.

8. An apparatus according to claim 1, wherein the first light comprises linearly polarized light of a predetermined direction while the second light comprises linearly polarized light of another direction different from the predetermined direction.

9. An apparatus according to claim 1, wherein at least one of the first light and second light comprises circularly polarized light.

10. An apparatus according to claim 1, wherein said detecting means detects interference light produced on the basis of the second light and light advancing in a particular direction sideways to the direction of incidence of the first light.

11. An apparatus according to claim 10, wherein the particular direction has an angle in a range of 90–180 deg.

12. An apparatus according to claim 1, further comprising a setting mechanism for setting the state of polarization of the first light.

13. An apparatus according to claim 1, further comprising a setting mechanism for setting the state of polarization of the second light.

14. An apparatus according to claim 1, further comprising inspecting means comprising signal processing means including a phase synchronization loop circuit, wherein said inspecting means inspects the state of the inspection position on the basis of processing, through said signal processing means, a beat signal of the detected interference light.

15. An apparatus according to claim 1, further comprising (i) oscillating means for producing a high frequency signal of a frequency different from a beat signal of the detected interference light, (ii) multiplying means for multiplying the beat signal and the high frequency signal, and (iii) inspecting means for inspecting the state of the inspection position on the basis of the result of multiplication.

16. A transfer system, comprising:

an inspection apparatus as recited in claim 1, for inspecting an original having a pattern; and a transfer apparatus for transferring onto a substrate the pattern of the original inspected by said inspection apparatus.

17. An original cleaning and inspecting system, comprising:

a cleaning apparatus for cleaning an original; and an inspection apparatus as recited in claim 1, for inspecting the original cleaned by said cleaning apparatus.

18. An apparatus according to claim 1, wherein the inspection position lies on a mask having a pattern to be transferred, and wherein a particle if any on the mask can be inspected while being distinguished from the pattern of the mask.

19. An inspection apparatus, comprising:

first light producing means for producing first light having a first wavelength, and second light having a second wavelength, different from the first wavelength;

second light producing means for producing third light having a third wavelength, and fourth light having a fourth wavelength, different from the third wavelength;

light projecting means for projecting at least the first light and the third light to a position of inspection;

first detecting means for detecting heterodyne interference light produced on the basis of the second light and light scattered at the inspection position as a result of irradiation by the first light; and second detecting means for detecting heterodyne interference light produced on the basis of the fourth light and light scattered at the inspection position as a result of irradiation by the third light.

20. An apparatus according to claim 19, wherein the first light and the second light have different states of polarization, and wherein the third light and the fourth light have different states of polarization.

21. An apparatus according to claim 19, wherein the inspection position lies on a mask having a pattern to be transferred, and wherein a particle if any on the mask can be inspected while being distinguished from the pattern of the mask.

22. An inspection apparatus for inspecting a particle, if any, on a substrate having a pattern, said apparatus comprising:

light producing means for producing (i) first light having a first state of polarization and a first wavelength, and (ii) second light having a second state of polarization, different from the first state of polarization and a second wavelength, different from the first wavelength;

light projecting means for projecting at least the first light to a position of inspection upon the substrate;

first detecting means for detecting heterodyne interference light produced on the basis of the second light and light scattered in a first direction from the inspection position as a result of irradiation with the first light;

second detecting means for detecting heterodyne interference light produced on the basis of the second light and light scattered in a second direction, different from the first direction, from the inspection position as a result of irradiation with the first light; and inspecting means for inspecting a particle, if any, on the substrate on the basis of outputs of said first and second detecting means.

23. An apparatus according to claim 22, wherein the inspection position lies on a mask having a pattern to be transferred, and wherein a particle if any on the mask can be inspected while being distinguished from the pattern of the mask.

24. An inspection method for inspecting a particle, if any, on a substrate having a pattern, said method comprising the steps of:

producing (i) first light having a first state of polarization and a first wavelength, and (ii) second light having a second state of polarization, different from the first state of polarization, and a second wavelength, different from the first wavelength;

projecting at least the first light to a position of inspection upon the substrate;

detecting heterodyne interference light produced on the basis of the second light and light scattered at the inspection position and having its state of polarization changed, by the scattering, from the first state of polarization; and inspecting a particle, if any, on the substrate on the basis of the detection in said detecting step.

25. An inspection method according to claim 24, wherein said projecting step comprises deflecting at least the first light to optically scan a surface to be inspected.

26. A device manufacturing method, comprising the steps of:

inspecting an original having a pattern in accordance with an inspection method as recited in claim 24; and transferring onto a substrate the pattern of the inspected original.

27. A device manufactured by a device manufacturing method which comprises the steps of:

inspecting an original having a pattern in accordance with an inspection method as recited in claim 24; and transferring onto a substrate the pattern of the inspected original.

28. A method according to claim 24, wherein the inspection position lies on a mask having a pattern to be transferred, and wherein a particle if any on the mask can be inspected while being distinguished from the pattern of the mask.

* * * * *

UNITED STATES PATENT AND TRADEMARK OFFICE
CERTIFICATE OF CORRECTION

PATENT NO. : 5,486,919
DATED : January 23, 1996
INVENTOR(S) : Toshihiko TSUJI, et al.

It is certified that error appears in the above-indentified patent and that said Letters Patent is hereby corrected as shown below:

ON THE COVER PAGE:

Under "Foreign Application Priority Data" item [30]

"4-022675" should read --5-022675--;
4-048064" should read --5-048064--; and
4-099541" should read --5-099541--.

COLUMN 5:

Line 2, "thirtieth/embodiment" should read --thirtieth embodiment--;
Line 11, "is" should read --are--;
Line 14, "the in" should read --in the--;
Line 46, "is" should read --are--; and
Line 55, "it" should be deleted.

UNITED STATES PATENT AND TRADEMARK OFFICE
CERTIFICATE OF CORRECTION

PATENT NO. : 5,486,919
DATED : January 23, 1996
INVENTOR(S) : Toshihiko TSUJI, et al.

It is certified that error appears in the above-indentified patent and that said Letters Patent is hereby corrected as shown below:

COLUMN 9:

Line 33, Equation (8):

" $DC\ comp. = (\alpha Ep)^2 + \Delta E_1 p^2 \approx (\Delta Ep)^2$ " should read -- $DC\ comp. = (\alpha Ep)^2 + \Delta E_1 p^2 \approx (\alpha Ep)^2$ --.

COLUMN 13:

Line 48, "comprise" should read --comprises--.

COLUMN 16:

Line 27, "of" should be deleted.

COLUMN 18:

Line 61, "reverted." should read --reversed.--.

UNITED STATES PATENT AND TRADEMARK OFFICE
CERTIFICATE OF CORRECTION

PATENT NO. : 5,486,919
DATED : January 23, 1996
INVENTOR(S) : Toshihiko TSUJI, et al.

It is certified that error appears in the above-indentified patent and that said Letters Patent is hereby corrected as shown below:

COLUMN 29:

Line 61, "Of" should read --of--.

COLUMN 40:

Line 58:

" $|f_1 - f_2| = \Delta\omega/2\lambda = 10$ GHz " should read

-- $|f_1 - f_2| = \Delta\omega/2\pi = 10$ GHz --.

COLUMN 41:

Line 6:

"$\Delta\omega/2\lambda = 10$ GHz." should read

--$\Delta\omega/2\pi = 10$ GHz.--;

UNITED STATES PATENT AND TRADEMARK OFFICE
CERTIFICATE OF CORRECTION

PATENT NO. : 5,486,919
DATED : January 23, 1996
INVENTOR(S) : Toshihiko TSUJI, et al.

It is certified that error appears in the above-indentified patent and that said Letters Patent is hereby corrected as shown below:

<u>COLUMN 41</u>: (cont.)

Line 10:

"$\Delta\omega/2\lambda=10$ GHz." should read

--$\Delta\omega/2\pi=10$ GHz.--;

Line 11:

"$f_{FG}=(\Delta\omega+\delta\omega)/2\lambda=10.1$ GHz." should read

-- $f_{FG}=(\Delta\omega+\delta\omega)/2\pi=10.1$ GHz. --; and

Line 27:

" $D_{PD}A_{FG}\cdot\cos\{(\Delta\omega+\delta\omega)t+\theta_{FG}+\}$ " should read -- $D_{PD}A_{FG}\cdot\cos\{(\Delta\omega+\delta\omega)t+\theta_{FG}\}+$ --.

UNITED STATES PATENT AND TRADEMARK OFFICE
CERTIFICATE OF CORRECTION

PATENT NO. : 5,486,919  
DATED : January 23, 1996  
INVENTOR(S) : Toshihiko TSUJI, et al.

It is certified that error appears in the above-indentified patent and that said Letters Patent is hereby corrected as shown below:

COLUMN 44:

Line 17, "while" should read --whole--.

COLUMN 47:

Line 28, "particle if any" should read --particle, if any,--.

COLUMN 48:

Line 32, "particle if any" should read --particle, if any,--.

Signed and Sealed this

Twentieth Day of August, 1996

Attest:

BRUCE LEHMAN

Attesting Officer   Commissioner of Patents and Trademarks